United States Patent
Anderson

(10) Patent No.: US 10,370,718 B2
(45) Date of Patent: Aug. 6, 2019

(54) USE OF HLA GENETIC STATUS TO ASSESS OR SELECT TREATMENT OF CELIAC DISEASE

(71) Applicant: ImmusanT, Inc., Cambridge, MA (US)

(72) Inventor: Robert P. Anderson, Shrewsbury, MA (US)

(73) Assignee: ImmusanT, Inc., Cambridge, MA (US)

( * ) Notice: Subject to any disclaimer, the term of this patent is extended or adjusted under 35 U.S.C. 154(b) by 58 days.

(21) Appl. No.: 15/515,185

(22) PCT Filed: Sep. 29, 2015

(86) PCT No.: PCT/US2015/052939
§ 371 (c)(1),
(2) Date: Mar. 29, 2017

(87) PCT Pub. No.: WO2016/054038
PCT Pub. Date: Apr. 7, 2016

(65) Prior Publication Data
US 2017/0218453 A1 Aug. 3, 2017

Related U.S. Application Data

(60) Provisional application No. 62/057,167, filed on Sep. 29, 2014.

(51) Int. Cl.
*G01N 33/68* (2006.01)
*C12Q 1/6883* (2018.01)
*A61K 38/16* (2006.01)

(52) U.S. Cl.
CPC .......... *C12Q 1/6883* (2013.01); *A61K 38/168* (2013.01); *G01N 33/6863* (2013.01); *C12Q 2600/106* (2013.01); *C12Q 2600/118* (2013.01); *C12Q 2600/156* (2013.01); *C12Q 2600/158* (2013.01); *C12Q 2600/16* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,740,371 A | 4/1988 | St. Remy et al. |
| 5,128,270 A | 7/1992 | Delacroix et al. |
| 5,334,504 A | 8/1994 | Wood et al. |
| 5,494,799 A | 2/1996 | Wood et al. |
| 5,547,669 A | 8/1996 | Rogers et al. |
| 5,750,356 A | 5/1998 | Spack et al. |
| 5,846,740 A | 12/1998 | Tobin et al. |
| 5,998,366 A | 12/1999 | Tobin et al. |
| 6,218,132 B1 | 4/2001 | Spack et al. |
| 6,300,308 B1 | 10/2001 | Schroit |
| 6,455,267 B1 | 9/2002 | Tobin et al. |
| 6,759,234 B1 | 7/2004 | Gefter et al. |
| 6,806,354 B2 | 10/2004 | Schroit |
| 7,094,555 B2 | 8/2006 | Kwok et al. |
| 7,144,569 B1 | 12/2006 | Anderson et al. |
| 7,202,216 B2 | 4/2007 | Sollid et al. |
| 7,303,871 B2 | 12/2007 | Hausch et al. |
| 7,361,480 B2 | 4/2008 | Maki et al. |
| 7,462,688 B2 | 12/2008 | Khosla et al. |
| 7,563,864 B2 | 7/2009 | Marti et al. |
| 7,604,957 B2 | 10/2009 | Fine |
| 7,608,392 B2 | 10/2009 | Rothel et al. |
| 7,888,460 B2 | 2/2011 | Anderson et al. |
| 8,053,235 B2 | 11/2011 | Buckner et al. |
| 8,329,144 B2 | 12/2012 | Anderson et al. |
| 8,378,072 B2 | 2/2013 | Bonnin |
| 8,426,145 B2 | 4/2013 | Khosla et al. |
| 8,835,603 B2 | 9/2014 | Anderson et al. |
| 9,464,120 B2 | 10/2016 | Anderson et al. |
| 2003/0215438 A1* | 11/2003 | Hausch ................. A61K 31/42 424/94.63 |
| 2005/0014205 A1 | 1/2005 | Rothel et al. |
| 2005/0249719 A1 | 11/2005 | Shan et al. |
| 2005/0256054 A1 | 11/2005 | Sollid et al. |
| 2006/0024334 A1 | 2/2006 | Larche et al. |
| 2006/0154853 A1 | 7/2006 | Steptoe et al. |

(Continued)

FOREIGN PATENT DOCUMENTS

| | | |
|---|---|---|
| AU | 2003277989 B2 | 6/2004 |
| CA | 1299099 C | 4/1992 |

(Continued)

OTHER PUBLICATIONS

Fallang et al. Nature Immunology. 2009. 10(10):1096-1102. (Year: 2009).*
International Search Report and Written Opinion dated Dec. 16, 2015 for Application No. PCT/US2015/052939.
International Preliminary Report on Patentability dated Apr. 13, 2017 for Application No. PCT/US2015/052939.
[No Author Listed], Biosis Chem Abstracts Database. Accession No. PREV201100403721. 2005. Gregor et al., Gastroenterol. May 2011;5(1):S437-8. Abstract.
[No Author Listed], CXCL10 Mouse ELISA Kit, Catalog No. BMS6018. Aug. 17, 2008—date provided by Google®. Last Accessed on Apr. 10, 2018 from https://www.thermofisher.com/order/catalog/product/BMS6018.

(Continued)

*Primary Examiner* — Joseph G. Dauner
(74) *Attorney, Agent, or Firm* — Wolf, Greenfield & Sacks, P.C.

(57) ABSTRACT

Provided herein are methods of adjusting or selecting a gluten peptide therapy based on the human leukocyte antigen (HLA) genotype, in particular HLA-DQ2.5 homozygosity, of a subject having or suspected of having Celiac disease. Also provided herein are methods of identifying (e.g., diagnosing) a subject, such as a subject having or suspected of having Celiac disease and/or assessing the efficacy of treatment of Celiac disease, e.g. by determining responsiveness to a therapeutic gluten peptide composition or cytokine response, and kits relating thereto.

13 Claims, 4 Drawing Sheets
Specification includes a Sequence Listing.

(56) References Cited

U.S. PATENT DOCUMENTS

| | | |
|---|---|---|
| 2006/0178299 A1 | 8/2006 | Anderson et al. |
| 2006/0189540 A1 | 8/2006 | Khosla et al. |
| 2006/0240475 A1 | 10/2006 | Khosla et al. |
| 2006/0286601 A1 | 12/2006 | Marti et al. |
| 2008/0145837 A1 | 6/2008 | Paulie et al. |
| 2008/0175971 A1 | 7/2008 | Anderson et al. |
| 2008/0318852 A1 | 12/2008 | Anderson et al. |
| 2009/0053297 A1 | 2/2009 | Balu-Iyer et al. |
| 2009/0156490 A1 | 6/2009 | Khosla et al. |
| 2009/0226471 A1 | 9/2009 | Kwok et al. |
| 2009/0269285 A1 | 10/2009 | Anderson et al. |
| 2009/0311214 A1 | 12/2009 | Mann et al. |
| 2010/0221712 A1 | 9/2010 | Radford et al. |
| 2011/0293644 A1 | 12/2011 | Anderson et al. |
| 2011/0311536 A1 | 12/2011 | von Boehmer et al. |
| 2012/0083004 A1 | 4/2012 | Khosla et al. |
| 2012/0107847 A1 | 5/2012 | Bruins et al. |
| 2013/0058970 A1 | 3/2013 | Kishimoto et al. |
| 2013/0078267 A1 | 3/2013 | Anderson et al. |
| 2015/0050303 A1 | 2/2015 | Anderson et al. |
| 2015/0320887 A1 | 11/2015 | Elli et al. |
| 2016/0041148 A1 | 2/2016 | Anderson et al. |
| 2016/0238590 A1 | 3/2016 | Anderson et al. |
| 2016/0220629 A1 | 8/2016 | Anderson et al. |
| 2017/0042991 A1 | 2/2017 | Anderson et al. |
| 2017/0045513 A1 | 2/2017 | Anderson et al. |
| 2017/0045529 A1 | 2/2017 | Anderson et al. |
| 2017/0059582 A1 | 3/2017 | Anderson et al. |
| 2017/0097346 A1 | 4/2017 | Anderson et al. |
| 2017/0158743 A1 | 6/2017 | Anderson et al. |
| 2017/0232083 A1 | 8/2017 | Anderson et al. |

FOREIGN PATENT DOCUMENTS

| | | |
|---|---|---|
| CN | 1703505 A | 11/2005 |
| EP | 0296158 B1 | 6/1992 |
| EP | 0905518 A1 | 3/1999 |
| EP | 1332760 A1 | 8/2003 |
| EP | 1453539 B1 | 9/2004 |
| EP | 1393070 B1 | 8/2007 |
| EP | 1561106 B1 | 4/2009 |
| EP | 1740949 B1 | 11/2011 |
| EP | 2409711 A1 | 1/2012 |
| EP | 2762487 A1 | 8/2014 |
| IT | 2007FE003 | 2/2007 |
| WO | WO 1993/19178 A2 | 9/1993 |
| WO | WO 1996/06630 A1 | 3/1996 |
| WO | WO 1996/07428 A1 | 3/1996 |
| WO | WO 2001/25793 A2 | 4/2001 |
| WO | WO 2002/083722 A2 | 10/2002 |
| WO | WO 2003/066079 A2 | 8/2003 |
| WO | WO 2003/096979 A2 | 11/2003 |
| WO | WO 2003/096984 A2 | 11/2003 |
| WO | WO 2003/104273 A2 | 12/2003 |
| WO | WO 2004/042396 A1 | 5/2004 |
| WO | WO 2004/045392 A2 | 6/2004 |
| WO | WO 2005/105129 A2 | 11/2005 |
| WO | WO 2007/019411 A2 | 2/2007 |
| WO | WO 2007/022477 A2 | 2/2007 |
| WO | WO 2007/047303 A2 | 4/2007 |
| WO | WO 2008/028489 A2 | 3/2008 |
| WO | WO 2008/052185 A2 | 5/2008 |
| WO | WO 2008/090223 A2 | 7/2008 |
| WO | WO 2008/113119 A1 | 9/2008 |
| WO | WO 2009/131909 A2 | 10/2009 |
| WO | WO 2009/139887 A2 | 11/2009 |
| WO | WO 2010/009494 A1 | 1/2010 |
| WO | WO 2010/060155 A1 | 6/2010 |
| WO | WO 2011/000773 A1 | 1/2011 |
| WO | WO 2011/075773 A1 | 6/2011 |
| WO | WO 2011/146968 A1 | 12/2011 |
| WO | WO 2013/000021 A1 | 1/2013 |
| WO | WO 2013/016427 A1 | 1/2013 |
| WO | WO 2013/085851 A2 | 6/2013 |
| WO | WO 2014/152233 A1 | 9/2014 |
| WO | WO 2015/038624 A1 | 3/2015 |
| WO | WO 2015/041680 A1 | 3/2015 |
| WO | WO 2015/164714 A1 | 10/2015 |
| WO | WO 2015/164717 A1 | 10/2015 |
| WO | WO 2015/164721 A1 | 10/2015 |
| WO | WO 2015/164722 A1 | 10/2015 |
| WO | WO 2015/164727 A1 | 10/2015 |
| WO | WO 2015/164747 A1 | 10/2015 |
| WO | WO 2015/164752 A1 | 10/2015 |
| WO | WO 2016/054038 A1 | 4/2016 |
| WO | WO 2017/049035 A1 | 3/2017 |

OTHER PUBLICATIONS

[No Author Listed], Diagnosis and treatment of coeliac disease targeting gluten-specific T cells. Presentation. Burnet Institute. Melbourne, Australia. May 29, 2011. 48 pages.

[No Author Listed], ImmusanT Initiates Clinical Trials of Nexvax2 Therapeutic Vaccine for Celiac Disease. ImmusanT Press Release. Cambridge, MA. Sep. 4, 2012. 2 pgs.

[No Author Listed], ImmusanT Names Patrick Griffin as Chief Medical Officer, Expands Management Team. ImmusanT Press Release. Cambridge, MA. Mar. 19, 2012. 2 pgs.

[No Author Listed], ImmusanT Raises $20 Million in Series A Financing to Advance Immunotherapeutic and Diagnostic for Celiac Disease. ImmusanT Press Release. Cambridge, MA. Dec. 13, 2011. 2 pgs.

[No Author Listed], ImmusanT Reports Positive Results from Nexvax2 Phase 1 Study in Celiac Disease: Data Featured in Poster of Distinction and Symposia on Advances in Celiac Disease at Digestive Disease Week. Chicago. Illinois, May 9, 2011. 3 pgs.

[No Author Listed], IP-10 (Interferon Gamma-Induced Protein 10). Jun. 10, 2005—date provided by Google®. Last Accessed on Apr. 10, 2018 from https://pacbio.com/biomarker/assay-detail/226/.

[No Author Listed], Link Between Gluten and Immune Reaction Revealed for HLA DQ8 Celiac Disease. ImmusanT Press Release. Cambridge, MA. Oct. 11, 2012. 2 pgs.

[No Author Listed], Safety and tolerability of Nexvax2 in subjects with celiac disease. Clinical Trial Identifier NCT02528799. ImmusanT, Inc. Clinicaltrials.gov. Aug. 17, 2015. Retrieved online via https://clinicaltrials.gov/ct2/show/NCT02528799?term=NexVax2&rank=1. 4 pages.

[No Author Listed], Safety study of Nexvax2 in subjects with coeliac disease. Clinical Trial Identifier NCT00879749. Nexpep Pty Ltd. Clinicaltrials.gov. Apr. 5, 2011. Retrieved online via https://clinicaltrials.gov/ct2/show/NCT00879749?term=NexVax2&rank=2. 3 pages.

[No Author Listed], Start-Up ImmunsanT Seeks to Restore Tolerance to Gluten in Celiac Disease with Immunotherapy. PR Newswire. Mar. 3, 2011. Last Accessed on Nov. 13, 2012 from http://www.prnewswire.com/news-releases/start-up-immusant-seeks-to-restore-tolerance-to-gluten-in-celiac-disease-with-immunotherapy-117996359.html.

[No Author Listed], Vaccination for celiac disease: utopia or concrete hope for celiac disease recovery. AIC Presentation. Florence, Italy. Mar. 30, 2012. 23 pages.

[No Author Listed], WPI Database Submission, Accession No. AED68481; Shan et al..; Jan. 12, 2006. 2 pages.

Anderson et al., Acrocyanosis due to imipramine. Arch Dis Child. Feb. 1988;63(2):204-5.

Anderson et al., Antagonists and non-toxic variants of the dominant wheat gliadin T cell epitope in coeliac disease. Gut. Apr. 2006;55(4):485-91. Epub Nov. 18, 2005.

Anderson et al., Bioactivity of peptides homologous to the coeliac disease-specific dominant A-gliadin T cell epitope. 2001. Abstract 3694.

Anderson et al., Bioactivity of peptides homologous to the coeliac disease-specific dominant T-cell epitope. British Soc Gast Poster. 2001. 1 page.

Anderson et al., Bioactivity of peptides homologous to the coeliac disease-specific dominant T-cell epitope. DDW Poster. 2001. 1 page.

(56) References Cited

OTHER PUBLICATIONS

Anderson et al., Celiac disease associated with HLA-DQ8 and DQ2 have different T-cell repertoires in vivo. 2003. Abstract 130.
Anderson et al., Celiac Disease. Chapter 22 in Evidence-Based Gastroenterology. Eds Irvine et al. 2000. BC Decker Inc. Ontario, Canada. pp. 307-322.
Anderson et al., Coeliac disease. Check Program of Self Assessment. 2005. The Royal Australian College of General Practitioners. Victoria, Australia. pp. 1-32.
Anderson et al., Definitive T cell epitope mapping for a human disease: gluten challenge in coeliac disease identifies a dominant transglutaminase-deamidated T cell epitope. 2001 Kiel Conference Proceedings. 13 pgs.
Anderson et al., In vivo antigen challenge in celiac disease identifies a single transglutaminase-modified peptide as the dominant A-gliadin T-cell epitope. Nat Med. Mar. 2000;6(3):337-42.
Anderson et al., In vivo cross-reactivity of wheat and rye T-cell epitopes in celiac disease. AGA Abstracts 2003. Abstract W1364.
Anderson et al., Peripheral blood T cells induced by gluten challenge in coeliac disease target a specific molecular motif and express a gut-homing integrin. 2001 Abstract 3695.
Anderson et al., Peripheral blood T cells induced by gluten challenge in coeliac disease target a specific motif and express a gut-homing integrin. DDW Poster. 2001. 1 page.
Anderson et al., Screening for coeliac disease: integration of technology and stakeholders. EliA™ J. 2004;1:1-11.
Anderson et al., T cells in peripheral blood after gluten challenge in coeliac disease. Gut. Sep. 2005;54(9):1217-23.
Anderson et al., Vaccine against autoimmune disease: antigen-specific immunotherapy. Curr Opin Immunol. Jun. 2013;25(3):410-7. doi: 10.1016/j.coi.2013.02.004. Epub Mar. 13, 2013.
Anderson, Translating discovery of toxic gluten peptides to a peptide immunotherapy for coeliac disease. Presentation given in Wellington, New Zealand. 2010. 77 pages.
Anderson, A blueprint for the future of coeliac disease. Presentation for NZ Coeliac Society. 2011. 37 pages.
Anderson, A phase I study to determine safety, tolerability and bioactivity of Nexvax2® in HLA DQ2+ volunteers with celiac disease following long-term, strict gluten-free diet. Presentation. Kiama NSW. 2011. 15 pages.
Anderson, Coeliac disease in a select population: optimizing serogenetic testing. Presentation. The George Institute. Sydney, Australia. 2010. 43 pages.
Anderson, Coeliac disease. Aust Fam Physician. Apr. 2005;34(4):239-42.
Anderson, Coeliac Disease: Diagnosis without biopsy, and therapy without dietary changes. Swiss Coeliac Day Presentation. Zurich, Switzerland. 2011. 53 pages.
Anderson, Coeliac T cell epitopes in cereals: What are they and why do they matter? AOECS Presentation. Helsinki, Finland. Sep. 6, 2012. 26 pages.
Anderson, Future Therapies. University Chicago Presentation. 2011. 60 pages.
Anderson, Genetic susceptibility and regulation of the immune response in celiac disease. DDW Presentation. 2011. 30 pages.
Anderson, Harnessing gluten toxicity to make a drug for coeliac disease. Presentation for The Garvan Institute. Sydney, Australia. 2010. 38 pages.
Anderson, Overcoming gluten toxicity: additions or replacements to diet? ICDS Presentation. Oslo, Norway. Jun. 22, 2011. 49 pages.
Anderson, Sunrise Session: Basic science celiac disease. DDW Presentation. 2011. 29 pages.
Anderson. Coeliac disease is on the rise. Med J Aust. Mar. 21, 2011;194(6):278-9.
Anderson. Coeliac disease: current approach and future prospects. Intern Med J. Oct. 2008;38(10):790-9.
Anderson. Coeliac disease: new tests, new genes and rising prevalence. MedicineToday. Jun. 2011;12(6):69-71.
Anderson. Development of a vaccine for celiac disease. Frontiers in Celiac Disease. 2008;12:172-180.
Anderson., Update in coeliac disease: from food to molecular therapeutics and diagnostics. ASCIA Presentation. 2011. 46 pages.
Arentz-Hansen et al., The intestinal T cell response to alpha-gliadin in adult celiac disease is focused on a single deamidated glutamine targeted by tissue transglutaminase. J Exp Med. Feb. 21, 2000;191(4):603-12.
Arentz-Hansen et al., Celiac lesion T cells recognize epitopes that cluster in regions of gliadins rich in proline residues. Gastroenterology. Sep. 2002;123(3):803-9.
Arentz-Hansen et al., The molecular basis for oat intolerance in patients with celiac disease. PLoS Med. Oct. 2004;1(1):e1. Epub Oct. 19, 2004.
Attwood, Genomics. The Babel of bioinformatics. Science. Oct. 20, 2000;290(5491):471-3. 5 pages.
Avalos et al., Monovalent engagement of the BCR activates ovalbumin-specific transnuclear B cells. J Exp Med. 2014;211(2):365-79.
Bakshi et al., Emerging therapeutic options for celiac disease: potential alternatives to a gluten-free diet. Gastroenterol Hepatol (N Y). Sep. 2012;8(9):582-8.
Bateman et al., IgA antibodies of coeliac disease patients recognise a dominant T cell epitope of A-gliadin. Gut. Sep. 2004;53(9):1274-8.
Beck et al., Abstract W1370: Adherence to a gluten free diet is the main determinant of chemokine expression in celiac disease. Gastroenterol. Jan. 1, 2003;124(4):A657.
Beissbarth et al., A systematic approach for comprehensive T-cell epitope discovery using peptide libraries.Bioinformatics. Jun. 2005;21 Suppl 1:i29-37.
Biagi et al., A non-toxic analogue of a coeliac-activating gliadin peptide: a basis for immunomodulation? Aliment Pharmacol Ther. Jul. 1999;13(7):945-50.
Björck et al., Serum cytokine pattern in young children with screening detected coeliac disease. Clin Exp Immunol. Feb. 2015;179(2):230-5. doi: 10.1111/cei.12454.
Blumenthal et al., "Definition of an Allergen." Allergens and Allergen Immunotherapy. Marcel Decker. "Lockey, Bukantz, and Bousquet." New York. 2004:37-50.
Bodd et al., T-cell response to gluten in patients with HLA-DQ2.2 reveals requirement of peptide-MHC stability in celiac disease. Gastroenterology. Mar. 2012;142(3):552-61. doi: 10.1053/j.gastro. 2011.11.021. Epub Nov. 19, 2011.
Bragde et al., Potential blood-based markers of celiac disease. BMC Gastroenterol. Oct. 9, 2014;14:176. doi: 10.1186/1471-230X-14-176.
Brottveit et al., Absence of somatization in non-coeliac gluten sensitivity. Scand J Gastroenterol. Jul. 2012;47(7):770-7.
Brottveit et al., Assessing possible celiac disease by an HLA-DQ2-gliadin Tetramer Test. Am J Gastroenterol. Jul. 2011;106(7):1318-24. doi: 10.1038/ajg.2011.23. Epub Mar. 1, 2011. Erratum in: Am J Gastroenterol. Apr. 2012;107(4):638.
Brottveit et al., Mucosal cytokine response after short-term gluten challenge in celiac disease and non-celiac gluten sensitivity. Am J Gastroenterol. May 2013;108(5):842-50. doi: 10.1038/ajg.2013.91. Epub Apr. 16, 2013.
Brottveit, Gluten challenge in coeliac disease and non-coeliac gluten sensitivity. Oslo University Hospital. 2012:2-74.
Broughton et al., Biased T Cell Receptor Usage Directed against Human Leukocyte Antigen DQ8-Restricted Gliadin Peptides is Associated with Celiac Disease. Immunity. Oct. 19, 2012;37(4):611-21. Epub Oct. 11, 2012.
Brown et al., A phase I study to determine safety, tolerability and bioactivity of nexvax2 in HLA DQ2+ volunteers with celiac disease following a long-term, strict gluten free diet . AGA Abstracts. 2011; p. S-437-8: Abstract Su1235.
Brown et al., A phase I study to determine safety, tolerability and bioactivity of Nexvax2® in HLA DQ2+ volunteers with celiac disease following a long-term, strict gluten-free diet. Gastroenterology. May 2011;140(5):Suppl1:S437-8. BIOSIS Abstract Accession No. PREV201100403721.
Brown et al., A phase I study to determine safety, tolerability and bioactivity of Nexvax2® in HLA DQ2+ volunteers with celiac disease following long-term, strict gluten-free diet. DDW Presentation. 2011. 6 pages.

(56) References Cited

OTHER PUBLICATIONS

Brown et al., A phase I study to determine safety, tolerability and bioactivity of Nexvax2® in HLA DQ2+ volunteers with celiac disease following long-term, strict gluten-free diet. DDW Poster. 2011. 1 page.

Burton et al. Sequential transcriptional changes dictate safe and effective antigen-specific immunotherapy. Nat Commun. Sep. 3, 2014;5:4741. doi: 10.1038/ncomms5741.

Camarca et al., Short wheat challenge is a reproducible in-vivo assay to detect immune response to gluten. Clin Exp Immunol. Aug. 2012;169(2):129-36.

Camarca et al., Intestinal T cell responses to gluten peptides are largely heterogeneous: implications for a peptide-based therapy in celiac disease. J Immunol. Apr. 1, 2009;182(7):4158-66.

Camarca et al., Intestinal T-cell responses to gluten-derived peptides reveal a large repertoire and a hierarchy of gluten epitopes in adult HLA-DQ2-positive celiac patients. AGA Abstracts. 2006; p. A-94: Abstract 657.

Camarca et al., Intestinal T-cell responses to gluten-derived peptides reveal a large repertoire and a hierarchy of gluten epitopes in adult HLA-DQ2-positive celiac patients. J Pediatric Gastroenterol Nutr. 42.5. 2006:E19.

Campbell et al., Peptide immunotherapy in allergic asthma generates IL-10-dependent immunological tolerance associated with linked epitope suppression. J Exp Med. Jul. 6, 2009;206(7):1535-47. doi: 10.1084/jem.20082901. Epub Jun. 15, 2009.

Cataldo et al., Plasma cytokine profiles in patients with celiac disease and selective IgA deficiency. Pediatr Allergy Immunol. Aug. 2003;14(4):320-4.

Catassi et al. (eds), Primary Prevention for Coeliac Disease the Utopia of the New Millennium? vol. I: Perspectives on Coeliac Disease. Proceedings of the Meeting on Coeliac Disease held in Pavia on Oct. 12, 2001. Published in 2003. AIC Press. Italian Coeliac Society. Pisa, Italy. pp. 1-112.

Catassi et al., A prospective, double-blind, placebo-controlled trial to establish a safe gluten threshold for patients with celiac disease. Am J Clin Nutr. Jan. 2007;85(1):160-6.

Catassi et al., World Perspective on Celiac Disease. J Pediatr Gastroenterol Nutr. Nov. 2012;55(5):494-499.

Cheng et al., CD4+, but not CD8+, T cells from mammary tumor-bearing mice have a down-regulated production of IFN-gamma: role of phosphatidyl serine. J Immunol. Mar. 15, 1998;160(6):2735-41.

Chowers et al., Increased proinflammatory cytokine gene expression in the colonic mucosa of coeliac disease patients in the early period after gluten challenge. Clin Exp Immunol. Jan. 1997;107(1):141-7.

Cornell et al., Characterization of the gliadin-derived peptides which are biologically active in coeliac disease. Clin Chim Acta. Dec. 31, 1992;213(1-3):37-50.

Cornell et al., In vitro mucosal digestion of synthetic gliadin-derived peptides in celiac disease. J Protein Chem. Jul. 1995;14(5):335-9.

Cornell et al., Studies of in vitro gamma-interferon production in coeliac disease as a response to gliadin peptides. Biochim Biophys Acta. May 25, 1994;1226(2):126-30. Abstract only.

Costa et al., A population study to optimize the role of serology and genetics in the diagnosis of celiac disease (CD). DDW Poster. 2011. 1 page.

Costa et al., A population study to optimize the role of serology and genetics in the diagnosis of celiac disease . AGA Abstracts. 2011; p. S-440: Abstract Su1246.

Costa et al., Quantifying community need and potential impact of rational testing for Coeliac Disease: A basis for disciplinary guidelines in Australia. Presentation. St. Georges, Sydney, Australia. 2011. 34 pages.

Daveson et al., Small bowel endoscopy and coeliac disease. Best Pract Res Clin Gastroenterol. Jun. 2012;26(3):315-23.

Daveson et al., Effect of hookworm infection on wheat challenge in celiac disease—a randomised double-blinded placebo controlled trial. PLoS One. Mar. 8, 2011;6(3):1-9.

De Kauwe et al., Resistance to celiac disease in humanized HLA-DR3-DQ2-transgenic mice expressing specific anti-gliadin CD4+ T cells. J Immunol. Jun. 15, 2009;182(12):7440-50. Doi: 10.4049/jimmunol.0900233.

Dioszeghy et al., Epicutaneous immunotherapy results in rapid allergen uptake by dendritic cells through intact skin and downregulates the allergen-specific response in sensitized mice. J Immunol. May 15, 2011;186(10):5629-37. doi: 10.4049/jimmunol.1003134. Epupb Apr. 13, 2011.

Dioszeghy et al., The regulatory T cells induction by epicutaneous immunotherapy is sustained and mediates long-term protection from eosinophilic disorders in peanut-sensitized mice. Clin Exp Allergy. Jun. 2014;44(6):867-81. doi: 10.1111/cea.12312.

Erickson, 10 Promising Therapeutic Vaccines. Fierce Vaccines. Oct. 27, 2011. Last Accessed on Nov. 13, 2012 from http://www.fiercevaccines.com/story/10-promising-therapeutic-vaccines/2011-10-27.

Fellrath et al., Allergen-specific T-cell tolerance induction with allergen-derived long synthetic peptides: results of a phase I trial. J Allergy Clin Immunol. Apr. 2003;111(4):854-61.

Fleckenstein et al., Gliadin T cell epitope selection by tissue transglutaminase in celiac disease. Role of enzyme specificity and pH influence on the transamidation versus deamidation process. J Biol Chem. Sep. 13, 2002;277(37):34109-16. Epub Jul. 1, 2002.

Fornari et al., Pre- and post-treatment serum levels of cytokines IL-1beta, IL-6, and IL-1 receptor antagonist in celiac disease. Are they related to the associated osteopenia? Am J Gastroenterol. Mar. 1998;93(3):413-8.

Forster, Interferon signatures in immune disorders and disease. Immunol Cell Biol. May 2012;90(5):520-7.

Fraser et al., Coeliac disease: in vivo toxicity of the putative immunodominant epitope. Gut. Dec. 2003;52(12):1698-702.

Friedl-Hajek et al., Identification of a highly promiscuous and an HLA allele-specific T-cell epitope in the birch major allergen Bet v 1: HLA restriction, epitope mapping and TCR sequence comparisons. Clin Exp Allergy. Apr. 1999;29(4):478-87.

Genbank Submission; NIH/NCBI, Accession No. AAB28161;Sainova et al.; Jan. 19, 1994. 1 page.

Genbank Submission; NIH/NCBI, Accession No. AAZ76368.1; Han et al.; Mar. 20, 2008 . . . 1 page.

Genbank Submission; NIH/NCBI, Accession No. ABS72146; Chen et al.; Aug. 5, 2007. 1 page.

Goldman, Best thing since sliced bread? A (potential) new diagnostic for celiac disease. Scope. Stanford Medicine. Jun. 22, 2013. http://scopeblog.stanford.edu/2013/07/22/best-thing-since-sliced-bread-a-potential-new-diagnostic-for-celiac-disease/ [last accessed Nov. 19, 2013].

Hagan, The vaccine that means coeliacs can eat wheat. Good Health. Tuesday, Oct. 9, 2012. 1 pg.

Haines et al., Systematic review: The evidence base for long-term management of coeliac disease. Aliment Pharmacol Ther. Nov. 1, 2008;28(9):1042-66. Epub Jul. 30, 2008.

Hall et al., Precise probes of type II interferon activity define the origin of interferon signatures in target tissues in rheumatic diseases. Proc Natl Acad Sci U S A. Oct. 23, 2012;109(43):17609-14.

Han et al., Dietary gluten triggers concomitant activation of CD4+ and CD8+ αβ T cells and γδ T cells in celiac disease. Proc Natl Acad Sci U S A. Aug. 6, 2013;110(32):13073-8.

Hardy et al., Ingestion of oats and barley in patients with celiac disease mobilizes cross-reactive T cells activated by avenin peptides and immuno-dominant hordein peptides, Journal of Autoimmunity (2014), http://dx.doi.org/10.1016/j.jaut.2014.10.003. Article in press.

Henderson et al., A structural and immunological basis for the role of human leukocyte antigen DQ8 in celiac disease. Immunity. Jul. 2007;27:23. doi:10.1016/j.immuni.2007.05.015. 12 pages.

Henderson et al., Supplemental Data: A structural and immunological basis for the role of human leukocyte antigen DQ8 in celiac disease. Immunity. Jul. 2007;27:1-9.

Henderson et al., The production and crystallization of the human leukocyte antigen class II molecules HLA-DQ2 and HLA-DQ8

(56) References Cited

OTHER PUBLICATIONS complexed with deamidated gliadin peptides implicated in coeliac disease. Acta Crystallogr Sect F Struct Biol Cryst Commun. Dec. 1, 2007;63(Pt 12):1021-5. Epub Nov. 21, 2007.
Hirahara et al., New specific immunotherapies for Japanese cedar pollinosis. Biolog Eng. 2002;80(4): 152-55.
Hoyne et al., Regulation of house dust mite responses by intranasally administered peptide: transient activation of CD4+ T cells precedes the development of tolerance in vivo. Int Immunol. Mar. 1996;8(3):335-42.
Huan et al., Single-chain recombinant HLA-DQ2.5/peptide molecules block α2-gliadin-specific pathogenic CD4+ T-cell proliferation and attenuate production of inflammatory cytokines: a potential therapy for celiac disease. Mucosal Immunol. Jan. 2011;4(1):112-20. Epub Aug. 25, 2010.
Keech et al., Immune tolerance induced by peptide immunotherapy in an HLA Dq2-dependent mouse model of gluten immunity. Gastroenterology May 2009;136(5):A57. Abstract 355.
Kilmartin et al., Abstract 2026 Immune responses to gliadin but not to avenin in organ culture studies of coeliac biopsies. Gastronenterol. Jan. 1, 2001:A396.
Kinnunen et al., Potential of an altered peptide ligand of lipocalin allergen Bos d 2 for peptide immunotherapy. J Allergy Clin Immunol. Apr. 2007;119(4):965-72. Epub Mar. 1, 2007.
Kooy-Winkelaar et al., Gluten-specific T cells cross-react between HLA-DQ8 and the HLA-DQ2α/DQ8β transdimer. J Immunol. Nov. 15, 2011;187(10):5123-9. doi: 10.4049/jimmunol.1101179. Epub Oct. 17, 2011.
Lammi et al., Increased peripheral blood CD4+ T cell responses to deamidated but not to native gliadin in children with coeliac disease. Clin Exp Immunol. May 2012;168(2):207-14. doi: 10.1111/j.1365-2249.2012.04575.x.
Liu et al., Exploring T cell reactivity to gliadin in young children with newly diagnosed celiac disease. Autoimmune Dis. 2014;2014:927190. doi:10.1155/2014/927190. Epub Mar. 3, 2014.
Maguire et al., The safety and efficacy of ALLERVAX CAT in cat allergic patients. Clin Immunol. Dec. 1999;93(3):222-31.
Marylia et al., A population study to optimize the role of serology and genetics in the diagnosis of celiac disease (CD). DDW Poster. 2011. 1 page.
McAllister et al., The immunonathogenesis of celiac disease reveals possible therapies beyond the gluten-free diet. Semin Immunopathol. Jul. 2012;34(4):581-600. doi: 10.1007/s00281-012-0318-8. Epub Jun. 7, 2012.
McSorley et al., Suppression of inflammatory immune responses in celiac disease by experimental hookworm infection. PLoS One. 2011;6(9):1-7. Epub Sep. 16, 2011.
Molberg et al., Tissue transglutaminase selectively modifies gliadin peptides that are recognized by gut-derived T cells in celiac disease. Nat Med. Jun. 1998;4(6):713-7.
Molberg et al., T cells from celiac disease lesions recognize gliadin epitopes deamidated in situ by endogenous tissue transglutaminase. Eur J Immunol. May 2001;31(5):1317-23.
Mondoulet et al., Epicutaneous immunotherapy (EPIT) blocks the allergic esophago-gastro-enteropathy induced by sustained oral exposure to peanuts in sensitized mice. PLoS One. 2012;7(2):e31967. doi: 10.1371/journal.pone.0031967. Epub Feb. 21, 2012.
Mondoulet et al., Intact skin and not stripped skin is crucial for the safety and efficacy of peanut epicutaneous immunotherapy (EPIT) in mice. Clin Transl Allergy. Nov. 12, 2012;2(1):22. doi: 10.1186/2045-7022-2-22.
Mondoulet et al.,. Specific epicutaneous immunotherapy prevents sensitization to new allergens in a murine model. J Allergy Clin Immunol. Jun. 2015;135(6):1546-57.e4. doi: 10.1016/j.jaci.2014.11.028. Epub Jan. 9, 2015.
Müller et al., Successful immunotherapy with T-cell epitope peptides of bee venom phospholipase A2 induces specific T-cell anergy in patients allergic to bee venom. J Allergy Clin Immunol. Jun. 1998;101(6 Pt 1):747-54.

Murray et al., HLA DQ Gene Dosage and Risk and Severity of Celiac Disease. Clin Gastroenterol Hepatol. Dec. 2007; 5(12): 1406-1412.
Ngo et al., Computational Complexity, Protein Structure Prediction, and the Levinthal Paradox. The Protein Folding Problem and tertiary Structure Prediction. Merz et al., Eds. 1994:14,492-5.
Norman et al., Treatment of cat allergy with T-cell reactive peptides. Am J Respir Crit Care Med. Dec. 1996;154(6 Pt 1):1623-8.
Oberhuber et al., The histopathology of coeliac disease: time for a standardized report scheme for pathologists. Eur J Gastroenterol Hepatol. Oct. 1999;11(10):1185-94. Review.
Oldfield et al., Effect of T-cell peptides derived from Fel d 1 on allergic reactions and cytokine production in patients sensitive to cats: a randomised controlled trial. Lancet. Jul. 6, 2002;360(9326):47-53.
Ontiveros et al., A whole blood cytokine release assay employing short-term gluten challenge identifies patients with celiac disease on a gluten free diet . AGA Abstracts. 2012; p. S-271: Abstract Sa1317.
Ontiveros et al., A whole blood cytokine release assay employing short-term gluten challenge identifies patients with celiac disease on a gluten free diet. DDW ePoster. And Poster. 2012. 1 page.
Ontiveros et al., A whole blood cytokine release assay employing short-term gluten challenge identifies patients with celiac disease on a gluten free diet. DDW ePoster. And Poster. 2012. 9 pages.
Ontiveros et al., Ex-vivo whole blood secretion of interferon (IFN)-γ and IFN-γ-inducible protein-10 measured by enzyme-linked immunosorbent assay are as sensitive as IFN-γ enzyme-linked immunospot for the detection of gluten-reactive T cells in human leucocyte antigen (HLA)-DQ2•5(+)-associated coeliac disease. Clin Exp Immunol. Feb. 2014;175(2):305-15. doi: 10.1111/cei.12232.
Osman et al., B cell epitopes of gliadin. Clin Exp Immunol. Aug. 2000;121(2):248-54.
Paterson et al., The safety, tolerance, pharmacokinetic and pharmacodynamic effects of single doses of AT-1001 in coeliac disease subjects: a proof of concept study. Aliment Pharmacol Ther. Sep. 1, 2007;26(5):757-66.
Pincus, Coeliac vaccine trials world first. 12 Weekend Professional Health. The Weekend Australian. Mar. 21-22, 2009. 1 page.
Potkin et al., Wheat gluten challenge in schizophrenic patients. Am J Psychiatry. Sep. 1981;138(9):1208-11.
Przemioslo et al., Raised pro-inflammatory cytokines interleukin 6 and tumour necrosis factor alpha in coeliac disease mucosa detected by immunohistochemistry. Gut. Oct. 1994;35(10):1398-403.
Qiao et al., Refining the rules of gliadin T cell epitope binding to the disease-associated DQ2 molecule in celiac disease: importance of proline spacing and glutamine deamidation. J Immunol. Jul. 1, 2005;175(1):254-61.
Quarsten et al., Staining of celiac disease-relevant T cells by peptide-DQ2 multimers. J Immunol. Nov. 1, 2001;167(9):4861-8.
Raki et al., Tetramer visualization of gut-homing gluten-specific T cells in the peripheral blood of celiac disease patients. Proc Natl Acad Sci U S A. Feb. 20, 2007;104(8):2831-6. Epub Feb. 16, 2007.
Romaldini et al., Serum soluble interleukin-2 receptor, interleukin-6, and tumor necrosis factor-alpha levels in children with celiac disease: response to treatment. J Pediatr Gastroenterol Nutr. Oct. 2002;35(4):513-7.
Rönnblom et al., The interferon signature in autoimmune diseases. Curr Opin Rheumatol. Mar. 2013;25(2):248-53.
Rossi et al., Intravenous or intranasal administration of gliadin is able to down-regulate the specific immune response in mice. Scand J Immunol. Aug. 1999;50(2):177-82.
Rubio-Tapia et al., ACG clinical guidelines: diagnosis and management of celiac disease. Am J Gastroenterol. May 2013;108(5):656-76.
Saito, New Immunotherapy—Peptide therapy & DNA vaccine therapy. Clinical of Allergy. Nov. 2003; 23(12):26-30.
Saxby et al., A study of IgA antibodies to a T cell epitope of α-gliadin in coeliac disease. British Soc Immunol Poster. 2002. 1 page.
Schein et al., Bioinformatics approaches to classifying allergens and predicting cross-reactivity. Immunol Allergy Clin North Am. Feb. 2007;27(1):1-27.

(56) References Cited

OTHER PUBLICATIONS

Scibilia et al., Wheat allergy: a double-blind, placebo-controlled study in adults. J Allergy Clin Immunol. Feb. 2006;117(2):433-9.
Shan et al., Identification and analysis of multivalent proteolytically resistant peptides from gluten: implications for celiac sprue. J Proteome Res. Sep.-Oct. 2005;4(5):1732-41.
Sjöström et al., Identification of a gliadin T-cell epitope in coeliac disease: general importance of gliadin deamidation for intestinal T-cell recognition. Scand J Immunol. Aug. 1998;48(2):111-5.
Skerritt et al., Antigenecity of wheat prloamins: detailed epitope analysis using a panel of monoclonal antibodies. J Cereal Sci. 2000;32:259-79.
Skolnick et al., From genes to protein structure and function: novel applications of computational approaches in the genomic era. Trends Biotechnol. Jan. 2000;18(1):34-9.
Sollid et al., Nomenclature and listing of celiac disease relevant gluten T-cell epitopes restricted by HLA-DQ molecules. Immunogenetics. Jun. 2012;64(6):455-60. doi: 10.1007/s00251-012-0599-z. Epub Feb. 10, 2012.
Stewart et al., Dominance, hierarchy and redundancy of T cell stimulatory peptides in celiac disease. AGA Abstracts. 2009; p. A-57: Abstract 354.
Tan et al., Non-axial bone fracture but not depression as a risk factor for coeliac disease. Intern Med J. Mar. 2010;40(3):225-7.
Tanner et al., Dissecting the T-cell response to hordeins in coeliac disease can develop barley with reduced immunotoxicity. Aliment Pharmacol Ther. Nov. 2010;32(9):1184-91. Epub Sep. 15, 2010.
Tarlac et al., HLA-DR3-DQ2 Mice Do Not Develop Ataxia in the Presence of High Titre Anti-gliadin Antibodies. Cerebellum. Oct. 20, 2012.
Tjon et al., Celiac disease: how complicated can it get? Immunogenetics. Oct. 2010;62(10):641-51. doi: 10.1007/s00251-010-0465-9. Epub Jul. 27, 2010. Review.
Tollefsen et al., HLA-DQ2 and -DQ8 signatures of gluten T cell epitopes in celiac disease. J Clin Invest. Aug. 2006;116(8):2226-36.
Tye-Din et al., A 35mer peptide with T cell stimulatory activity comparable to whole gliadin: a lead compound for peptide immunotherapy in celiac disease. AGA Abstracts. 2006; p. A-95: Abstract 661.
Tye-Din et al., A comprehensive bioinformatic and functional screen of wheat gluten T-cell epitopes in HLA-DQ2 celiac disease in vivo. AGA Abstracts. 2005; p. A-2: Abstract 13.
Tye-Din et al., A third celiac disease: genotyping reveals a functionally distinct subtype. AGA Abstracts. 2006; p. A-664: Abstract W1238.
Tye-Din et al., Comprehensive T-cell epitope characterization in HLA-DQ8 celiac disease. AGA Abstracts. 2005; p. A-2: Abstract 14.
Tye-Din et al., Comprehensive, quantitative mapping of T cell epitopes in gluten in celiac disease. Sci Transl Med. Jul. 21, 2010;2(41):1-14.
Tye-Din et al., HLA-DQ genotype reverses incorrect diagnosis of celiac disease. AGA Abstracts. 2005; p. A-259: Abstract S1805.
Tye-Din et al., Immunopathogenesis of celiac disease. CurrGastroenterol Rep. Oct. 2008;10(5):458-65.
Tye-Din et al., Oats induce avenin specific T-cells in celiac disease. AGA Abstracts. 2005; p. A-259: Abstract S1804.
Tye-Din et al., Supplementary Materials for Comprehensive, quantitative mapping of T cell epitopes in gluten in celiac disease. Sci Transl Med. Jul. 21, 2010;2(41):41ra51.
Tye-Din et al., T-cell epitope hierarchy after rye and barley ingestion in celiac disease. AGA Abstracts. 2005; p. A-259: Abstract S1803.
Tye-Din et al., The effects of ALV003 pre-digestion of gluten on immune response and symptoms in celiac disease in vivo. Clin Immunol. Mar. 2009;134(3):1-7.
Tye-Din et al., Universal and grain-specific T cell epitopes in celiac disease. AGA Abstracts. 2007; p. A-108: Abstract 760.
Vader et al., Characterization of cereal toxicity for celiac disease patients based on protein homology in grains. Gastroenterology. Oct. 2003;125(4):1105-13.
Vader et al., Specificity of tissue transglutaminase explains cereal toxicity in celiac disease. J Exp Med. Mar. 4, 2002;195(5):643-9.
Vader et al., The gluten response in children with celiac disease is directed toward multiple gliadin and glutenin peptides. Gastroenterology. Jun. 2002;122(7):1729-37.
Van De Wal et al., Glutenin is involved in the gluten-driven mucosal T cell response. Eur J Immunol. Oct. 1999;29(10):3133-9.
Van De Wal et al., Selective deamidation by tissue transglutaminase strongly enhances gliadin-specific T cell reactivity. J Immunol. Aug. 15, 1998;161(4):1585-8.
Van De Wal et al., Small intestinal T cells of celiac disease patients recognize a natural pepsin fragment of gliadin. Proc Natl Acad Sci U S A. Aug. 18, 1998;95(17):10050-4.
Verginis et al., Induction of antigen-specific regulatory T cells in wild-type mice: visualization and targets of suppression. Proc Natl Acad Sci U S A. Mar. 4, 2008;105(9):3479-84. doi: 10.1073/pnas.0800149105. Epub Feb. 25, 2008.
Vives-Pi et al., Biomarkers for diagnosis and monitoring of celiac disease. J Clin Gastroenterol. Apr. 2013;47(4):308-13. doi: 10.1097/MCG.0b013e31827874e3. Review.
Walker-Smith et al., Revised criteria for diagnosis of coeliac disease. Report of Working Group of European Society of Paediatric Gastroenterology and Nutrition. Arch Dis Child. Aug. 1990;65(8):909-11.
Xia et al., Inhibition of HLA-DQ2-mediated antigen presentation by analogues of a high affinity 33-residue peptide from alpha2-gliadin. J Am Chem Soc. Feb. 15, 2006;128(6):1859-67.
Barratt et al., Factors influencing the type, timing and severity of symptomatic responses to dietary gluten in patients with biopsy-proven coeliac disease. J Gastrointestin Liver Dis. Dec. 2013;22(4):391-6.
Crabtree et al., Serum interleukin-2-receptor in coeliac disease: response to treatment and gluten challenge. Clin Exp Immunol. Sep. 1989;77(3):345-8.
Goel et al., Epitope-specific immunotherapy targeting CD4-positive T cells in coeliac disease: two randomised, double-blind, placebo-controlled phase 1 studies. Lancet Gastroenterol Hepatol. Jul. 2017;2(7):479-493. doi: 10.1016/S2468-1253(17)30110-3. Epub May 11, 2017.
Penedo-Pita et al., Increased serum levels of interleukin-2 and soluble interleukin-2 receptor in celiac disease. J Pediatr Gastroenterol Nutr. Jan. 1991;12(1):56-60.
Silvester et al., Symptomatic suspected gluten exposure is common among patients with coeliac disease on a gluten-free diet. Aliment Pharmacol Ther. Sep. 2016;44(6):612-9. doi: 10.1111/apt.13725. Epub Jul. 22, 2016.
U.S. Appl. No. 14/776,235, filed Sep. 14, 2015, Anderson et al.

* cited by examiner

| HLA-DQ Status* | Homozygous 2.5 | 2.5/2.2 or 2.5/7 | Heterozygous 2.5 | 2.5/unknown |
|---|---|---|---|---|
| Functional HLA-DQ2.5 dose | Higher | Intermediate | Lower | ND |
|  | # Subjects | # Subjects | # Subjects | # Subjects |
| Cohort 1 – Oral challenge + gluten peptide composition 150 mcg | 3 | 0 | 3 | 2 |
| Cohort 2 – Oral challenge + gluten peptide composition 300 mcg | 1 | 3 | 5 | 1 |
| Cohort 7 – Biopsy + + gluten peptide composition 150 mcg | 2 | 1 | 4 | 0 |
| Cohort 1&2 – Placebo | 0 | 2 | 5 | 0 |
| Cohort 7 – Placebo | 0 | 3 | 4 | 0 |
| Total Subjects | 6 | 9 | 21 | 3 |
| % Total receiving gluten peptide composition | 6/6 | 4/9 | 12/21 | 3/3 |

*One HLA-DQA and one DQB gene is present on each chromosome. If both HLA-DQA genes are DQA1*05 and both DQB genes are DQB1*02 this is homozygosity for HLA-DQ2.5. If only one DQA is DQA1*05 and one is DQB1*02 this is heterozygosity for DQ2.5 Since DQ2.2 is encoded by HLA-DQA1*02 and DQB1*02, and DQ7 by HLA-DQA1*05 and DQB1*0301, these combinations encode homozygosity for DQA1*05 or DQB1*02

FIG. 1

HLA-DQ2.5 Homozygotes* vs Other Subjects

| | IFN | IP-10 | IL-2 | IL-6 | IL-8 | IL-10 | MCP-1 | TNF | Sx |
|---|---|---|---|---|---|---|---|---|---|
| Cohort 1 | | | | | | | | | |
| homozygous (3) | 2 | 4.8 | 49.6 | 12.9 | 49.7 | 15.5 | 30.4 | 7.4 | 2.7 |
| other (5) | 2.5 | 4.2 | 10.9 | 4 | 19.6 | 7.3 | 9.2 | 3.5 | 2.7 |
| Cohort 2 | | | | | | | | | |
| homozygous (1) | 1 | 1 | 22.6 | 1.3 | 4.5 | 1.1 | 2.3 | 2.4 | 4.67 |
| other (9) | 1.4 | 3.7 | 1.6 | 2.3 | 3.4 | 1.6 | 3.6 | 1.6 | 1.8 |
| Cohort 7 | | | | | | | | | |
| homozygous (2) | 1.3 | 4.1 | 8.2 | 6.4 | 7.7 | 4.6 | 8.1 | 2.4 | 1.67 |
| other (5) | 1.4 | 1.5 | 1.33 | 1.8 | 3.4 | 1.2 | 3.8 | 1.3 | 1.4 |

*One HLA-DQA and one DQB gene is present on each chromosome. If both HLA-DQA genes are DQA1*05 and both DQB genes are DQB1*02 this is homozygosity for HLA-DQ2.5

** Average daily symptom diary score across 7 parameters from the GSRS

SEQUENCE LISTING

<160> NUMBER OF SEQ ID NOS: 85

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

Pro Phe Pro Gln Pro Glu Leu Pro Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Pro Gln Pro Glu Leu Pro Tyr Pro Gln
1               5

-continued

```
<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 3

Pro Phe Pro Gln Pro Glu Gln Pro Phe
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 4

Pro Gln Pro Glu Gln Pro Phe Pro Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Pro Ile Pro Glu Gln Pro Gln Pro Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Glu Gln Pro Ile Pro Glu Gln Pro Gln
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 7

Gln Pro Phe Pro Gln Pro Glu Gln Pro Phe Pro Trp Gln Pro
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 8

Pro Glu Gln Pro Ile Pro Glu Gln Pro Gln Pro Tyr Pro Gln Gln
1               5                   10                  15

<210> SEQ ID NO 9
```

```
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 9

Glu Leu Gln Pro Phe Pro Gln Pro Glu Leu Pro Tyr Pro Gln Pro Gln
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 10

Glu Gln Pro Phe Pro Gln Pro Glu Gln Pro Phe Pro Trp Gln Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 11

Glu Pro Glu Gln Pro Ile Pro Glu Gln Pro Gln Pro Tyr Pro Gln Gln
1               5                   10                  15

<210> SEQ ID NO 12
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 12

Pro Glu Leu Pro
1

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Pro Glu Leu Pro Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Pro Tyr Pro Gln Pro Glu Leu Pro Tyr
1               5

<210> SEQ ID NO 15
<211> LENGTH: 9
```

```
<212> TYPE: PRT
<213> ORGANISM: Artificial Sequence
<220> FEATURE:
<223> OTHER INFORMATION: Synthetic Polypeptide

<400> SEQUENCE: 15

Pro Phe Pro Gln Pro Gln Leu Pro Tyr
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 16

Pro Gln Leu Pro
1

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Pro Gln Leu Pro Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Pro Tyr Pro Gln Pro Gln Leu Pro Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 19

Pro Gln Pro Gln Leu Pro Tyr Pro Gln
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 20

Pro Phe Pro Gln Pro Gln Gln Pro Phe
1               5

<210> SEQ ID NO 21
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 21

Pro Gln Pro Gln Gln Pro Phe Pro Trp
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 22

Pro Ile Pro Gln Gln Pro Gln Pro Tyr
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 23

Leu Gln Pro Phe Pro Gln Pro Gln Leu Pro Tyr Pro Gln Pro Gln
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 24

Gln Pro Phe Pro Gln Pro Gln Gln Pro Phe Pro Trp Gln Pro
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 25

Pro Glu Gln Pro Ile Pro Gln Gln Pro Gln Pro Tyr Pro Gln Gln
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 26

Pro Phe Pro Gln Pro Asp Leu Pro Tyr
1               5

<210> SEQ ID NO 27
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 27

Phe Arg Pro Glu Gln Pro Tyr Pro Gln
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 28

Pro Gln Gln Ser Phe Pro Glu Gln Gln
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 29

Ile Gln Pro Glu Gln Pro Ala Gln Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 30

Gln Gln Pro Glu Gln Pro Tyr Pro Gln
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 31

Ser Gln Pro Glu Gln Glu Phe Pro Gln
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Pro Gln Pro Glu Gln Glu Phe Pro Gln
1               5

<210> SEQ ID NO 33
<211> LENGTH: 9
<212> TYPE: PRT
<213> ORGANISM: Artificial Sequence
<220> FEATURE:
```

<223> OTHER INFORMATION: Synthetic Polypeptide

<400> SEQUENCE: 33

Gln Gln Pro Glu Gln Pro Phe Pro Gln
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 34

Pro Gln Pro Glu Gln Pro Phe Cys Gln
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 35

Gln Gln Pro Phe Pro Glu Gln Pro Gln
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 36

Pro Phe Ser Glu Gln Glu Gln Pro Val
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 37

Phe Ser Gln Gln Gln Glu Ser Pro Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 38

Pro Gln Pro Glu Gln Pro Phe Pro Gln
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 39

Pro Tyr Pro Glu Gln Glu Glu Pro Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 40

Pro Tyr Pro Glu Gln Glu Gln Pro Phe
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 41

Glu Gly Ser Phe Gln Pro Ser Gln Glu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Glu Gln Pro Gln Gln Pro Phe Pro Gln
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

Glu Gln Pro Gln Gln Pro Tyr Pro Glu
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 44

Gln Gln Gly Tyr Tyr Pro Thr Ser Pro Gln
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 45

Pro Gln Gln Ser Phe Pro Glu Gln Glu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 46

Gln Gly Tyr Tyr Pro Thr Ser Pro Gln
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 47

Phe Arg Pro Gln Gln Pro Tyr Pro Gln
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 48

Pro Gln Gln Ser Phe Pro Gln Gln Gln
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

Ile Gln Pro Gln Gln Pro Ala Gln Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 50

Gln Gln Pro Gln Gln Pro Tyr Pro Gln
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 51

```
Ser Gln Pro Gln Gln Gln Phe Pro Gln
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Pro Gln Pro Gln Gln Gln Phe Pro Gln
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Gln Gln Pro Gln Gln Pro Phe Pro Gln
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 54

Pro Gln Pro Gln Gln Pro Phe Cys Gln
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 55

Gln Gln Pro Phe Pro Gln Gln Pro Gln
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 56

Pro Phe Ser Gln Gln Gln Gln Pro Val
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 57
```

```
Phe Ser Gln Gln Gln Gln Ser Pro Phe
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

```
Pro Gln Pro Gln Gln Pro Phe Pro Gln
1               5
```

<210> SEQ ID NO 59
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 59

```
Pro Tyr Pro Glu Gln Gln Glu Pro Phe
1               5
```

<210> SEQ ID NO 60
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 60

```
Pro Tyr Pro Glu Gln Gln Gln Pro Phe
1               5
```

<210> SEQ ID NO 61
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 61

```
Gln Gly Ser Phe Gln Pro Ser Gln Gln
1               5
```

<210> SEQ ID NO 62
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 62

```
Leu Gln Pro Phe Pro Gln Pro Glu Leu Pro Tyr Pro Gln Pro Gln
1               5                   10                  15
```

<210> SEQ ID NO 63
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 63

```
Pro Gln Gln Pro Ile Pro Gln Gln Pro Gln Pro Tyr Pro Gln Gln
```

<210> SEQ ID NO 64
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 64

Gln Pro Glu Leu Pro Tyr Pro
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 65

Pro Gln Pro Glu Leu Pro Tyr
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 66

Phe Pro Gln Pro Glu Leu Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 67

Pro Glu Leu Pro Tyr Pro Gln
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 68

Phe Pro Gln Pro Glu Leu Pro Tyr Pro
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 69

Pro Gln Pro Asp Leu Pro Tyr Pro Gln
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 70

Pro Phe Pro Gln Pro Asp Gln Pro Phe
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 71

Pro Gln Pro Asp Gln Pro Phe Pro Trp
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 72

Pro Ile Pro Asp Gln Pro Gln Pro Tyr
1               5

<210> SEQ ID NO 73
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 73

Leu Gln Pro Phe Pro Gln Pro Asp Leu Pro Tyr Pro Gln Pro Gln
1               5                   10                  15

<210> SEQ ID NO 74
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 74

Gln Pro Phe Pro Gln Pro Asp Gln Pro Phe Pro Trp Gln Pro
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 75

Pro Gln Gln Pro Ile Pro Asp Gln Pro Gln Pro Tyr Pro Gln Gln
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 76

Gln Pro Gln Leu Pro Tyr Pro
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 77

Pro Gln Pro Gln Leu Pro Tyr
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 78

Phe Pro Gln Pro Gln Leu Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 79

Pro Gln Leu Pro Tyr Pro Gln
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 80

Phe Pro Gln Pro Gln Leu Pro Tyr Pro
1               5

<210> SEQ ID NO 81
<211> LENGTH: 1138
<212> TYPE: DNA
<213> ORGANISM: Homo sapiens

<400> SEQUENCE: 81
ggcctgcgtt cagttggtgc ttccagacac caagggccct tgtgaatccc atcctggaat      60
ggaaggtaag attgagattt gttagagctg aatccgcagt atgagaggaa ggaaagtgga     120
ggaggctgtg gacatgaatg gttgaaagtt gtaggggaat tgggaagtgg catgatgatg     180

```
acataggagc ggcctaggac ccatccatct catgtctgtc ctgttgcagg tgcatcgcca      240
tctacaggag cagaagagtg gacttgctac atgacctagc attattttct ggccccattt      300
atcatatccc ttttctcctc caaatgtttc tcctctcacc tcttctgtgg gacttaaatt      360
gctatatctg ctcagagctc acaaatgcct ttgaattatt tccctgactt cctgattttt      420
ttcttcttaa gtgttaccta ctaagagttg cctggagtaa gccacccagc tacctaattc      480
ctcagtaacc tccatctata atctccatgg aagcaacaaa ttcccttttat gagatatatg      540 tcaaattttt ccatctttca tccagggctg actgaaaccg tggctaagaa ttgggagact      600
ctcttgtttc aagccaattt aacatcattt accagatcat tgtcatgtc cagtaacaca       660 gaagcaacca actacagtat agcctgataa catgttgatt tcttagctga cattaatatt      720
tctttcttcc ttgtgttccc acccttggca ttgccaccca ccctcaatt aaggcaacaa       780 tgaagttaat ggatacccte tgcctttggc tcagaaatgt tatagcaaaa atttaaaat      840 aaaaagtaa gtctgtacta atttcaatat gactttaaa agtatgacag agaaatgggt       900
tgggataaag gaaatttgaa tctcaaaaat atcaatagta aaagttatt ctcaaaactt       960 taaatttgtg aagaatgatg acagtagaag ccttcctctc ccctcctcac cctgaaggaa     1020 taaaattttcc ttaggcagga aaagaaatgg aagtcagaaa acattagaa taagacaata     1080 atgtgggtat ctgaaaagga acaaatactc attcctcaca taggggttagt gacaatgg     1138
```

<210> SEQ ID NO 82
<211> LENGTH: 2414
<212> TYPE: DNA
<213> ORGANISM: Homo sapiens
<220> FEATURE:
<221> NAME/KEY: misc_feature
<222> LOCATION: (1403)..(1502)
<223> OTHER INFORMATION: n is a, c, g, or t

<400> SEQUENCE: 82

```
ccagtcctga gaggaaagaa aatacaatca gtttgttatt aactgaggaa agaattaagt       60
gaaagatgaa tcttaggaag cagaaggaag taaacctaat ctctgactaa gaaagctaaa     120
taccataata actcattcat tccttctttt gtttaattac attatttaat cataagtccg     180
tgatgtgcca ggcactcagg aaatagtaaa aactggacat gtgatattct gcccttgtgt     240
agcgcacatt atagtgggaa agaaagcgca atttaaccg gacaactacc aacaataaga     300
gcggaggaag caggggttgg aaatgtccac aggctgtgcc aaagatgaag cccgtaatat     360
ttgaaagtca gtttctttca tcattttgtg tattaaggtt cttcttccc ctgttctcca     420 ccttcctgct tgtcatcttc actcatcagc tgaccacgtc gcctcttatg gtgtaaactt     480
gtaccagtct tacggtccct ctggccagta cacccatgaa tttgatggag atgagcagtt     540
ctacgtggac ctggggagga aggagactgt ctggtgtttg cctgttctca gacaatttag     600
atttgacccg caatttgcac tgacaaacat cgctgtccta aaacataact tgaacagtct     660
gattaaacgc tccaactcta ccgctgctac caatggtatg tgtcaacaat tctgcccctc     720
tttactgatt tatcccttca taccaagttt cattattttta tttccaagag gtccccagat     780
cttctcatgg caattgctga aattttatca tctcccatct ctaaaatcac atattcccat     840
gtaatacaag ggtctttcca ttatccattc attaaatcct tctcggagag gtctcatcaa     900
cctcctactt tattaaacat gcccacagag agaagggcac aggaataaag cggaggcaat     960
gtgtcgttgc tccaagcag aaggtaaata agacctcttt gactatcagg tggtgaaatg    1020
ctggtaggag ggctcttcca ggatgtaatg cagaagctca tggcagagct attcacactt    1080
```

| | |
|---|---|
| cacatcagtg ctgtttcctc accacagagg ttcctgaggt cacagtgttt tccaagtctc | 1140 |
| ccgtgacact gggtcagccc aacatcctca tctgtcttgt ggacaacatc tttcctcctg | 1200 |
| tggtcaacat cacatggctg agcaatgggc actcagtcac agaaggtgtt tctgagacca | 1260 |
| gcttcctctc caagagtgat cattccttct tcaagatcag ttacctcacc ctcctcccctt | 1320 |
| ctgctgagga gagttatgac tgcaaggtgg agcactgggg actggacaag cctcttctga | 1380 |
| aacactgggg taaggatgag ttnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nntttctttc tttctttctt tctttctttc tttcttctt tctttcttc tttctttctt | 1560 |
| tctttctttc tttttgaaa gaataaagca acaaaagcaa agatttattg aaaatgaaag | 1620 |
| tacacttcac atggtgggag cgggcctgag catagggcct caagagccac ttcatgggtt | 1680 |
| tctaatgata gacttcactc tcctccctaa gctggggacc atgagtcttt gcagagccaa | 1740 |
| ccctccaccc catcccatcc cacacacatg cacatgagca cactctgctt tctgacctca | 1800 |
| acgacttcat atccacagag cctgagattc cagcccctat gtcagagctc acagagactg | 1860 |
| tggtctgcgc cctgggggttg tctgtgggcc tcgtgggcat tgtggtgggc actgtcttca | 1920 |
| tcatccgagg cctgcgttca gttggtgctt ccagacacca agggcccttg tgaatcccat | 1980 |
| cctggaatgg aagtaagat tgagatttgt tagagctgaa tccgcagtat gagaggaagg | 2040 |
| aaagtggagg aggctgtgga catgaatggt tgaaagttgt aggggaattg ggaagtggca | 2100 |
| tgatgatgac ataggagcgg cctaggaccc atccatctca tgtctgtcct gttgcaggtg | 2160 |
| catcgccatc tacaggagca gaagagtgga cttgctacat gacctagcat tattttctgg | 2220 |
| ccccatttat catatccctt ttctcctcca aatgtttctc ctctcacctc ttctgtggga | 2280 |
| cttaaattgc tatatctgct cagagctcac aaatgccttt gaattatttc cctgacttcc | 2340 |
| tgatttttt cttttctcaa gtgttaccta ctaagggatg cctggagtaa gccacccagc | 2400 |
| tacctaattc ctca | 2414 |

<210> SEQ ID NO 83
<211> LENGTH: 2414
<212> TYPE: DNA
<213> ORGANISM: Homo sapiens
<220> FEATURE:
<221> NAME/KEY: misc_feature
<222> LOCATION: (1403)..(1502)
<223> OTHER INFORMATION: n is a, c, g, or t

<400> SEQUENCE: 83

| | |
|---|---|
| ccagtcctga gaggaaagaa aatacaatca gtttgttatt aactgaggaa agaattaagt | 60 |
| gaaagatgaa tcttaggaag cagaaggaag taaacctaat ctctgactaa gaaagctaaa | 120 |
| taccataata actcattcat tccttctttt gtttaattac attatttaat cataagtccg | 180 |
| tgatgtgcca ggcactcagg aaatagtaaa aactggacat gtgatattct gcccttgtgt | 240 |
| agcgcacatt atagtgggaa agaaagcgca atttttaaccg gacaactacc aacaataaga | 300 |
| gcggaggaag caggggttgg aaatgtccac aggctgtgcc aaagatgaag cccgtaatat | 360 |
| ttgaaagtca gtttctttca tcattttgtg tattaaggtt cttcttccc ctgttctcca | 420 |
| ccttcctgct tgtcatcttc actcatcagc tgaccacgtc gcctcttatg gtgtaaactt | 480 |
| gtaccagtct tacggtccct ctggccagta cacccatgaa tttgatggag atgagcagtt | 540 |
| ctacgtggac ctggggagga aggagactgt ctggtgtttg cctgttctca gacaatttag | 600 |

```
atttgacccg caatttgcac tgacaaacat cgctgtccta aaacataact tgaacagtct      660
gattaaacgc tccaactcta ccgctgctac caatggtatg tgtcaacaat tctgcccctc      720
tttactgatt tatcccttca taccaagttt cattatttta tttccaagag gtccccagat      780
cttctcatgg caattgctga aattttatca tctcccatct ctaaaatcac atattcccat      840
gtaatacaag ggtctttcca ttatccattc attaaatcct tctcggagag gtctcatcaa      900
cctcctactt tattaaacat gcccacagag agaagggcac aggaataaag cggaggcaat      960
gtgtcgttgc tcccaagcag aaggtaaata agacctcttt gactatcagg tggtgaaatg     1020
ctggtaggag ggctcttcca ggatgtaatg cagaagctca tggcagagct attcacactt     1080
cacatcagtg ctgttttcct c accacagagg ttcctgaggt cacagtgttt tccaagtctc     1140
ccgtgacact gggtcagccc aacatcctca tctgtcttgt ggacaacatc tttcctcctg     1200
tggtcaacat cacatggctg agcaatgggc actcagtcac agaaggtgtt tctgagacca     1260
gcttcctctc caagagtgat cattccttct tcaagatcag ttacctcacc ctcctccctt     1320
ctgctgagga gagttatgac tgcaaggtgg agcactgggg actggacaag cctcttctga     1380
aacactgggg taaggatgag ttnnnnnnnn nnnnnnnnnn nnnnnnnnnn nnnnnnnnnn     1440
nnnnnnnnnn nnnnnnnnnn nnnnnnnnnn nnnnnnnnnn nnnnnnnnnn nnnnnnnnnn     1500
nntttctttc tttctttctt tcttctttc tttctttctt tctttcttc tttctttctt     1560
tctttctttc tttttgaaa gaataaagca acaaaagcaa agatttattg aaaatgaaag     1620
tacacttcac atggtgggag cgggcctgag cataggggct caagagccac ttcatgggtt     1680
tctaatgata gacttcactc tcctcccta a gctgggacc atgagtcttt gcagagccaa     1740
ccctccaccc catcccatcc cacacacatg cacatgagca cactctgctt tctgacctca     1800
acgacttcat atccacagag cctgagattc cagcccctat gtcagagctc acagagactg     1860
tggtctgcgc cctggggttg tctgtgggcc tcgtgggcat tgtggtgggc actgtcttca     1920
tcatccgagg cctgcgttca gttggtgctt ccagacacca agggcccttg tgaatcccat     1980
cctggaatgg aaggtaagat tgagatttgt tagagctgaa tccgcagtat gagaggaagg     2040
aaagtggagg aggctgtgga catgaatggt tgaaagttgt aggggaattg ggaagtggca     2100
tgatgatgac ataggagcgg cctaggaccc atccatctca tgtctgtcct gttgcaggtg     2160
catcgccatc tacaggagca gaagagtgga cttgctacat gacctagcat tattttctgg     2220
ccccatttat catatcccctt ttctcctcca aatgtttctc ctctcacctc ttctgtggga     2280
cttaaattgc tatatctgct cagagctcac aaatgccttt gaattatttc cctgacttcc     2340
tgattttttt cttttctcaa gtgttaccta ctaagggatg cctggagtaa gccacccagc     2400
tacctaattc ctca                                                       2414

<210> SEQ ID NO 84
<211> LENGTH: 5961
<212> TYPE: DNA
<213> ORGANISM: Homo sapiens

<400> SEQUENCE: 84 tccccccttaa tttgccctat tgaaagaatc ccaagtataa gaacaactgg tttttaatca       60
atattacaaa gatgtttact gttgaatcgc atttttcttt ggcttcttaa aatcccttag      120
gcattcaatc ttcagctctt ccataattga gaggaaattt tcacctcaaa tgttcatcca      180
gtgcaattga aagacgtcac agtgccaggc actggattca gaaccttcac aaaaaaaaaa      240
tctgcccaga gacagatgag gtccttcagc tccagtgctg attggttcct ttccaaggga      300
```

```
ccatccaatc ctaccacgca tggaaacatc cacagatttt tattctttct gccaggtaca    360
tcagatccat caggtccgag ctgtgttgac taccactttt cccttcgtct caattatgtc    420
ttggaaaaag gctttgcgga tccccggagg ccttcgggca gcaactgtga ccttgatgct    480
gtcgatgctg agcaccccag tggctgaggg cagagactct cccggtaagt gcagggcagc    540
tgctctccag agccgctact ctgggaacag gctctccttg ggctggggta cggggatggt    600
gatctccata atctcggaca caatctttta tcaacatttc ctctgttttg ggaaagagag    660
ctatgttgca tttccattta tcttttaatg atgaagtgag gacaatccaa tcccatccta    720
caggcttaag cctggaagag gaggagagag gagagaaaag aggagacaaa gtgttcattt    780
actaccagtg ataggacaaa gtgagcatgg ggttattttt gaagatatga atttctccaa    840
agacacagca ggatttgcca tttaggcgtg tcccaagact tgcctggact aaatattatg    900
atttcctgca ttgggaaatg caaggcagca atggtgtctg tagtctccgt atttggggaa    960
aagttgtctg tattcctgac ccagtggagc gtttgtggag gcaaaatctt ggtactgagg   1020
gaagctgact ggctgaccac agaaagagag ccttcaggtt tcactgatt atgggcaaat   1080 ggtgacctga gtgggattca gatacccgag ttgatgatgg actaaattta gtagaaagga   1140
ggatgtaaag aagggaaata acacatactg tgaaaccact catttcagac acagaacaat   1200
actttacata aattctctct cactccttct aacatcctgt gtgtagatat catgattttc   1260
ttttacacaa ttatacttgt gatatggata ttctgttaca taacctgccc gggctggtga   1320
ctgccacagt ttaatgggaa tctagtttat caaattcaaa agcttgtgct ctttcggtga   1380
ataaatgttt ctttctagga ctcagagatc taggactccc ttctttctaa cacagacgtg   1440
agtgaacctc acagggcact tgggagggta atccaggca tgggaaggaa ggtattttac    1500
ccagggacca agagaatagg cgtatcggaa gaggacaggt ttaattcctg gacctgtctc   1560
gtcattccct tgaactgtca ggtttatgtg gataacttta tctctgaggt acccaggagc   1620
tccatggaaa atgagatttc atgcgagaac gccctgatcc ctctaagtgc agaggtccat   1680
gtaaaatcag cccgactgcc tcttcacttg gttcacaggc cgagacaggg acagggcttt   1740
cctccctttc ctgcctgtag gaaggcggat tcccgaagac ccccgagagg gcgggcaggg   1800
ctgggcagag ccgccgggag gatcccaggt ctgcagcgcg aggcacgggc cggcgggaac   1860
ttgtggtcgc gcgggctgtt ccacagctcc gggccgggtc agggtggcgg ctgcgggggc   1920
ggacgggctg ggccgcactg actggccggt gattcctcgc agaggatttc gtgtaccagt   1980
ttaagggcat gtgctacttc accaacggga cagagcgcgt gcgtcttgtg agcagaagca   2040
tctataaccg agaagagatc gtgcgcttcg acagcgacgt gggggagttc cgggcggtga   2100
cgctgctggg gctgcctgcc gccgagtact ggaacagcca aaggacatc ctggagagga   2160 aacgggcggc ggtggacagg gtgtgcagac acaactacca gttggagctc cgcacgacct   2220
tgcagcggcg aggtgagcgg cgtcgcccct ctgcgaggcc cacccttggc cccaagtctc   2280
tgcgccagga ggggcgaagg gtcgtggcct ctggaacctg agcccgtttt gttccacccc   2340
agaggacagg aggcagcggc gagagtggtg ggggcaggtg catcggaggt gcggggacct   2400
agggcagagc aggggggacag gcagagttgg ccaggctgcc tagtgtcgcc ccagcctacc   2460
cgttcgtcgg ccttgtcctc tgctctgcat gttcttgcct cgtgccttat gcatttgcct   2520
ccttttgcct tacctttgct aagcagctct ctctgctcag aatgcccgcc ctcttcccct   2580
gcccgcccgc ccgcccccact agcactgccc cacccagcaa ggcccacgtg cacagctctt   2640
```

```
gcagcaggaa gcttcaggct tagcctggtg gagttagggc tgttccacaa ctgcgcgcag      2700
gacattcagc aattacagtt gtgaaataag atattttaac ttttggcttc aaatcattat      2760
tcatcgtaat tctgttttct taaatggctc tcattcatgg cagagatctt tgaggtgagg      2820
gtgttttaat cattgcatgc ctagtacctg acacattgac tggtatgtgg tgtgagctca      2880
atgatcttct gttaaattaa tgaataaatg tactcagctg cccatccact taggctcaag      2940
aaaaaaaaag aggtaaacag agccttaaaa atggacttta ttaattattt tctataattt      3000
tgcttaatgc tttaaagtaa actcttattg acttggatct taatagagtt tgtgaataca      3060
aaatctgagg aaaaagtttt ttgctaaaaa taaaaacaac gcttgaaaga tattgtaagg      3120
cagtttaaat ttcttttctt ttctttttttt ttttttttga gacggattct cactctgtcg      3180
cccaggccgg agtgcagtgg cgcgatctcg gctcactgca agctccgcct cccgggttca      3240
cgccattctc ctgcctcagc ctcctgagta ggtgggatta caggcgcgtg ccaccacgcc      3300
cggctaattt ttttgtattt ttagtagagg cggggtttca ccgtgttagc caggatggtc      3360
tggatctcct gacctcatga tccgcccgcc tcggcctccc aaagtgctgg gattacaggt      3420
gtgagccaca gtgcccggcc ggcacttttta atttcttaga aaagctgaac aaatggcaca      3480
atgcaaagag caaaagtttt ggaataaata gattgaagcc attaaattat tggataaaaa      3540
tagtttcggg ttgcttttgg cctaggttct cccctccccc catgactatc cacttcagga      3600
ataaacattc tgaaagtcaa ttttacccat ttagtgagca tttatttcta dacagttgcc      3660
ttatcaaata ccatctatgt tacgtcattt aatctcacag ttacttgtgc atcagagatt      3720
agcatcacca ctttatatat tggtacatga taaacacttt attggtcatg gatggggaga      3780
tggtcactgt aggctaatat tggtacatga taaacacttt aagtaatcag cccataattg      3840
ctcaccaaga ccttaagcct cccaaagtac acaacattct ttgtgttctt cactacacat      3900
ccatagagtc taagggacgt aaagcctcgt taaagccagt tttgaccaga agcagcaatg      3960
agtctattcc tgtgtgtttt ccatgttaat gggacaaaat gatactttca aggcattgaa      4020
aattcatgat taatcaatcc ctagtctgac cccagtgtta tctatgcagg tttgcaaaac      4080
ctttagttta cttaatactc ccttgccttc ttttgattca catcctaatg ccagcaaata      4140
cttatgtttt tgctatttca gttccatttc cataaaattt attttatcat cttttctcat      4200
aaatttatgc cctctatttt tactcccaat ctgtttaaga tgaacaaatc ttataaggcc      4260
acatagctga ctgttatttc tgttggactc caggaaggag aacctaaaga aaagttcaag      4320
tccaagcaga aaccgtgatt tcttccagat gatggctcat gagtgccatt taattggggt      4380
gccacctggt gacctcagca aatcccagct atatttatgt gttcacatta caggatcatt      4440
aacccagacc gaccactgca cagatctcag aatattttct atggagaaca tacataataa      4500
tgcctgattt cagaagaaga agtaattct caatagcaag gggatggagt agggtagaca      4560
gctgtaatta aactcacttg tgtgataaaa agaaattaag gaaaaaagaa atgagagaa      4620 catattacta aataaagaaa gcatacatta aatatttact atagtttcac actaagagaa      4680
taaaggaaat gcaataaagt ggcctgaaag gtaaaggatg agatgtgtaa aggggtgtag      4740 tattttttact atgagcagca atctgagaag ataaaggaat cgagttacgg gcaaacatga      4800
tgtttgatca gtgttatttg ttttcaaggc ctgcctaaat ttttttcaaa tattacaaac      4860
ttttgaaata acattctttt tgtttttttgc tgtctgttac taggttgcac atttttataaa      4920 ggcagggacc atggtatgtt gtttgtcttt ggattctcag tgattgttat atttatattt      4980
gttgaaggaa ccttaatcca agacttggac tccaagtatc tttccactct ggttccaagg      5040
```

```
agggaccttc ctcacagcag gcatgctgtg tggtctcaca tctcactcct atatctttcc      5100
ctgtctgtta ctgccctcag tggagcccac agtgaccatc tccccatcca ggacagaggc      5160
cctcaaccac cacaacctgc tggtctgctc ggtgacagat ttctatccag cccagatcaa      5220
agtccggtgg tttcggaatg accaggagga gacagctggc gttgtgtcca cccccttat       5280 taggaatggt gactggacct tccagatcct ggtgatgctg gaaatgactc cccagcgtgg      5340
agacgtctac acctgccacg tggagcaccc cagcctccag agcccatca ccgtggagtg       5400 gcgtaagggg atattgagtt tctgttactg tgggccccac aagacaaagg acagagctcc     5460
ttctgaccca tcccttccca tctcttatcc ctgatgtcac tgctgagctg ggaatcacag      5520
gagactagag cacctctagt tccatggcga gtgcatcaga agaatcctga tctcatcacc      5580
tttccagatg ctagggaaat tactctacat actgttgctc tggatcccag tcctgattgc      5640
tctgaggaac tgattattag ggctggtgac tgggatctta gggtctaagt ttatggatga      5700
gttcctgagg agtggagatc tgcttcccca ctctgtcacc tactcactgt atccaaggac      5760
ctattggctg gcctttccct cccttagggg tggtctgaat ggagaactag gttcctttga      5820
tgccttcacc tcctgcatct cagactggac ttcagctcct catcagggaa actatggggt      5880
atggggacaa acactgacac tcaggctctg cttctcaggg gctcaatctg aatctgccca      5940
gagcaagatg ctgagtggca t                                                 5961
```

<210> SEQ ID NO 85  
<211> LENGTH: 5938  
<212> TYPE: DNA  
<213> ORGANISM: Homo sapiens

<400> SEQUENCE: 85

```
ttgaaagaat cccaagtata agaacaactg gtttttaatc aatattacaa agatgtttac        60
tgttgaatcg cattttctct tggcttctta aaatcccctta ggcattcaat cttcagctct      120
tccataattg agaggaaatt ttcacctcaa atgttcatcc agtgcaattg aaagacgtca      180
cagtgccagg cactggattc agaaccttca cacaaaaaaa atctgcccag agacagatga      240
ggtccttcag ctccagtgct gattggttcc tttccaaggg accatccaat cctaccacgc      300
atggaaacat ccacagattt ttattctttc tgccaggtac atcagatcca tcaggtccga      360
gctgtgttga ctaccacttt tcccttcgtc tcaattatgt cttggaaaaa ggctttgcgg      420
atccccggag gccttcgggc agcaactgtg accttgatgc tgtcgatgct gagcacccca      480
gtggctgagg gcagagactc tcccggtaag tgcagggcag ctgctctcca gagccgctac      540
tctgggaaca ggctctcctt gggctggggt acggggatgg tgatctccat aatctcggac      600
acaatctttt atcaacattt cctctgtttt gggaaagaga gctatgttgc atttccattt      660 atctttaat gatgaagtga ggacaatcca atcccatcct acaggcttaa gcctggaaga      720
ggaggagaga ggagagaaaa gaggagacaa agtgttcatt tactaccagt gataggacaa      780
agtgagcatg gggttatttt tgaagatatg aatttctcca aagacacagc aggatttgcc      840
atttaggcgt gtcccaagac ttgcctggac taaatattat gatttcctgc attgggaaat      900
gcaaggcagc aatggtgtct gtagtctccg tatttgggga aaagttgtct gtattcctga      960
cccagtggag cgtttgtgga ggcaaaatct tggtactgag ggaagctgac tggctgacca     1020
cagaaagaga gccttcaggt ttcactgatt tatgggcaaa tggtgacctg agtgggattc     1080
agatacccga gttgatgatg gactaaattt agtgagaagg aggatgtaaa gaagggaaat     1140
```

```
aacacatact gtgaaaccac tcatttcaga cacagaacaa tactttacat aaattctctc    1200
tcactccttc taacatcctg tgtgtagata tcatgatttt cttttacaca attatacttg    1260
tgatatggat attctgttac ataacctgcc cgggctggtg actgccacag tttaatggga    1320
atctagttta tcaaattcaa aagcttgtgc tctttcggtg aataaatgtt tctttctagg    1380
actcagagat ctaggactcc cttctttcta acacagaagt gagtgaacct cacagggcac    1440
ttgggagggt aaatccaggc atgggaagga aggtatttta cccagggacc aagagaatag    1500
gcgtatcgga agaggacagg tttaattcct ggacctgtct cgtcattccc ttgaactgtc    1560
aggtttatgt ggataacttt atctctgagg tacccaggag ctccatggaa aatgagattt    1620
catgcgagaa cgccctgatc cctctaagtg cagaggtcca tgtaaaatca gcccgactgc    1680
ctcttcactt ggttcacagg ccgagacagg gacagggctt cctcccttt cctgccttta    1740 ggaaggcgga ttcccgaaga cccccgagag ggcgggcagg gctgggcaga gccgccggga    1800
ggatcccagg tctgcagcgc gaggcacggg ccggcgggaa cttgtggtcg cgcgggctgt    1860
tccacagctc cgggccgggt cagggtggcg gctgcggggg cggacgggct gggccgcact    1920
gactggccgg tgattcctcg cagaggattt cgtgtaccag tttaagggca tgtgctactt    1980
caccaacggg acagagcgcg tgcgtcttgt gagcagaagc atctataacc gagaagagat    2040
cgtgcgcttc gacagcgacg tgggggagtt ccggcggtg acgctgctgg gctgcctgc    2100 cgccgagtac tggaacagcc agaaggacat cctggagagaa aaacgggcgg cggtggacag    2160
ggtgtgcaga cacaactacc agttggagct ccgcacgacc ttgcagcggc gaggtgagcg    2220
gcgtcgcccc tctgcgaggc ccaccccttgg ccccaagtct ctgcgccagg aggggcgaag    2280
ggtcgttgcc tctggaacct gagccccgtt tgttccaccc cagaggacag gaggcagcgg    2340
cgagagtggt gggggcaggt gcatcggagg tgcggggacc tagggcagag caggggggaca    2400 ggcagagttg gccaggctgc ctagtgtcgc cccagcctac ccgttcgtcg gccttgtcct    2460
ctgctctgca tgttcttgcc tcgtgccttta tgcatttgcc tccttttgcc ttacctttgc    2520
taagcagctc tctctgctca gaatgcccgc cctcttcccc tgcccgcccg cccgccccgc    2580
tagcactgcc ccacccagca aggcccacgt gcacagctct tgcagcagga agcttcaggc    2640
ttagcctggt ggagttaggg ctgttccaca actgcgcgca ggacatccag caattacagt    2700
tgtgaaataa gatattttaa cttttggctt caaatcatta ttcatcgtaa ttctgttttc    2760
ttaaatggct ctcattcatg gcagagatct ttgaggtgag ggtgttttaa tcattgcatg    2820
cctagtacct gacacattga ctggtatgtg gtgtgagctc aatgatcttc tgttaaatta    2880
atgaataaat gtactcagct gcccatccac ttaggctcaa gaaaaaaaaa gaggtaaaca    2940
gagccttaaa aatggacttt attaattatt ttctataatt ttgcttaatg ctttaaagta    3000
aactcttatt gacttggatc ttaatagagt ttgtgaatac aaaatctgag gaaaaaagtt    3060
tttgctaaaa ataaaaacaa cgcttgaaag atattgtaat gcagtttaaa tttcttttct    3120
tttttttttt tttttttgaga cggattctca ctctgtcgcc caggccggag tgcagtggcg    3180
cgatctcggc tcactgcaag ctccgcctcc cgggttcacg ccattctcct gcctcagcct    3240
cctgagtagg tgggattaca ggcgcgtgcc accacgcccg gctaattttt ttgtattttt    3300
agtagaggcg gggtttcacc gtgttagcca ggatggtctg gatctcctga cctcatgatc    3360
cgcccgcctc ggcctcccaa agtgctggga ttacaggtgt gagccacagt gcccggccgg    3420
cacttttaat ttcttagaaa agctgaacaa atggcacaat gcaaagagca aaagttttgg    3480 aataaaataga ttgaagccat taaattattg gataaaaata gtttcgggtt gcttttggcc    3540
```

```
taggttctcc cctcccccca tgactatcca cttcaggaat aaacattctg aaagtcaatt    3600
ttacccattt agtgagcatt tatttctaga cagttgcctt atcaaatacc atctatgtta    3660
cgtcatttaa tctcacagtt acttgtgcat cagagattag catcaccact ttatatattg    3720
gtacatgata aacactttat tggtcatgga tggggagatg gtcactgtag gctaatattg    3780
gtacatgata aacactttaa gtaatcagcc cataattgct caccaagacc ttaagcctcc    3840
caaagtacac aacattcttt gtgttcttca ctacacatcc atagagtcta agggacgtaa    3900
agcctcgtta aagccagttt tgaccagaag cagcaatgag tctattcctg tgtgttttcc    3960
atgttaatgg gacaaaatga tactttcaag gcattgaaaa ttcatgatta atcaatcgct    4020
agtctgaccc cagtgttatc tatgcaggtt tgcaaaacct ttagtttact taatactccc    4080
ttgccttctt ttgattcaca tcctaatgcc agcaaatact tatgttttg ctatttcagt     4140 tccatttcca taaaatttat tttatcatct tttctcataa attatgccc tctatttta     4200 ctcccaatct gtttaagatg aacaaatctt ataaggccac atagctgact gttatttctg    4260
ttggactcca ggaaggagaa cctaaagaaa agttcaagtc caagcagaaa ccgtgatttc    4320
ttccagatga tggctcatga gtgccattta attggggtgc cacctggtga cctcagcaaa    4380
tcccagctat atttatgtgt tcacattaca ggatcattaa cccagaccga ccactgcaca    4440
gatctcagaa tattttctat ggagaacata cataataatg cctgatttca gaagaagaaa    4500
gtaattctca atagcaaggg gatggagtag ggtagacagc tgtaattaaa ctcacttgtg    4560
tgataaaaag aaattaagga aaaagaaaa tgagagaaca tattactaaa taagaaagc     4620 atacattaaa tatttactat agtttcacac taagagaata aaggaaatgc aataaagtgg    4680
cctgaaaggt aaaggatgag atgtgtaaag gggtgtagta tttttactat gagcagcaat    4740
ctgagaagat aaaggaatcg agttacgggc aaacatgatg tttgatcagt gttatttgtt    4800
ttcaaggcct gcctaaattt ttttcaaata ttacaaactt ttgaaataac attcttttg     4860 tttttttgctg tctgttacta ggttgcacat tttataaagg cagggaccat ggtatgttgt    4920
ttgtctttgg attctcagtg attgttatat ttatatttgt tgaaggaacc ttaatccaag    4980
acttggactc caagtatctt tccactctgg ttccaaggag ggaccttcct cacagcaggc    5040
atgctgtgtg gtctcacatc tcactcctat atctttccct gtctgttact gccctcagtg    5100
gagcccacag tgaccatctc cccatccagg acagaggccc tcaaccacca caacctgctg    5160
gtctgctcgg tgacagattt ctatccagcc cagatcaaag tccggtggtt tcggaatggc    5220
caggaggaga cagctggcgt tgtgtccacc ccccttatta ggaatggtga ctggaccttc    5280
cagatcctgg tgatgctgga aatgactccc cagcgtggag acgtctacac ctgccacgtg    5340
gagcacccca gcctccagag ccccatcacc gtggagtggc gtaagggat attgagtttc     5400 tgttactgtg ggccccacaa gacaaggac agagctcctt ctgacccatc ccttcccatc     5460
tcttatccct gatgtcactg ctgagctggg aatcacagga gactagagca cctctagttc    5520
catggcgagt gcatcagaag aatcctgatc tcatcacctt tccagatgct agggaaatta    5580
ctctacatac tgttgctctg gatcccagtc ctgattgctc tgaggaactg attattaggg    5640
ctggtgactg ggatcttagg gtctaagttt atggatgagt tcctgaggag tggagatctg    5700
cttccccact ctgtcaccta ctcactgtat ccaagtacct attggctggc ctttccctcc    5760
cttaggggtg gtctgaatgg agaactaggt tcctttgatg ccttcacctc ctgcatctca    5820
```

```
gactggactt cagctcctca tcagggaaac tatggggtat ggggacaaac actgacactc    5880
aggctctgct tctcaggggc tcaatctgaa tctgcccaga gcaagatgct gagtggca     5938
```

USE OF HLA GENETIC STATUS TO ASSESS OR SELECT TREATMENT OF CELIAC DISEASE

RELATED APPLICATIONS

This application is a 35 U.S.C. § 371 National Phase Application of International Application No. PCT/US2015/052939, filed Sep. 29, 2015, and entitled "USE OF HLA GENETIC STATUS TO ASSESS OR SELECT TREATMENT OF CELIAC DISEASE," which claims the benefit under 35 U.S.C. § 119(e) of U.S. provisional application No. 62/057,167, filed Sep. 29, 2014, the entire contents of each of which are incorporated by reference herein.

BACKGROUND OF THE INVENTION

Celiac disease, also known as coeliac disease or Celiac sprue (Coeliac sprue), affects approximately 1% of people in Europe and North America. In many of those affected, Celiac disease is unrecognised, but this clinical oversight is now being rectified with greater clinical awareness. A gluten free diet is the only currently approved treatment for Celiac disease, and because regular ingestion of as little as 50 mg of gluten (equivalent to $1/100^{th}$ of a standard slice of bread) can damage the small intestine; chronic inflammation of the small bowel is commonplace in subjects on a gluten free diet. Persistent inflammation of the small intestine has been shown to increase the risk of cancer, osteoporosis and death. As gluten is so widely used, for example, in commercial soups, sauces, ice-creams, etc., maintaining a gluten-free diet is difficult.

Celiac disease occurs in genetically susceptible individuals who possess either HLA-DQ2.5 (encoded by the genes HLA-DQA1*05 and HLA-DQB1*02) accounting for about 90% of individuals, HLA-DQ2.2 (encoded by the genes HLA-DQA1*02 and HLA-DQB1*02), or HLA-DQ8 (encoded by the genes HLA-DQA1*03 and HLA-DQB1*0302). Without wishing to be bound by theory, it is believed that such individuals mount an inappropriate HLA-DQ2- and/or DQ8-restricted $CD4^+$ T cell-mediated immune response to peptides derived from the aqueous-insoluble proteins of wheat flour, gluten, and related proteins in rye and barley.

SUMMARY OF THE INVENTION

As described herein, it has been found that subjects having Celiac disease that are homozygous for HLA-DQ2.5 have higher levels of circulating cytokines and/or adverse symptoms after administration of a gluten peptide composition. Accordingly, aspects of the disclosure relate to methods of selecting or adjusting a gluten peptide treatment based on the human leukocyte antigen (HLA) genotype of a subject being treated, such as a subject having or suspected of having Celiac disease.

Accordingly, aspects of the disclosure relate to a method of selecting or adjusting a gluten peptide treatment for a subject that has or is suspected of having Celiac disease based on a human leukocyte antigen (HLA) genotype of the subject.

In some embodiments of any one of the methods provided, the method further comprises assessing the HLA genotype of the subject.

In some embodiments of any one of the methods provided, assessing comprises determining the sequence of each copy of an HLA-DQA gene and each copy of an HLA-DQB gene in the subject. In some embodiments of any one of the methods provided, determining comprises performing a nucleic-acid based assay on each copy of the HLA-DQA gene, or a portion thereof, and each copy of the HLA-DQB gene, or a portion thereof. In some embodiments of any one of the methods provided, the nucleic-acid based assay is a probe-based assay or a sequencing assay.

In some embodiments of any one of the methods provided, assessing further comprises identifying the subject as having a homozygous HLA-DQ2.5 genotype or a non-homozygous HLA-DQ2.5 genotype. In some embodiments of any one of the methods provided, the non-homozygous HLA-DQ2.5 genotype is a heterozygous HLA-DQ2.5 genotype. In some embodiments of any one of the methods provided, the heterozygous HLA-DQ2.5 genotype is HLA-$DQ^{2.5/2.2}$, HLA-$DQ^{2.5/7}$, or HLA-$DQ^{2.5/8}$.

In some embodiments of any one of the methods provided, the method further comprises decreasing a dose of the gluten peptide treatment if the subject has a homozygous HLA-DQ2.5 genotype; or maintaining or increasing the dose of the gluten peptide treatment if the subject has a non-homozygous HLA-DQ2.5 genotype.

In some embodiments of any one of the methods provided, any one of the gluten peptide compositions may comprise at least one peptide comprising at least one amino acid sequence selected from PFPQPELPY (SEQ ID NO:1), PQPELPYPQ (SEQ ID NO:2), PFPQPEQPF (SEQ ID NO:3), PQPEQPFPW (SEQ ID NO:4), PIPEQPQPY (SEQ ID NO:5) and EQPIPEQPQ (SEQ ID NO:6).

In some embodiments of any one of the methods provided, any one of the gluten peptide compositions may comprise:

a) a first peptide comprising the amino acid sequence PFPQPELPY (SEQ ID NO:1) and the amino acid sequence PQPELPYPQ (SEQ ID NO:2);

b) a second peptide comprising the amino acid sequence PFPQPEQPF (SEQ ID NO:3) and the amino acid sequence PQPEQPFPW (SEQ ID NO:4); and c) a third peptide comprising the amino acid sequence EQPIPEQPQ (SEQ ID NO:6) and the amino acid sequence PIPEQPQPY (SEQ ID NO:5).

In some embodiments of any one of the methods provided, any one of the gluten peptide compositions may comprise a first peptide that comprises the amino acid sequence LQPFPQPELPYPQPQ; a second peptide that comprises the amino acid sequence QPFPQPEQPFPWQP (SEQ ID NO: 7); and a third peptide that comprises the amino acid sequence PEQPIPEQPQPYPQQ (SEQ ID NO: 8). In some embodiments of any one of the methods provided, any one of the gluten peptide compositions may comprise a first peptide that comprises the amino acid sequence ELQPFPQPELPYPQPQ (SEQ ID NO: 9), wherein the N-terminal glutamate is a pyroglutamate and the C-terminal glutamine is amidated; a second peptide that comprises the amino acid sequence EQPFPQPEQPFPWQP (SEQ ID NO: 10), wherein the N-terminal glutamate is a pyroglutamate and the C-terminal proline is amidated; and a third peptide that comprises the amino acid sequence EPEQPIPEQPQPYPQQ (SEQ ID NO: 11), wherein the N-terminal glutamate is a pyroglutamate and the C-terminal glutamine is amidated.

In some embodiments of any one of the methods provided, the dose is or is decreased to less than 300 micrograms if the subject has a homozygous HLA-DQ2.5 genotype. In some embodiments of any one of the methods provided, the dose is or is decreased to less than 150 micrograms if the subject has a homozygous HLA-DQ2.5 genotype. In some embodiments of any one of the methods provided, the dose is selected to be up to 300 micrograms if the subject has a heterozygous HLA-DQ2.5 genotype. In some embodiments of any one of the methods provided herein, the amount selected based on HLA-DQ2.5 genotype is any one of the foregoing.

Other aspects of the disclosure relate to a method of measuring a level of at least one circulating cytokine or chemokine in a subject that has or is suspected of having Celiac disease, wherein the subject has been administered a first composition comprising at least one gluten peptide in an amount selected based on a human leukocyte antigen (HLA) genotype of the subject, and assessing the likelihood the subject has Celiac disease.

In some embodiments of any one of the methods provided, the method further includes comprises assessing the HLA genotype of the subject.

In some embodiments of any one of the methods provided assessing comprises determining the sequence of each copy of an HLA-DQA gene and each copy of an HLA-DQB gene in the subject. In some embodiments of any one of the methods provided, determining comprises performing a nucleic-acid based assay on each copy of the HLA-DQA gene, or a portion thereof, and each copy of the HLA-DQB gene, or a portion thereof. In some embodiments of any one of the methods provided, the nucleic-acid based assay is a probe-based assay or a sequencing assay.

In some embodiments of any one of the methods provided, assessing further comprises identifying the subject as having a homozygous HLA-DQ2.5 genotype or a non-homozygous HLA-DQ2.5 genotype. In some embodiments of any one of the methods provided, the non-homozygous HLA-DQ2.5 genotype is a heterozygous HLA-DQ2.5 genotype. In some embodiments of any one of the methods provided, the heterozygous HLA-DQ2.5 genotype is HLA-$DQ^{2.5/2.2}$, HLA-$DQ^{2.5/7}$, or HLA-$DQ^{2.5/8}$.

In some embodiments of any one of the methods provided, the method further comprises decreasing the amount of a composition, e.g., a first composition, a second composition, or both, comprising at least one gluten peptide administered to the subject if the subject has a homozygous HLA-DQ2.5 genotype; or maintaining or increasing the amount of a composition, e.g., a first composition, a second composition, or both, comprising at least one gluten peptide administered to the subject if the subject has a non-homozygous HLA-DQ2.5 genotype. In some embodiments of any one of the methods provided, the methods further comprises selecting any one of the amounts or doses as described herein.

In some embodiments of any one of the methods provided, a composition, e.g., a first composition and/or a second composition, comprising at least one gluten peptide comprises:

a first peptide comprising the amino acid sequence PFPQPELPY (SEQ ID NO:1) and the amino acid sequence PQPELPYPQ (SEQ ID NO:2);

a second peptide comprising the amino acid sequence PFPQPEQPF (SEQ ID NO:3) and the amino acid sequence PQPEQPFPW (SEQ ID NO:4); and a third peptide comprising the amino acid sequence EQPIPEQPQ (SEQ ID NO:6) and the amino acid sequence PIPEQPQPY (SEQ ID NO:5).

In some embodiments of any one of the methods provided, the first peptide comprises the amino acid sequence LQPFPQPELPYPQPQ (SEQ ID NO: 62); the second peptide comprises the amino acid sequence QPFPQPEQPF-WQP (SEQ ID NO: 7); and the third peptide comprises the amino acid sequence PEQPIPEQPQPYPQQ (SEQ ID NO: 8).

In some embodiments of any one of the methods provided, the first peptide comprises the amino acid sequence ELQPFPQPELPYPQPQ (SEQ ID NO: 9), wherein the N-terminal glutamate is a pyroglutamate and the C-terminal glutamine is amidated; the second peptide comprises the amino acid sequence EQPFPQPEQPFPWQP (SEQ ID NO: 10), wherein the N-terminal glutamate is a pyroglutamate and the C-terminal proline is amidated; and the third peptide comprises the amino acid sequence EPEQPIPEQPQPYPQQ (SEQ ID NO: 11), wherein the N-terminal glutamate is a pyroglutamate and the C-terminal glutamine is amidated.

In some embodiments of any one of the methods provided, the amount of the composition comprising at least one gluten peptide is or is decreased to less than 300 micrograms if the subject has a homozygous HLA-DQ2.5 genotype. In some embodiments of any one of the methods provided the amount of the composition comprising at least one gluten peptide is or is decreased to less than 150 micrograms if the subject has a homozygous HLA-DQ2.5 genotype.

In some embodiments of any one of the methods provided, the method further comprises obtaining a sample from the subject and the measuring is performed on the sample.

In some embodiments of any one of the methods provided, the sample from the subject is obtained 1 hour to 6 hours after the subject has been administered the first composition. In some embodiments of any one of the methods provided, the sample from the subject is obtained 4 hours to 6 hours after the subject has been administered the first composition. In some embodiments of any one of the methods provided, the sample from the subject is a plasma or serum sample.

In some embodiments of any one of the methods provided, the subject has been administered the first composition by injection. In some embodiments of any one of the methods provided, the subject has been administered the first composition by oral administration.

In some embodiments of any one of the methods provided, the method further comprises administering the first composition to the subject prior to measuring the level of the at least one circulating cytokine or chemokine. In some embodiments of any one of the methods provided, the at least one circulating cytokine or chemokine is MCP-1, IP-10, IL-6, IL-8, G-CSF, IL-2, IL-1RA, GRO, EOTAXIN, GM-CSF, IL-10, TNFa, IFNa2, MIP-1b, IL-12P70, IL-1a, IL-17A, EGF, MIP-1a, FRACTALKINE, IFNg, VEGF, IL-9, FGF-2, IL-1b, Flt-3L, I-15, TNFb, IL-12(P40), MCP-3, IL-4, MDC, IL-13, TGF-a, IL-3, IL-5, IL-7 or sCD40L.

In some embodiments of any one of the methods provided, an elevated level of the at least one circulating cytokine or chemokine compared to a control level of the at least one circulating cytokine or chemokine indicates that the subject has Celiac disease, and the step of assessing comprises comparing the level of the at least one circulating cytokine or chemokine to a control level of the at least one circulating cytokine or chemokine. In some embodiments of any one of the methods provided, the control level is a baseline level. In some embodiments of any one of the methods provided, the baseline level is a level of the at least one circulating cytokine or chemokine prior to administration of the first composition.

In some embodiments of any one of the methods provided, the method further comprises recording whether or not the subject has celiac disease based on the assessing.

In some embodiments of any one of the methods provided, the method further comprises treating, suggesting a treatment, or giving information in regard to a treatment to the subject.

In some embodiments of any one of the methods provided, the method further comprises:

decreasing a dose of the gluten peptide treatment if the subject has a homozygous HLA-DQ2.5 genotype; or maintaining or increasing the dose of the gluten peptide treatment if the subject has a non-homozygous HLA-DQ2.5 genotype.

In some embodiments of any one of the methods provided, measuring the level of the at least one circulating cytokine or chemokine comprises an immuno-based assay. In some embodiments of any one of the methods provided, the immuno-based assay comprises an ELISA or a multiplex bead-based assay.

In some embodiments of any one of the methods provided, the method further comprises measuring a T cell response to the first composition comprising the at least one gluten peptide.

Other aspects of the disclosure relate to a method for assessing tolerance to a gluten peptide in a subject having Celiac disease, the method comprising: measuring a level of at least one circulating cytokine or chemokine in a subject having Celiac disease, wherein the subject has been administered a first composition comprising at least one gluten peptide in an amount selected based on a human leukocyte antigen (HLA) genotype of the subject, and assessing the tolerance of the subject to the at least one gluten peptide based on the measuring.

In some embodiments of any one of the methods provided, the method further comprises assessing the HLA genotype of the subject. In some embodiments of any one of the methods provided, assessing comprises determining the sequence of each copy of an HLA-DQA gene and each copy of an HLA-DQB gene in the subject. In some embodiments of any one of the methods provided, determining comprises performing a nucleic-acid based assay on each copy of the HLA-DQA gene, or a portion thereof, and each copy of the HLA-DQB gene, or a portion thereof. In some embodiments of any one of the methods provided the nucleic-acid based assay is a probe-based assay or a sequencing assay.

In some embodiments of any one of the methods provided, assessing further comprises identifying the subject as having a homozygous HLA-DQ2.5 genotype or a non-homozygous HLA-DQ2.5 genotype. In some embodiments of any one of the methods provided, the non-homozygous HLA-DQ2.5 genotype is a heterozygous HLA-DQ2.5 genotype. In some embodiments of any one of the methods provided, the heterozygous HLA-DQ2.5 genotype is HLA-DQ$^{2.5/2.2}$, HLA-DQ$^{2.5/7}$, or HLA-DQ$^{2.5/8}$.

In some embodiments of any one of the methods provided, the method further comprises: decreasing the amount of the first composition comprising at least one gluten peptide administered to the subject if the subject has a homozygous HLA-DQ2.5 genotype; or maintaining or increasing the amount of the first composition comprising at least one gluten peptide administered to the subject if the subject has a non-homozygous HLA-DQ2.5 genotype.

In some embodiments of any one of the methods provided, a composition, e.g., a first composition and/or a second composition, comprising at least one gluten peptide comprises:

a first peptide comprising the amino acid sequence PFPQPELPY (SEQ ID NO:1) and the amino acid sequence PQPELPYPQ (SEQ ID NO:2);

a second peptide comprising the amino acid sequence PFPQPEQPF (SEQ ID NO:3) and the amino acid sequence PQPEQPFPW (SEQ ID NO:4); and a third peptide comprising the amino acid sequence EQPIPEQPQ (SEQ ID NO:6) and the amino acid sequence PIPEQPQPY (SEQ ID NO:5).

In some embodiments of any one of the methods provided, the first peptide comprises the amino acid sequence LQPFPQPELPYPQPQ (SEQ ID NO: 62); the second peptide comprises the amino acid sequence QPFPQPEQPFPWQP (SEQ ID NO: 7); and the third peptide comprises the amino acid sequence PEQPIPEQPQPYPQQ (SEQ ID NO: 8).

In some embodiments of any one of the methods provided, the first peptide comprises the amino acid sequence ELQPFPQPELPYPQPQ (SEQ ID NO: 9), wherein the N-terminal glutamate is a pyroglutamate and the C-terminal glutamine is amidated; the second peptide comprises the amino acid sequence EQPFPQPEQPFPWQP (SEQ ID NO: 10), wherein the N-terminal glutamate is a pyroglutamate and the C-terminal proline is amidated; and the third peptide comprises the amino acid sequence EPEQPIPEQPQPYPQQ (SEQ ID NO: 11), wherein the N-terminal glutamate is a pyroglutamate and the C-terminal glutamine is amidated.

In some embodiments of any one of the methods provided, the amount of the composition comprising at least one gluten peptide is or is decreased to less than 300 micrograms if the subject has a homozygous HLA-DQ2.5 genotype. In some embodiments of any one of the methods provided, the amount of the composition comprising at least one gluten peptide is or is decreased to less than 150 micrograms if the subject has a homozygous HLA-DQ2.5 genotype.

In some embodiments of any one of the methods provided, the method further comprises obtaining a sample from the subject and the measuring is performed on the sample. In some embodiments of any one of the methods provided, the sample from the subject is obtained 1 hour to 6 hours after the subject has been administered the first composition. In some embodiments of any one of the methods provided, the sample from the subject is obtained 4 hours to 6 hours after the subject has been administered the first composition. In some embodiments of any one of the methods provided, the sample from the subject is a plasma or serum sample.

In some embodiments of any one of the methods provided, the subject has been administered the first composition by injection. In some embodiments of any one of the methods provided, the subject has been administered the first composition by oral administration.

In some embodiments of any one of the methods provided, the method further comprises administering the first composition to the subject prior to measuring the level of the at least one circulating cytokine or chemokine. In some embodiments of any one of the methods provided, the at least one circulating cytokine or chemokine is MCP-1, IP-10, IL-6, IL-8, G-CSF, IL-2, IL-1RA, GRO, EOTAXIN, GM-CSF, IL-10, TNFa, IFNa2, MIP-1b, IL-12P70, IL-1a, IL-17A, EGF, MIP-1a, FRACTALKINE, IFNg, VEGF, IL-9, FGF-2, IL-1b, Flt-3L, I-15, TNFb, IL-12(P40), MCP-3, IL-4, MDC, IL-13, TGF-a, IL-3, IL-5, IL-7 or sCD40L.

In some embodiments of any one of the methods provided, an elevated level of the at least one circulating cytokine or chemokine compared to a control level of the at least one circulating cytokine or chemokine indicates that the subject has Celiac disease, and the step of assessing comprises comparing the level of the at least one circulating cytokine or chemokine to a control level of the at least one circulating cytokine or chemokine. In some embodiments of any one of the methods provided, the control level is a baseline level. In some embodiments of any one of the methods provided, the baseline level is a level of the at least one circulating cytokine or chemokine prior to administration of the first composition.

In some embodiments of any one of the methods provided, the method further comprises recording whether or not the subject has celiac disease based on the assessing. In some embodiments of any one of the methods provided, the method further comprises treating, suggesting a treatment, or giving information in regard to a treatment to the subject.

In some embodiments of any one of the methods provided, the method further comprises: decreasing a dose of the gluten peptide treatment if the subject has a homozygous HLA-DQ2.5 genotype; or maintaining or increasing the dose of the gluten peptide treatment if the subject has a non-homozygous HLA-DQ2.5 genotype.

In some embodiments of any one of the methods provided, measuring the level of the at least one circulating cytokine or chemokine comprises an immuno-based assay. In some embodiments of any one of the methods provided, the immuno-based assay comprises an ELISA or a multiplex bead-based assay.

In some embodiments of any one of the methods provided, the method further comprises measuring a T cell response to the first composition comprising the at least one gluten peptide.

Other aspects of the disclosure relate to a kit comprising i) the first composition as defined by any one of the methods provided, and ii) a binding partner for the at least one cytokine or chemokine as defined by any one of the methods provided. In some embodiments of any one of the methods provided, the kit further comprises iii) a means for injecting the first composition.

Other aspects of the disclosure relate to a method comprising: administering to a subject that has or is suspected of having Celiac disease a first composition comprising at least one gluten peptide in an amount selected based on an HLA genotype of the subject, measuring a T cell response to a second composition comprising at least one gluten peptide in a sample from the subject, and assessing the likelihood that the subject has Celiac disease.

In some embodiments of any one of the methods provided, the first composition and the second composition comprise the same gluten peptide or peptides. In some embodiments of any of the methods provided, the sample is contacted with the second composition.

In some embodiments of any one of the methods provided, the method further comprises obtaining the sample from the subject.

In some embodiments of any one of the methods provided, the subject is orally administered or directed to consume gluten for at least three days.

In some embodiments of any one of the methods provided, the measuring step is performed six days after the last of the gluten is orally administered or consumed.

In some embodiments of any one of the methods provided, IFN-gamma is measured. In some embodiments of any one of the methods provided, IP-10 is measured.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1 is a table showing the number of subjects in each of Cohorts 1, 2, and 7 that were homozygous for HLA-DQ2.5, heterozygous HLA-DQ2.5/2.2 or 2.5/7, heterozygous HLA-DQ2.5 or HLA-DQ2.5/unknown.

FIG. 2 is a table showing the median peak fold change in circulating cytokines from pre-dose after $1^{st}$ dose of the gluten peptide composition. Other means non-HLA-DQ2.5 homozygous subjects. Sx=symptoms.

DETAILED DESCRIPTION OF THE INVENTION

Figure 3:
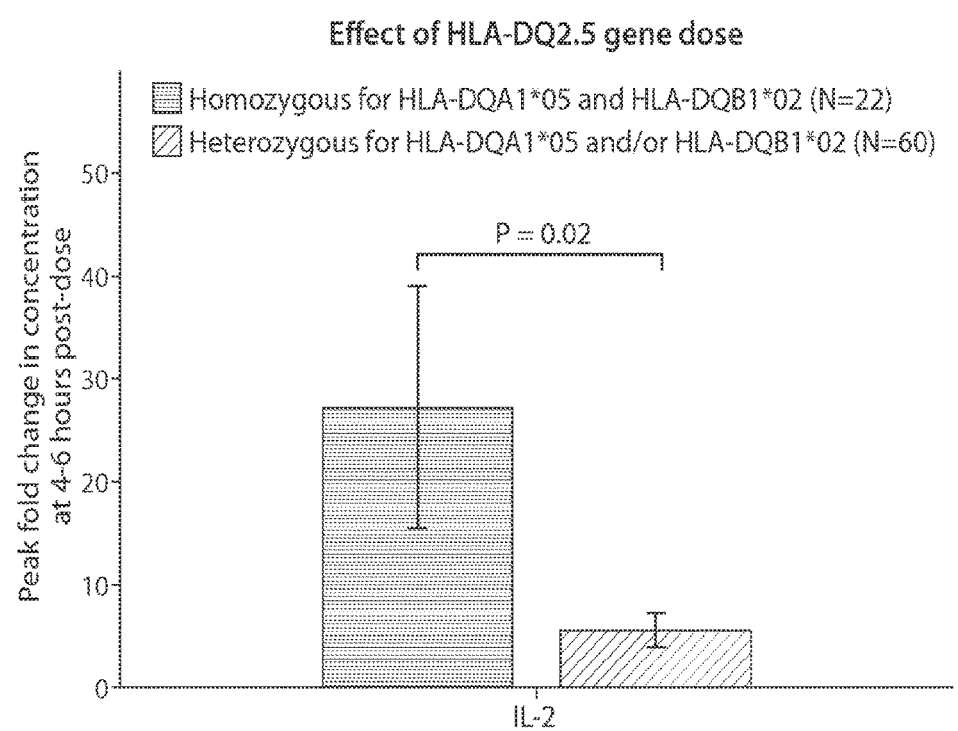
FIG. 3 is a graph showing the peak fold change in concentration of IL-2 at 4-6 hours after dose of the gluten peptide composition in subjects that were homozygous for HLA-DQ2.5 (n=22) or heterozygous HLA-DQ2.5/2.2 or 2.5/7, heterozygous HLA-DQ2.5 or HLA-DQ2.5/unknown (n=60).

As described herein, it has been found that subjects who are homozygous for the HLA-DQ2.5 genotype have higher levels of circulating cytokines and/or adverse events in response to administration of a gluten peptide treatment. Accordingly, aspects of the disclosure relate to selecting or adjusting a gluten peptide treatment for a subject (e.g., a subject having or suspected of having Celiac disease) based on the human leukocyte antigen (HLA) genotype of the subject.

Methods

Aspects of the disclosure relate to a method, comprising selecting or adjusting a gluten peptide treatment for a subject that has or is suspected of having Celiac disease based on a human leukocyte antigen (HLA) genotype of the subject. Gluten peptide treatments are further described herein.

Another aspect of the disclosure relates to a method of identifying (e.g., diagnosing) a subject, such as a subject having or suspected of having Celiac disease based on the HLA-DQ2.5 genotype.

Yet another aspect of the disclosure relates to a method of assessing the efficacy of treatment of Celiac disease (e.g., responsiveness to a therapeutic gluten peptide composition) based on the HLA-DQ2.5 genotype.

In some embodiments, the method further comprises assessing the HLA genotype of the subject. In some embodiments of any one of the methods described herein, the assessing comprises determining the sequence of each copy of an HLA-DQA gene and each copy of an HLA-DQB gene (including determining the sequence of a portion thereof) in the subject. HLA genes and genotypes are further described herein.

In some embodiments of any one of the methods described herein, determining the sequence comprises reading sequence information, e.g., on a chart, on a print-out, or on a computer such as in a database of sequence information. In some embodiments, the sequence information may be conveyed as a symbol or other words, numbers or letters that indicate the sequence (e.g., DQA1*05 or DQB1*02).

In some embodiments, assessing the genotype includes being given or being told the genotype information for the subject. In some embodiments, assessing the genotype of subject includes obtaining genotype information for the subject from an individual, e.g., a patient provider or laboratory personnel, a tangible medium, e.g., on a chart or print out, or an intangible medium, e.g., a database.

In some embodiments, assessing the genotype includes performing an assay on a patient or patient sample.

In some embodiments of any one of the methods described herein, determining comprises performing a nucleic-acid based assay on one or both copies of the HLA-DQA gene, or a portion thereof, and on one or both copies of the HLA-DQB gene, or a portion thereof. In some embodiments, the nucleic-acid based assay is a probe-based assay or a sequencing assay. Nucleic-acid based assays are further described herein.

In some embodiments of any one of the methods described herein, assessing further comprises identifying the subject as having a homozygous HLA-DQ2.5 genotype or a non-homozygous HLA-DQ2.5 genotype. In some embodiments, the non-homozygous HLA-DQ2.5 genotype is a heterozygous HLA-DQ2.5 genotype. HLA-DQ2.5 genotypes are further described herein.

In some embodiments of any one of the methods described herein, the method further comprises decreasing a dose of the gluten peptide treatment if the subject has a homozygous HLA-DQ2.5 genotype; or maintaining or increasing the dose of the gluten peptide treatment if the subject has a non-homozygous HLA-DQ2.5 genotype.

In some embodiments of any one of the methods described herein, the method further comprises measuring a level of at least one circulating cytokine or chemokine in a subject that has or is suspected of having celiac disease, wherein the subject has been administered a composition comprising a decreased dose of at least one gluten peptide as described herein based on the HLA-DQ2.5 genotype.

In some embodiments of any one of the methods provided, the dose is or is decreased to less than 300 micrograms of the gluten peptides if the subject has a homozygous HLA-DQ2.5 genotype. In some embodiments of any one of the methods provided, the dose is or is decreased to less than 150 micrograms if the subject has a homozygous HLA-DQ2.5 genotype. In some embodiments of any one of the methods provided, the dose is or is increased to up to 300 micrograms if the subject has a heterozygous HLA-DQ2.5 genotype.

In some embodiments of any one of the methods provided, the dose of the gluten peptides is selected to be up to 300 micrograms if the subject has a heterozygous HLA-DQ2.5 genotype.

In some embodiments, the selected dose for a subject having a homozygous DQ2.5 genotype is less than the dose that would be selected for a subject having a heterozygous DQ2.5 genotype. In some embodiments, the selected dose for a subject having a heterozygous DQ2.5 genotype is more than the dose that would be selected for a subject having a homozygous DQ2.5 genotype.

HLA Genotypes

Aspects of the disclosure relate to the assessment and/or assaying of an HLA genotype in a subject. In some embodiments, the assessing comprises determining the presence or absence of one or more HLA-DQA alleles and one or more HLA-DQB alleles. In some embodiments, the assessing comprises determining the sequence of one or more copies of an HLA-DQA gene and/or one or more copies of an HLA-DQB gene (including determining the sequence of a portion of each gene or determining the identity of a SNP associated with a particular allele) in a subject. In some embodiments, the HLA genotype is a homozygous HLA-DQ2.5 genotype or a non-homozygous HLA-DQ2.5 genotype. The non-homozygous HLA-DQ2.5 genotype may be, e.g., a heterozygous HLA-DQ2.5 genotype. Exemplary heterozygous HLA-DQ2.5 genotypes include, but are not limited to, HLA-DQ2.5/2.2, HLA-DQ2.5/7, or HLA-DQ2.5/8.

Exemplary HLA-DQA and HLA-DQB alleles for the HLA-DQA and HLA-DQB genes are: HLA-DQ2.5 (DQA1*05 and DQB1*02), DQ2.2 (DQA1*02 and DQB1*02), DQ7 (DQA1*05 and DQB1*0301) and DQ8 (DQA1*03 and DQB1*0302). Exemplary sequences for DQA and DQB alleles are shown below.

```
HLA-DQA1*0501 (Genbank accession number: AF515813.1)
DQA1*0501 allele, 3' UTR and partial cds
                                                        (SEQ ID NO: 82)
GGCCTGCGTTCAGTTGGTGCTTCCAGACACCAAGGGCCCTTGTGAATCCCATCCTGGAATGGAAGGTAAG

ATTGAGATTTGTTAGAGCTGAATCCGCAGTATGAGAGGAAGGAAAGTGGAGGAGGCTGTGGACATGAATG

GTTGAAAGTTGTAGGGGAATTGGGAAGTGGCATGATGATGACATAGGAGCGGCCTAGGACCCATCCATCT

CATGTCTGTCCTGTTGCAGGTGCATCGCCATCTACAGGAGCAGAAGAGTGGACTTGCTACATGACCTAGC

ATTATTTTCTGGCCCCATTTATCATATCCCTTTTCTCCTCCAAATGTTTCTCCTCTCACCTCTTCTGTGG

GACTTAAATTGCTATATCTGCTCAGAGCTCACAAATGCCTTTGAATTATTTCCCTGACTTCCTGATTTTT

TTCTTCTTAAGTGTTACCTACTAAGAGTTGCCTGGAGTAAGCCACCCAGCTACCTAATTCCTCAGTAACC

TCCATCTATAATCTCCATGGAAGCAACAAATTCCCTTTATGAGATATATGTCAAATTTTTCCATCTTTCA

TCCAGGGCTGACTGAAACCGTGGCTAAGAATTGGGAGACTCTCTTGTTTCAAGCCAATTTAACATCATTT

ACCAGATCATTTGTCATGTCCAGTAACACAGAAGCAACCAACTACAGTATAGCCTGATAACATGTTGATT

TCTTAGCTGACATTAATATTTCTTTCTTCCTTGTGTTCCCACCCTTGGCATTGCCACCCACCCCTCAATT

AAGGCAACAATGAAGTTAATGGATACCCTCTGCCTTTGGCTCAGAAATGTTATAGCAAAAATTTTAAAAT

AAAAAGTAAGTCTGTACTAATTTCAATATGACTTTTAAAAGTATGACAGAGAAATGGGTTGGGATAAAG
```

```
GAAATTTGAATCTCAAAAATATCAATAGTGAAAAGTTATTCTCAAAACTTTAAATTTGTGAAGAATGATG

ACAGTAGAAGCCTTCCTCTCCCCTCCTCACCCTGAAGGAATAAAATTTCCTTAGGCAGGAAAAGAAATGG

AAGTCAGAAAAACATTAGAATAAGACAATAATGTGGGTATCTGAAAAGGAACAAATACTCATTCCTCACA

TAGGGTTAGTGACAATGG
```

HLA-DQA1*0505 (Genbank accession number: AH013295.2)
HLA-DQA1*0505 allele, partial cds (SEQ ID NO: 83)

```
CCAGTCCTGAGAGGAAAGAAAATACAATCAGTTTGTTATTAACTGAGGAAAGAATTAAGTGAAAGATGAA

TCTTAGGAAGCAGAAGGAAGTAAACCTAATCTCTGACTAAGAAAGCTAAATACCATAATAACTCATTCAT

TCCTTCTTTTGTTTAATTACATTATTTAATCATAAGTCCGTGATGTGCCAGGCACTCAGGAAATAGTAAA

AACTGGACATGTGATATTCTGCCCTTGTGTAGCGCACATTATAGTGGGAAAGAAAGCGCAATTTTAACCG

GACAACTACCAACAATAAGAGCGGAGGAAGCAGGGGTTGGAAATGTCCACAGGCTGTGCCAAAGATGAAG

CCCGTAATATTTGAAAGTCAGTTTCTTTCATCATTTTGTGTATTAAGGTTCTTTCTTCCCCTGTTCTCCA

CCTTCCTGCTTGTCATCTTCACTCATCAGCTGACCACGTCGCCTCTTATGGTGTAAACTTGTACCAGTCT

TACGGTCCCTCTGGCCAGTACACCCATGAATTTGATGGAGATGAGCAGTTCTACGTGGACCTGGGGAGGA

AGGAGACTGTCTGGTGTTTGCCTGTTCTCAGACAATTTAGATTTGACCCGCAATTTGCACTGACAAACAT

CGCTGTCCTAAAACATAACTTGAACAGTCTGATTAAACGCTCCAACTCTACCGCTGCTACCAATGGTATG

TGTCAACAATTCTGCCCCTCTTTACTGATTTATCCCTTCATACCAAGTTTCATTATTTTATTTCCAAGAG

GTCCCCAGATCTTCTCATGGCAATTGCTGAAATTTTATCATCTCCCATCTCTAAAATCACATATTCCCAT

GTAATACAAGGGTCTTTCCATTATCCATTCATTAAATCCTTCTCGGAGAGGTCTCATCAACCTCCTACTT

TATTAAACATGCCCACAGAGAGAAGGGCACAGGAATAAAGCGGAGGCAATGTGTCGTTGCTCCCAAGCAG

AAGGTAAATAAGACCTCTTTGACTATCAGGTGGTGAAATGCTGGTAGGAGGGCTCTTCCAGGATGTAATG

CAGAAGCTCATGGCAGAGCTATTCACACTTCACATCAGTGCTGTTTCCTCACCACAGAGGTTCCTGAGGT

CACAGTGTTTTCCAAGTCTCCCGTGACACTGGGTCAGCCCAACATCCTCATCTGTCTTGTGGACAACATC

TTTCCTCCTGTGGTCAACATCACATGGCTGAGCAATGGGCACTCAGTCACAGAAGGTGTTTCTGAGACCA

GCTTCCTCTCCAAGAGTGATCATTCCTTCTTCAAGATCAGTTACCTCACCCTCCTCCCTTCTGCTGAGGA

GAGTTATGACTGCAAGGTGGAGCACTGGGGACTGGACAAGCCTCTTCTGAAACACTGGGGTAAGGATGAG

TTNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNTTTCTTTCTTTCTTTCTTTCTTTCTTTCTTTCTTTCTT

TCTTTCTTTCTTTCTTTCTTTCTTTCTTTTTTGAAAGAATAAAGCAACAAAAGCAAAGATTTATTG

AAAATGAAAGTACACTTCACATGGTGGGAGCGGGCCTGAGCATAGGGGCTCAAGAGCCACTTCATGGGTT

TCTAATGATAGACTTCACTCTCCTCCCTAAGCTGGGGACCATGAGTCTTTGCAGAGCCAACCCTCCACCC

CATCCCATCCCACACACATGCACATGAGCACACTCTGCTTTCTGACCTCAACGACTTCATATCCACAGAG

CCTGAGATTCCAGCCCCTATGTCAGAGCTCACAGAGACTGTGGTCTGCGCCCTGGGGTTGTCTGTGGGCC

TCGTGGGCATTGTGGTGGGCACTGTCTTCATCATCCGAGGCCTGCGTTCAGTTGGTGCTTCCAGACACCA

AGGGCCCTTGTGAATCCCATCCTGGAATGGAAGGTAAGATTGAGATTTGTTAGAGCTGAATCCGCAGTAT

GAGAGGAAGGAAAGTGGAGGAGGCTGTGGACATGAATGGTTGAAAGTTGTAGGGGAATTGGGAAGTGGCA

TGATGATGACATAGGAGCGGCCTAGGACCCATCCATCTCATGTCTGTCCTGTTGCAGGTGCATCGCCATC

TACAGGAGCAGAAGAGTGGACTTGCTACATGACCTAGCATTATTTTCTGGCCCCATTTATCATATCCCTT

TTCTCCTCCAAATGTTTCTCCTCTCACCTCTTCTGTGGGACTTAAATTGCTATATCTGCTCAGAGCTCAC

AAATGCCTTTGAATTATTTCCCTGACTTCCTGATTTTTTTCTTTTCTCAAGTGTTACCTACTAAGGGATG

CCTGGAGTAAGCCACCCAGCTACCTAATTCCTCA
```

-continued

HLA-DQB1*0201 (Genbank accession number: AY375842.1)
HLA-DQB1*0201 allele, exons 1 through 4, and partial cds (SEQ ID NO: 84)
TCCCCCTTAATTTGCCCTATTGAAAGAATCCCAAGTATAAGAACAACTGGTTTTTAATCAATATTACAAA

GATGTTTACTGTTGAATCGCATTTTTCTTTGGCTTCTTAAAATCCCTTAGGCATTCAATCTTCAGCTCTT

CCATAATTGAGAGGAAATTTTCACCTCAAATGTTCATCCAGTGCAATGAAAGACGTCACAGTGCCAGGC

ACTGGATTCAGAACCTTCACAAAAAAAAAATCTGCCCAGAGACAGATGAGGTCCTTCAGCTCCAGTGCTG

ATTGGTTCCTTTCCAAGGGACCATCCAATCCTACCACGCATGGAAACATCCACAGATTTTTATTCTTTCT

GCCAGGTACATCAGATCCATCAGGTCCGAGCTGTGTTGACTACCACTTTTCCCTTCGTCTCAATTATGTC

TTGGAAAAAGGCTTTGCGGATCCCCGGAGGCCTTCGGGCAGCAACTGTGACCTTGATGCTGTCGATGCTG

AGCACCCCAGTGGCTGAGGGCAGAGACTCTCCCGGTAAGTGCAGGGCAGCTGCTCTCCAGAGCCGCTACT

CTGGGAACAGGCTCTCCTTGGGCTGGGGTACGGGGATGGTGATCTCCATAATCTCGGACACAATCTTTTA

TCAACATTTCCTCTGTTTTGGGAAAGAGAGCTATGTTGCATTTCCATTTATCTTTTAATGATGAAGTGAG

GACAATCCAATCCCATCCTACAGGCTTAAGCCTGGAAGAGGAGGAGAGAGGAGAGAAAAGAGGAGACAAA

GTGTTCATTTACTACCAGTGATAGGACAAAGTGAGCATGGGGTTATTTTTGAAGATATGAATTTCTCCAA

AGACACAGCAGGATTTGCCATTTAGGCGTGTCCCAAGACTTGCCTGGACTAAATATTATGATTTCCTGCA

TTGGGAAATGCAAGGCAGCAATGGTGTCTGTAGTCTCCGTATTTGGGGAAAAGTTGTCTGTATTCCTGAC

CCAGTGGAGCGTTTGTGGAGGCAAAATCTTGGTACTGAGGGAAGCTGACTGGCTGACCACAGAAAGAGAG

CCTTCAGGTTTCACTGATTTATGGGCAAATGGTGACCTGAGTGGGATTCAGATACCCGAGTTGATGATGG

ACTAAATTTAGTAGAAAGGAGGATGTAAAGAAGGGAAATAACACATACTGTGAAACCACTCATTTCAGAC

ACAGAACAATACTTTACATAAATTCTCTCTCACTCCTTCTAACATCCTGTGTGTAGATATCATGATTTTC

TTTTACACAATTATACTTGTGATATGGATATTCTGTTACATAACCTGCCCGGGCTGGTGACTGCCACAGT

TTAATGGGAATCTAGTTTATCAAATTCAAAAGCTTGTGCTCTTTCGGTGAATAAATGTTTCTTTCTAGGA

CTCAGAGATCTAGGACTCCCTTCTTTCTAACACAGACGTGAGTGAACCTCACAGGGCACTTGGGAGGGTA

AATCCAGGCATGGGAAGGAAGGTATTTTACCCAGGGACCAAGAGAATAGGCGTATCGGAAGAGGACAGGT

TTAATTCCTGGACCTGTCTCGTCATTCCCTTGAACTGTCAGGTTTATGTGGATAACTTTATCTCTGAGGT

ACCCAGGAGCTCCATGGAAAATGAGATTTCATGCGAGAACGCCCTGATCCCTCTAAGTGCAGAGGTCCAT

GTAAAATCAGCCCGACTGCCTCTTCACTTGGTTCACAGGCCGAGACAGGGACAGGGCTTTCCTCCCTTTC

CTGCCTGTAGGAAGGCGGATTCCCGAAGACCCCCGAGAGGGCGGGCAGGGCTGGGCAGAGCCGCCGGGAG

GATCCCAGGTCTGCAGCGCGAGGCACGGGCCGGCGGGAACTTGTGGTCGCGCGGGCTGTTCCACAGCTCC

GGGCCGGGTCAGGGTGGCGGCTGCGGGGGCGGACGGGCTGGGCCGCACTGACTGGCCGGTGATTCCTCGC

AGAGGATTTCGTGTACCAGTTTAAGGGCATGTGCTACTTCACCAACGGGACAGAGCGCGTGCGTCTTGTG

AGCAGAAGCATCTATAACCGAGAAGAGATCGTGCGCTTCGACAGCGACGTGGGGGAGTTCCGGGCGGTGA

CGCTGCTGGGCTGCCTGCCGCCGAGTACTGGAACAGCCAGAAGGACATCCTGGAGAGGAAACGGGCGGC

GGTGGACAGGGTGTGCAGACACAACTACCAGTTGGAGCTCCGCACGACCTTGCAGCGGCGAGGTGAGCGG

CGTCGCCCCTCTGCGAGGCCCACCCTTGGCCCCAAGTCTCTGCGCCAGGAGGGGCGAAGGGTCGTGGCCT

CTGGAACCTGAGCCCCGTTTGTTCCACCCCAGAGGACAGGAGGCAGCGGCGAGAGTGGTGGGGGCAGGTG

CATCGGAGGTGCGGGGACCTAGGGCAGAGCAGGGGGACAGGCAGAGTTGGCCAGGCTGCCTAGTGTCGCC

CCAGCCTACCCGTTCGTCGGCCTTGTCCTCTGCTCTGCATGTTCTTGCCTCGTGCCTTATGCATTTGCCT

CCTTTTGCCTTACCTTTGCTAAGCAGCTCTCTCTGCTCAGAATGCCCGCCCTCTTCCCCTGCCCGCCCGC

CCGCCCCACTAGCACTGCCCCACCCAGCAAGGCCCACGTGCACAGCTCTTGCAGCAGGAAGCTTCAGGCT

TAGCCTGGTGGAGTTAGGGCTGTTCCACAACTGCGCGCAGGACATTCAGCAATTACAGTTGTGAAATAAG

-continued

```
ATATTTTAACTTTTGGCTTCAAATCATTATTCATCGTAATTCTGTTTTCTTAAATGGCTCTCATTCATGG

CAGAGATCTTTGAGGTGAGGGTGTTTTAATCATTGCATGCCTAGTACCTGACACATTGACTGGTATGTGG

TGTGAGCTCAATGATCTTCTGTTAAATTAATGAATAAATGTACTCAGCTGCCCATCCACTTAGGCTCAAG

AAAAAAAAGAGGTAAACAGAGCCTTAAAAATGGACTTTATTAATTATTTTCTATAATTTTGCTTAATGC

TTTAAAGTAAACTCTTATTGACTTGGATCTTAATAGAGTTTGTGAATACAAAATCTGAGGAAAAAGTTT

TTGCTAAAAATAAAAACAACGCTTGAAAGATATTGTAAGGCAGTTTAAATTTCTTTTCTTTTCTTTTTTT

TTTTTTTGAGACGGATTCTCACTCTGTCGCCCAGGCCGGAGTGCAGTGGCGCGATCTCGGCTCACTGCA

AGCTCCGCCTCCCGGGTTCACGCCATTCTCCTGCCTCAGCCTCCTGAGTAGGTGGGATTACAGGCGCGTG

CCACCACGCCCGGCTAATTTTTTGTATTTTTAGTAGAGGCGGGGTTTCACCGTGTTAGCCAGGATGGTC

TGGATCTCCTGACCTCATGATCCGCCCGCCTCGGCCTCCCAAAGTGCTGGGATTACAGGTGTGAGCCACA

GTGCCCGGCCGGCACTTTTAATTTCTTAGAAAAGCTGAACAAATGGCACAATGCAAAGAGCAAAAGTTTT

GGAATAAATAGATTGAAGCCATTAAATTATTGGATAAAAATAGTTTCGGGTTGCTTTTGGCCTAGGTTCT

CCCCTCCCCCCATGACTATCCACTTCAGGAATAAACATTCTGAAAGTCAATTTTACCCATTTAGTGAGCA

TTTATTTCTAGACAGTTGCCTTATCAAATACCATCTATGTTACGTCATTTAATCTCACAGTTACTTGTGC

ATCAGAGATTAGCATCACCACTTTATATATTGGTACATGATAAACACTTTATTGGTCATGGATGGGAGA

TGGTCACTGTAGGCTAATATTGGTACATGATAAACACTTTAAGTAATCAGCCCATAATTGCTCACCAAGA

CCTTAAGCCTCCCAAAGTACACAACATTCTTTGTGTTCTTCACTACACATCCATAGAGTCTAAGGGACGT

AAAGCCTCGTTAAAGCCAGTTTTGACCAGAAGCAGCAATGAGTCTATTCCTGTGTGTTTTCCATGTTAAT

GGGACAAAATGATACTTTCAAGGCATTGAAAATTCATGATTAATCAATCCCTAGTCTGACCCCAGTGTTA

TCTATGCAGGTTTGCAAAACCTTTAGTTTACTTAATACTCCCTTGCCTTCTTTTGATTCACATCCTAATG

CCAGCAAATACTTATGTTTTGCTATTTCAGTTCCATTTCCATAAAATTTATTTTATCATCTTTTCTCAT

AAATTTATGCCCTCTATTTTTACTCCCAATCTGTTTAAGATGAACAAATCTTATAAGGCCACATAGCTGA

CTGTTATTTCTGTTGGACTCCAGGAAGGAGAACCTAAAGAAAAGTTCAAGTCCAAGCAGAAACCGTGATT

TCTTCCAGATGATGGCTCATGAGTGCCATTTAATTGGGGTGCCACCTGGTGACCTCAGCAAATCCCAGCT

ATATTTATGTGTTCACATTACAGGATCATTAACCCAGACCGACCACTGCACAGATCTCAGAATATTTTCT

ATGGAGAACATACATAATAATGCCTGATTTCAGAAGAAGAAAGTAATTCTCAATAGCAAGGGGATGGAGT

AGGGTAGACAGCTGTAATTAAACTCACTTGTGTGATAAAAAGAAATTAAGGAAAAAAGAAAATGAGAGAA

CATATTACTAAATAAAGAAAGCATACATTAAATATTTACTATAGTTTCACACTAAGAGAATAAAGGAAAT

GCAATAAAGTGGCCTGAAAGGTAAAGGATGAGATGTGTAAAGGGGTGTAGTATTTTTACTATGAGCAGCA

ATCTGAGAAGATAAAGGAATCGAGTTACGGGCAAACATGATGTTTGATCAGTGTTATTTGTTTTCAAGGC

CTGCCTAAATTTTTTTCAAATATTACAAACTTTTGAAATAACATTCTTTTTGTTTTTTGCTGTCTGTTAC

TAGGTTGCACATTTTATAAAGGCAGGGACCATGGTATGTTGTTTGTCTTTGGATTCTCAGTGATTGTTAT

ATTTATATTTGTTGAAGGAACCTTAATCCAAGACTTGGACTCCAAGTATCTTTCCACTCTGGTTCCAAGG

AGGGACCTTCCTCACAGCAGGCATGCTGTGTGGTCTCACATCTCACTCCTATATCTTTCCCTGTCTGTTA

CTGCCCTCAGTGGAGCCCACAGTGACCATCTCCCCATCCAGGACAGAGGCCCTCAACCACCACAACCTGC

TGGTCTGCTCGGTGACAGATTTCTATCCAGCCCAGATCAAAGTCCGGTGGTTTCGGAATGACCAGGAGGA

GACAGCTGGCGTTGTGTCCACCCCCCTTATTAGGAATGGTGACTGGACCTTCCAGATCCTGGTGATGCTG

GAAATGACTCCCCAGCGTGGAGACGTCTACACCTGCCACGTGGAGCACCCCAGCCTCCAGAGCCCCATCA

CCGTGGAGTGGCGTAAGGGGATATTGAGTTTCTGTTACTGTGGGCCCCACAAGACAAAGGACAGAGCTCC

TTCTGACCCATCCCTTCCCATCTCTTATCCCTGATGTCACTGCTGAGCTGGGAATCACAGGAGACTAGAG

CACCTCTAGTTCCATGGCGAGTGCATCAGAAGAATCCTGATCTCATCACCTTTCCAGATGCTAGGGAAAT
```

-continued

```
TACTCTACATACTGTTGCTCTGGATCCCAGTCCTGATTGCTCTGAGGAACTGATTATTAGGGCTGGTGAC

TGGGATCTTAGGGTCTAAGTTTATGGATGAGTTCCTGAGGAGTGGAGATCTGCTTCCCCACTCTGTCACC

TACTCACTGTATCCAAGGACCTATTGGCTGGCCTTTCCTCCCTTAGGGGTGGTCTGAATGGAGAACTAG

GTTCCTTTGATGCCTTCACCTCCTGCATCTCAGACTGGACTTCAGCTCCTCATCAGGGAAACTATGGGGT

ATGGGGACAAACACTGACACTCAGGCTCTGCTTCTCAGGGGCTCAATCTGAATCTGCCCAGAGCAAGATG

CTGAGTGGCAT
```

HLA-DQB1*0202 (Genbank accession number: AY375844.1)
HLA-DQB1*0202 allele, exons 1 through 4, and partial cds (SEQ ID NO: 85)

```
TTGAAAGAATCCCAAGTATAAGAACAACTGGTTTTTAATCAATATTACAAAGATGTTTACTGTTGAATCG

CATTTTTCTTTGGCTTCTTAAAATCCCTTAGGCATTCAATCTTCAGCTCTTCCATAATTGAGAGGAAATT

TTCACCTCAAATGTTCATCCAGTGCAATTGAAAGACGTCACAGTGCCAGGCACTGGATTCAGAACCTTCA

CACAAAAAAAATCTGCCCAGAGACAGATGAGGTCCTTCAGCTCCAGTGCTGATTGGTTCCTTTCCAAGGG

ACCATCCAATCCTACCACGCATGGAAACATCCACAGATTTTTATTCTTTCTGCCAGGTACATCAGATCCA

TCAGGTCCGAGCTGTGTTGACTACCACTTTTCCCTTCGTCTCAATTATGTCTTGGAAAAAGGCTTTGCGG

ATCCCCGGAGGCCTTCGGGCAGCAACTGTGACCTTGATGCTGTCGATGCTGAGCACCCCAGTGGCTGAGG

GCAGAGACTCTCCCGGTAAGTGCAGGGCAGCTGCTCTCCAGAGCCGCTACTCTGGGAACAGGCTCTCCTT

GGGCTGGGGTACGGGGATGGTGATCTCCATAATCTCGGACACAATCTTTTATCAACATTTCCTCTGTTTT

GGGAAAGAGAGCTATGTTGCATTTCCATTTATCTTTTAATGATGAAGTGAGGACAATCCAATCCCATCCT

ACAGGCTTAAGCCTGGAAGAGGAGGAGAGAGGAGAGAAAAGAGGAGACAAAGTGTTCATTTACTACCAGT

GATAGGACAAAGTGAGCATGGGGTTATTTTTGAAGATATGAATTTCTCCAAAGACACAGCAGGATTTGCC

ATTTAGGCGTGTCCCAAGACTTGCCTGGACTAAATATTATGATTTCCTGCATTGGGAAATGCAAGGCAGC

AATGGTGTCTGTAGTCTCCGTATTTGGGGAAAAGTTGTCTGTATTCCTGACCCAGTGGAGCGTTTGTGGA

GGCAAAATCTTGGTACTGAGGGAAGCTGACTGGCTGACCACAGAAAGAGAGCCTTCAGGTTTCACTGATT

TATGGGCAAATGGTGACCTGAGTGGGATTCAGATACCCGAGTTGATGATGGACTAAATTTAGTAGAAAGG

AGGATGTAAAGAAGGGAAATAACACATACTGTGAAACCACTCATTTCAGACACAGAACAATACTTTACAT

AAATTCTCTCTCACTCCTTCTAACATCCTGTGTGTAGATATCATGATTTTCTTTTACACAATTATACTTG

TGATATGGATATTCTGTTACATAACCTGCCCGGGCTGGTGACTGCCACAGTTTAATGGGAATCTAGTTTA

TCAAATTCAAAAGCTTGTGCTCTTTCGGTGAATAAATGTTTCTTTCTAGGACTCAGAGATCTAGGACTCC

CTTCTTTCTAACACAGAAGTGAGTGAACCTCACAGGGCACTTGGGAGGGTAAATCCAGGCATGGGAAGGA

AGGTATTTTACCCAGGGACCAAGAGAATAGGCGTATCGGAAGAGGACAGGTTTAATTCCTGGACCTGTCT

CGTCATTCCCTTGAACTGTCAGGTTTATGTGGATAACTTTATCTCTGAGGTACCCAGGAGCTCCATGGAA

AATGAGATTTCATGCGAGAACGCCCTGATCCCTCTAAGTGCAGAGGTCCATGTAAAATCAGCCCGACTGC

CTCTTCACTTGGTTCACAGGCCGAGACAGGGACAGGGCTTTCCTCCCTTTCCTGCCTTTAGGAAGGCGGA

TTCCCGAAGACCCCCGAGAGGGCGGGCAGGGCTGGGCAGAGCCGCCGGGAGGATCCCAGGTCTGCAGCGC

GAGGCACGGGCCGGCGGGAACTTGTGGTCGCGCGGGCTGTTCCACAGCTCCGGGCCGGGTCAGGGTGGCG

GCTGCGGGGCGGACGGGCTGGGCCGCACTGACTGGCCGGTGATTCCTCGCAGAGGATTTCGTGTACCAG

TTTAAGGGCATGTGCTACTTCACCAACGGGACAGAGCGCGTGCGTCTTGTGAGCAGAAGCATCTATAACC

GAGAAGAGATCGTGCGCTTCGACAGCGACGTGGGGGAGTTCCGGGCGGTGACGCTGCTGGGGCTGCCTGC

CGCCGAGTACTGGAACAGCCAGAAGGACATCCTGGAGAGGAAACGGGCGGCGGTGGACAGGGTGTGCAGA

CACAACTACCAGTTGGAGCTCCGCACGACCTTGCAGCGGCGAGGTGAGCGGCGTCGCCCCTCTGCGAGGC

CCACCCTTGGCCCCAAGTCTCTGCGCCAGGAGGGGCGAAGGGTCGTTGCCTCTGGAACCTGAGCCCCGTT
```

-continued

```
TGTTCCACCCCAGAGGACAGGAGGCAGCGGCGAGAGTGGTGGGGGCAGGTGCATCGGAGGTGCGGGGACC

TAGGGCAGAGCAGGGGGACAGGCAGAGTTGGCCAGGCTGCCTAGTGTCGCCCCAGCCTACCCGTTCGTCG

GCCTTGTCCTCTGCTCTGCATGTTCTTGCCTCGTGCCTTATGCATTTGCCTCCTTTTGCCTTACCTTTGC

TAAGCAGCTCTCTCTGCTCAGAATGCCCGCCCTCTTCCCCTGCCCGCCCGCCCGCCCCGCTAGCACTGCC

CCACCCAGCAAGGCCCACGTGCACAGCTCTTGCAGCAGGAAGCTTCAGGCTTAGCCTGGTGGAGTTAGGG

CTGTTCCACAACTGCGCGCAGGACATCCAGCAATTACAGTTGTGAAATAAGATATTTTAACTTTTGGCTT

CAAATCATTATTCATCGTAATTCTGTTTTCTTAAATGGCTCTCATTCATGGCAGAGATCTTTGAGGTGAG

GGTGTTTTAATCATTGCATGCCTAGTACCTGACACATTGACTGGTATGTGGTGTGAGCTCAATGATCTTC

TGTTAAATTAATGAATAAATGTACTCAGCTGCCCATCCACTTAGGCTCAAGAAAAAAAAGAGGTAAACA

GAGCCTTAAAAATGGACTTTATTAATTATTTTCTATAATTTTGCTTAATGCTTTAAAGTAAACTCTTATT

GACTTGGATCTTAATAGAGTTTGTGAATACAAAATCTGAGGAAAAAAGTTTTTGCTAAAAATAAAAACAA

CGCTTGAAAGATATTGTAATGCAGTTTAAATTTCTTTTCTTTTTTTTTTTTTTTTGAGACGGATTCTCA

CTCTGTCGCCCAGGCCGGAGTGCAGTGGCGCGATCTCGGCTCACTGCAAGCTCCGCCTCCCGGGTTCACG

CCATTCTCCTGCCTCAGCCTCCTGAGTAGGTGGGATTACAGGCGCGTGCCACCACGCCCGGCTAATTTTT

TTGTATTTTTAGTAGAGGCGGGGTTTCACCGTGTTAGCCAGGATGGTCTGGATCTCCTGACCTCATGATC

CGCCCGCCTCGGCCTCCCAAAGTGCTGGGATTACAGGTGTGAGCCACAGTGCCCGGCCGGCACTTTTAAT

TTCTTAGAAAAGCTGAACAAATGGCACAATGCAAAGAGCAAAAGTTTTGGAATAAATAGATTGAAGCCAT

TAAATTATTGGATAAAAATAGTTTCGGGTTGCTTTTGGCCTAGGTTCTCCCCTCCCCCCATGACTATCCA

CTTCAGGAATAAACATTCTGAAAGTCAATTTTACCCATTTAGTGAGCATTTATTTCTAGACAGTTGCCTT

ATCAAATACCATCTATGTTACGTCATTTAATCTCACAGTTACTTGTGCATCAGAGATTAGCATCACCACT

TTATATATTGGTACATGATAAACACTTTATTGGTCATGGATGGGAGATGGTCACTGTAGGCTAATATTG

GTACATGATAAACACTTTAAGTAATCAGCCCATAATTGCTCACCAAGACCTTAAGCCTCCCAAAGTACAC

AACATTCTTTGTGTTCTTCACTACACATCCATAGAGTCTAAGGGACGTAAAGCCTCGTTAAAGCCAGTTT

TGACCAGAAGCAGCAATGAGTCTATTCCTGTGTGTTTTCCATGTTAATGGGACAAAATGATACTTTCAAG

GCATTGAAAATTCATGATTAATCAATCGCTAGTCTGACCCCAGTGTTATCTATGCAGGTTTGCAAAACCT

TTAGTTTACTTAATACTCCCTTGCCTTCTTTTGATTCACATCCTAATGCCAGCAAATACTTATGTTTTTG

CTATTTCAGTTCCATTTCCATAAAATTTATTTTATCATCTTTTCTCATAAATTTATGCCCTCTATTTTTA

CTCCCAATCTGTTTAAGATGAACAAATCTTATAAGGCCACATAGCTGACTGTTATTTCTGTTGGACTCCA

GGAAGGAGAACCTAAAGAAAAGTTCAAGTCCAAGCAGAAACCGTGATTTCTTCCAGATGATGGCTCATGA

GTGCCATTTAATTGGGGTGCCACCTGGTGACCTCAGCAAATCCCAGCTATATTTATGTGTTCACATTACA

GGATCATTAACCCAGACCGACCACTGCACAGATCTCAGAATATTTTCTATGGAGAACATACATAATAATG

CCTGATTTCAGAAGAAGAAAGTAATTCTCAATAGCAAGGGGATGGAGTAGGGTAGACAGCTGTAATTAAA

CTCACTTGTGTGATAAAAAGAAATTAAGGAAAAAAGAAATGAGAGAACATATTACTAAATAAAGAAAGC

ATACATTAAATATTTACTATAGTTTCACACTAAGAGAATAAAGGAAATGCAATAAAGTGGCCTGAAAGGT

AAAGGATGAGATGTGTAAAGGGGTGTAGTATTTTACTATGAGCAGCAATCTGAGAAGATAAAGGAATCG

AGTTACGGGCAAACATGATGTTTGATCAGTGTTATTTGTTTTCAAGGCCTGCCTAAATTTTTTCAAATA

TTACAAACTTTTGAAATAACATTCTTTTTGTTTTTTGCTGTCTGTTACTAGGTTGCACATTTTATAAAGG

CAGGGACCATGGTATGTTGTTTGTCTTTGGATTCTCAGTGATTGTTATATTTATATTTGTTGAAGGAACC

TTAATCCAAGACTTGGACTCCAAGTATCTTTCCACTCTGGTTCCAAGGAGGGACCTTCCTCACAGCAGGC

ATGCTGTGTGGTCTCACATCTCACTCCTATATCTTTCCCTGTCTGTTACTGCCCTCAGTGGAGCCCACAG
```

```
TGACCATCTCCCCATCCAGGACAGAGGCCCTCAACCACCACAACCTGCTGGTCTGCTCGGTGACAGATTT

CTATCCAGCCCAGATCAAAGTCCGGTGGTTTCGGAATGGCCAGGAGGAGACAGCTGGCGTTGTGTCCACC

CCCCTTATTAGGAATGGTGACTGGACCTTCCAGATCCTGGTGATGCTGGAAATGACTCCCCAGCGTGGAG

ACGTCTACACCTGCCACGTGGAGCACCCCAGCCTCCAGAGCCCCATCACCGTGGAGTGGCGTAAGGGGAT

ATTGAGTTTCTGTTACTGTGGGCCCCACAAGACAAAGGACAGAGCTCCTTCTGACCCATCCCTTCCCATC

TCTTATCCCTGATGTCACTGCTGAGCTGGGAATCACAGGAGACTAGAGCACCTCTAGTTCCATGGCGAGT

GCATCAGAAGAATCCTGATCTCATCACCTTTCCAGATGCTAGGGAAATTACTCTACATACTGTTGCTCTG

GATCCCAGTCCTGATTGCTCTGAGGAACTGATTATTAGGGCTGGTGACTGGGATCTTAGGGTCTAAGTTT

ATGGATGAGTTCCTGAGGAGTGGAGATCTGCTTCCCCACTCTGTCACCTACTCACTGTATCCAAGTACCT

ATTGGCTGGCCTTTCCCTCCCTTAGGGGTGGTCTGAATGGAGAACTAGGTTCCTTTGATGCCTTCACCTC

CTGCATCTCAGACTGGACTTCAGCTCCTCATCAGGGAAACTATGGGGTATGGGGACAAACACTGACACTC

AGGCTCTGCTTCTCAGGGGCTCAATCTGAATCTGCCCAGAGCAAGATGCTGAGTGGCA
```

HLA Genotype Assays

Other aspects of the disclosure relate to assays for detecting the HLA genotype of a subject, e.g., a nucleic-acid based assay. The HLA genotype may be detected, e.g., using one or more single nucleotide polymorphisms associated with an HLA genotype or by sequencing all or part of an HLA-DQA and/or HLA-DQB gene. Exemplary SNPs for use in HLA genotyping include, but are not limited to: rs2187668, rs2395182, rs4713586, rs7775228, rs4639334, and rs7454108. Any one or more of such exemplary SNPs may be used for HLA genotyping.

Detection of a nucleic acid sequence, e.g., the sequence of an HLA DQA and/or DQB gene, or a portion thereof (e.g., a SNP or a fragment of the gene), may be accomplished using any nucleic-acid based assay known in the art (see, e.g., Bunce M, et al. Phototyping: comprehensive DNA typing for HLA-A, B, C, DRB1, DRB3, DRB4, DRB5 & DQB1 by PCR with 144 primer mixes utilizing sequence-specific primers (PCR-SSP). Tissue Antigens 46, 355-367 (1995); Olerup O, Aldener A, Fogdell A. HLA-DQB1 and DQA1 typing by PCR amplification with sequence-specific primers in 2 hours. Tissue antigens 41, 119-134 (1993); Mullighan C G, Bunce M, Welsh K I. High-resolution HLA-DQB1 typing using the polymerase chain reaction and sequence-specific primers. Tissue-Antigens. 50, 688-92 (1997); Koskinen L, Romanos J, Kaukinen K, Mustalahti K, Korponay-Szabo I, et al. (2009) Cost-effective HLA typing with tagging SNPs predicts celiac disease risk haplotypes in the Finnish, Hungarian, and Italian populations. Immunogenetics 61: 247-256; and Monsuur A J, de Bakker P I, Zhernakova A, Pinto D, Verduijn W, et al. (2008) Effective detection of human leukocyte antigen risk alleles in celiac disease using tag single nucleotide polymorphisms. PLoS ONE 3: e2270; Koskinen L, Romanos J, Kaukinen K, Mustalahti K, Korponay-Szabo I, Barisani D, Bardella M T, Ziberna F, Vatta S, Szeles G et al: Cost-effective HLA typing with tagging SNPs predicts Celiac disease risk haplotypes in the Finnish, Hungarian, and Italian populations. Immunogenetics 2009, 61(4):247-256; Monsuur A J, de Bakker P I, Zhernakova A, Pinto D, Verduijn W, Romanos J, Auricchio R, Lopez A, van Heel D A, Crusius J B et al: Effective detection of human leukocyte antigen risk alleles in Celiac disease using tag single nucleotide polymorphisms. PLoS ONE 2008, 3(5):e2270).

Exemplary nucleic acid-based assays include, but are not limited to, PCR, restriction fragment length polymorphism identification (RFLPI), random amplified polymorphic detection (RAPD), amplified fragment length polymorphism detection (AFLPD), allele specific oligonucleotide (ASO) probes, hybridization to microarrays or beads, Sanger sequencing, Single-molecule real-time sequencing (Pacific Bio), Ion semiconductor (Ion Torrent sequencing), Pyrosequencing (454), Single molecule real time (SMRT) sequencing), Sequencing by synthesis (Illumina), and Sequencing by ligation (SOLiD sequencing). The assays may include the use of one or more nucleic acid probes or primers. The one or more probes or primers may be designed, e.g., to specifically bind to nucleic sequences within one or more HLA-DQA or DQB alleles. Methods for designing probes and primers are known in the art. The probes or primers may be attached to a detectable label. Any suitable detectable label is contemplated. Detectable labels include any composition detectable by spectroscopic, photochemical, biochemical, immunochemical, chemical, or other physical means, e.g., an enzyme, a radioactive label, a fluorophore, an electron dense reagent, biotin, digoxigenin, or a hapten. Such detectable labels are well-known in the art and can be detected through use of, e.g., an enzyme assay, a chromogenic assay, a luminometric assay, a fluorogenic assay, or a radioimmune assay. The reaction conditions to perform detection of the detectable label depend upon the detection method selected.

Gluten Peptide Treatment

Aspects of the disclosure relate to gluten peptide treatments and uses thereof in any one of the methods described herein. As used herein the term "gluten peptide" includes any peptide comprising a sequence derived from, or encompassed within, one or more of gluten proteins alpha ($\alpha$), beta ($\beta$), $\gamma$ ($\gamma$) and omega ($\omega$) gliadins, and low and high molecular weight (LMW and HMW) glutenins in wheat, B, C and D hordeins in barley, $\beta$, $\gamma$ and omega secalins in rye, and optionally avenins in oats, including deamidated variants thereof containing one or more glutamine to glutamate substitutions. In some embodiments, the gluten peptide(s) stimulate a CD4+ T cell specific response.

A gluten peptide may include one or more epitopes known to be recognized by a CD4$^+$ T cell in a subject with Celiac disease, e.g., PELP (SEQ ID NO: 12), PELPY (SEQ ID NO: 13), QPELPYP (SEQ ID NO: 64), PQPELPY (SEQ ID NO: 65), FPQPELP (SEQ ID NO: 66), PELPYPQ (SEQ ID NO: 67), FPQPELPYP (SEQ ID NO: 68), PYPQPELPY (SEQ ID NO: 14), PFPQPELPY (SEQ ID NO: 1), PQPELPYPQ (SEQ ID NO: 2), PFPQPEQPF (SEQ ID NO: 3), PQPEQP-FPW (SEQ ID NO: 4), PIPEQPQPY (SEQ ID NO: 5), PQPELPYPQ (SEQ ID NO: 2), FRPEQPYPQ (SEQ ID NO: 27), PQQSFPEQQ (SEQ ID NO: 28), IQPEQPAQL (SEQ ID NO: 29), QQPEQPYPQ (SEQ ID NO: 30), SQPEQEFPQ (SEQ ID NO: 31), PQPEQEFPQ (SEQ ID NO: 32), QQPEQPFPQ (SEQ ID NO: 33), PQPEQPFCQ (SEQ ID NO: 34), QQPFPEQPQ (SEQ ID NO: 35), PFPQPEQPF (SEQ ID NO: 3), PQPEQPFPW (SEQ ID NO:4), PFSEQEQPV (SEQ ID NO: 36), FSQQQESPF (SEQ ID NO: 37), PFPQPEQPF (SEQ ID NO:3), PQPEQP-FPQ (SEQ ID NO: 38), PIPEQPQPY (SEQ ID NO:5), PFPQPEQPF (SEQ ID NO:3), PQPEQPFPQ (SEQ ID NO:38), PYPEQEEPF (SEQ ID NO: 39), PYPEQEQPF (SEQ ID NO: 40), PFSEQEQPV (SEQ ID NO:36), EGS-FQPSQE (SEQ ID NO: 41), EQPQQPFPQ (SEQ ID NO: 42), EQPQQPYPE (SEQ ID NO: 43), QQGYYPTSPQ (SEQ ID NO: 44), EGSFQPSQE (SEQ ID NO:41), PQQS-FPEQE (SEQ ID NO: 45), or QGYYPTSPQ (SEQ ID NO: 46) (see, e.g., Sollid L M, Qiao S W, Anderson R P, Gianfrani C, Koning F. Nomenclature and listing of celiac disease relevant gluten epitopes recognized by CD4+ T cells. Immunogenetics. 2012; 64:455-60; PCT Publication Nos.: WO/2001/025793, WO/2003/104273, WO/2005/105129, and WO/2010/060155). Preferably, in some embodiments, the gluten peptides that comprise epitopes such as those set forth in SEQ ID NO: 12, 13, etc., also comprise additional amino acids flanking either or both sides of the epitope. Exemplary gluten peptides and methods for synthesizing such peptides are known in the art (see, e.g., PCT Publication Nos.: WO/2001/025793, WO/2003/104273, WO/2005/105129, and WO/2010/060155, which are incorporated herein by reference in their entirety). In some embodiments, the gluten peptide comprises PELP (SEQ ID NO: 12), PELPY (SEQ ID NO: 13), QPELPYP (SEQ ID NO: 64), PQPELPY (SEQ ID NO: 65), FPQPELP (SEQ ID NO: 66), or PELPYPQ (SEQ ID NO: 67) and is at least 8 or 9 amino acids in length.

In some embodiments, one or more glutamate residues of a gluten peptide may be generated by tissue transglutaminase (tTG) deamidation activity upon one or more glutamine residues of the gluten peptide. This deamidation of glutamine to glutamate can cause the generation of gluten peptides that can bind to HLA-DQ2 or -DQ8 molecules with high affinity. This reaction may occur in vitro by contacting the gluten peptide composition with tTG outside of the subject (e.g., prior to or during contact of a gluten peptide composition with a sample comprising T cells from a subject) or in vivo following administration through deamidation via tTG in the body. Deamidation of a peptide may also be accomplished by synthesizing a peptide de novo with glutamate residues in place of one or more glutamine residues, and thus deamidation does not necessarily require use of tTG. For example, PFPQPQLPY (SEQ ID NO: 15) could become PFPQPELPY (SEQ ID NO: 1) after processing by tTG. Conservative substitution of E with D is also contemplated herein (e.g., PFPQPELPY (SEQ ID NO: 1) could become PFPQPDLPY (SEQ ID NO: 26). Exemplary peptides including an E to D substitution include peptides comprising or consisting of PFPQPDLPY (SEQ ID NO: 26), PQPDLPYPQ (SEQ ID NO: 69), PFPQPDQPF (SEQ ID NO: 70), PQPDQPFPW (SEQ ID NO: 71), PIPDQPQPY (SEQ ID NO: 72), LQPFPQPDLPYPQPQ (SEQ ID NO: 73), QPFPQPDQPFPWQP (SEQ ID NO: 74), or PQQPIP-DQPQPYPQQ (SEQ ID NO: 75). Such substituted peptides can be the gluten peptides of any of the methods and compositions provided herein. Accordingly, gluten peptides that have not undergone deamidation are also contemplated herein (e.g., gluten peptides comprising or consisting of PQLP (SEQ ID NO: 16), PQLPY (SEQ ID NO: 17), QPQLPYP (SEQ ID NO: 76), PQPQLPY (SEQ ID NO: 77), FPQPQLP (SEQ ID NO: 78), PQLPYPQ (SEQ ID NO: 79), FPQPQLPYP (SEQ ID NO: 80), PYPQPQLPY (SEQ ID NO: 18), PFPQPQLPY (SEQ ID NO: 15), PQPQLPYPQ (SEQ ID NO: 19), PFPQPQQPF (SEQ ID NO: 20), PQPQQPFPW (SEQ ID NO: 21), PIPQQPQPY (SEQ ID NO: 22), LQPFPQPQLPYPQPQ (SEQ ID NO: 23), QPFPQPQQPFPWQP (SEQ ID NO: 24), or PEQPIPQQPQPYPQQ (SEQ ID NO: 25), PQPQLPYPQ (SEQ ID NO:19), FRPQQPYPQ (SEQ ID NO: 47), PQQS-FPQQQ (SEQ ID NO: 48), IQPQQPAQL (SEQ ID NO: 49), QQPQQPYPQ (SEQ ID NO: 50), SQPQQQFPQ (SEQ ID NO: 51), PQPQQQFPQ (SEQ ID NO: 52), QQPQQPFPQ (SEQ ID NO: 53), PQPQQPFCQ (SEQ ID NO: 54), QQP-FPQQPQ (SEQ ID NO: 55), PFPQPQQPF (SEQ ID NO:20), PQPQQPFPW (SEQ ID NO: 21), PFSQQQQPV (SEQ ID NO: 56), FSQQQQSPF (SEQ ID NO: 57), PFPQPQQPF (SEQ ID NO:20), PQPQQPFPQ (SEQ ID NO: 58), PIPQQPQPY (SEQ ID NO:22), PFPQPQQPF (SEQ ID NO:20), PQPQQPFPQ (SEQ ID NO:58), PYPEQQEPF (SEQ ID NO: 59), PYPEQQQPF (SEQ ID NO: 60), PFSQQQQPV (SEQ ID NO:56), QGSFQPSQQ (SEQ ID NO: 61), QQPQQPFPQ (SEQ ID NO:53), QQPQQPYPQ (SEQ ID NO:50), QQGYYPTSPQ (SEQ ID NO:53), QGSFQPSQQ (SEQ ID NO:61), PQQSFPQQQ (SEQ ID NO:48), QGYYPTSPQ (SEQ ID NO:56), LQP-FPQPELPYPQPQ (SEQ ID NO: 62), QPFPQPQQPFP-WQP (SEQ ID NO:24), or PQQPIPQQPQPYPQQ (SEQ ID NO: 63)). In some embodiments, the gluten peptide comprises PQLP (SEQ ID NO: 16), PQLPY (SEQ ID NO: 17), QPQLPYP (SEQ ID NO: 76), PQPQLPY (SEQ ID NO: 77), FPQPQLP (SEQ ID NO: 78), or PQLPYPQ (SEQ ID NO: 79) and is at least 8 or 9 amino acids in length.

A gluten peptide may also be an analog of any of the peptides described herein. Preferably, in some embodiments the analog is recognized by a CD4+ T cell that recognizes one or more of the epitopes listed herein. Exemplary analogs comprise a peptide that has a sequence that is, e.g., 75%, 80%, 85%, 90%, 95%, 96%, 97%, 98%, or 99% homologous to the epitopes specifically recited herein. In some embodiments, the analogs comprise a peptide that is, e.g., 75%, 80%, 85%, 90%, 95%, 96%, 97%, 98%, or 99% homologous to the peptides specifically recited herein. Analogs may also be a variant of any of the peptides provided, such variants can include conservative amino acid substitution variants, e.g., E to D substitution.

In some embodiments, analogs may include one or more amino acid substitutions as shown in Table 1 (see, e.g., Anderson et al. Antagonists and non-toxic variants of the dominant wheat gliadin T cell epitope in coeliac disease. Gut. 2006 April; 55(4): 485-491; and PCT Publication WO2003104273, the contents of which are incorporated herein by reference). The gluten peptides provided herein include analogs of SEQ ID NO:68 comprising one or more of the listed amino acid substitutions. In some embodiments, the analog is an analog of SEQ ID NO: 68 comprising one of the amino acid substitutions provided in Table 1 below. Preferably, analogs generate a T cell response as described herein.

TABLE 1

| Exemplary substitutions in the epitope FPQPELPYP (SEQ ID NO: 68) | | | | | | | | | |
|---|---|---|---|---|---|---|---|---|---|
| Amino acid in epitope | F | P | Q | P | E | L | P | Y | P |
| Exemplary Substitutions | A, G, H, I, L, M P, S, T, W, Y | A, F, I, M, S, T, V, W, Y | A, F, G, H, I, L, M, S, T, V | — | D | M | S | I, S, V, W | S, T, Y |

The length of the peptide may vary. In some embodiments, peptides are, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length. In some embodiments, peptides are, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or fewer amino acids in length. In some embodiments, peptides are, e.g., 4-1000, 4-500, 4-100, 4-50, 4-40, 4-30, or 4-20 amino acids in length. In some embodiments, peptides are 4-20, 5-20, 6-20, 7-20, 8-20, 9-20, 10-20, 11-20, 12-20, 13-20, 14-20, or 15-20 amino acids in length. In some embodiments, peptides are e.g., 5-30, 10-30, 15-30 or 20-30 amino acids in length. In some embodiments, peptides are 4-50, 5-50, 6-50, 7-50, 8-50, 9-50, 10-50, 11-50, 12-50, 13-50, 14-50, or 15-50 amino acids in length. In some embodiments, peptides are 8-50 amino acids in length.

In some embodiments, the gluten peptide treatment is a composition comprising at least one or one or more gluten peptide(s). In some embodiments, any one of the methods described herein comprises administering the composition to a subject (e.g., a subject having or suspected of having Celiac disease).

In some embodiments, the gluten peptide treatment comprises a composition comprising at least one peptide comprising at least one amino acid sequence selected from PFPQPELPY (SEQ ID NO: 1), PQPELPYPQ (SEQ ID NO: 2), PFPQPEQPF (SEQ ID NO: 3), PQPEQPFPW (SEQ ID NO: 4), PIPEQPQPY (SEQ ID NO: 5) and EQPIPEQPQ (SEQ ID NO: 6). In some embodiments, the gluten peptide treatment comprises a composition comprising at least one of: (i) a first peptide comprising the amino acid sequence PFPQPELPY (SEQ ID NO: 1) and PQPELPYPQ (SEQ ID NO: 2), (ii) a second peptide comprising the amino acid sequence PFPQPEQPF (SEQ ID NO: 3) and PQPEQPFPW (SEQ ID NO: 4), and (iii) a third peptide comprising the amino acid sequence PIPEQPQPY (SEQ ID NO: 5) and EQPIPEQPQ (SEQ ID NO: 6). "First", "second", and "third" are not meant to imply an order of use or importance, unless specifically stated otherwise. In some embodiments, the composition comprises the first and second peptide, the first and third peptide, or the second and third peptide. In some embodiments, the composition comprises the first and second peptide. In some embodiments, the composition comprises the first, second, and third peptide. In some embodiments, the first peptide comprises the amino acid sequence LQPFPQPELPYPQPQ (SEQ ID NO: 62); the second peptide comprises the amino acid sequence QPFPQPEQPFPWQP (SEQ ID NO: 7); and/or the third peptide comprises the amino acid sequence PEQPIPEQPQPYPQQ (SEQ ID NO: 8).

In some embodiments, it may be desirable to utilize the non-deamidated forms of such peptides, e.g., if the peptides are contained within a composition for administration to a subject where tissue transglutaminase will act in situ (see, e.g., Øyvind Molberg, Stephen McAdam, Knut E. A. Lundin, Christel Kristiansen, Helene Arentz-Hansen, Kjell Kett and Ludvig M. Sollid. T cells from celiac disease lesions recognize gliadin epitopes deamidated in situ by endogenous tissue transglutaminase. Eur. J. Immunol. 2001. 31: 1317-1323). Accordingly, in some embodiments, the composition comprises at least one of: (i) a first peptide comprising the amino acid sequence PFPQPQLPY (SEQ ID NO: 15) and PQPQLPYPQ (SEQ ID NO: 19), (ii) a second peptide comprising the amino acid sequence PFPQPQQPF (SEQ ID NO: 20) and PQPQQPFPW (SEQ ID NO: 21), and (iii) a third peptide comprising the amino acid sequence PIPQQPQPY (SEQ ID NO: 22). In some embodiments, the first peptide comprises the amino acid sequence LQPFPQPQLPYPQPQ (SEQ ID NO:23); the second peptide comprises the amino acid sequence QPFPQPQQPFPWQP (SEQ ID NO:24); and/or the third peptide comprises the amino acid sequence PQQPIPQQPQPYPQQ (SEQ ID NO: 63). In some embodiments, the peptides are 8-30 amino acids in length.

Modifications to a gluten peptide are also contemplated herein. This modification may occur during or after translation or synthesis (for example, by farnesylation, prenylation, myristoylation, glycosylation, palmitoylation, acetylation, phosphorylation (such as phosphotyrosine, phosphoserine or phosphothreonine), amidation, pyrolation, derivatisation by known protecting/blocking groups, proteolytic cleavage, linkage to an antibody molecule or other cellular ligand, and the like). Any of the numerous chemical modification methods known within the art may be utilized including, but not limited to, specific chemical cleavage by cyanogen bromide, trypsin, chymotrypsin, papain, V8 protease, NaBH4, acetylation, formylation, oxidation, reduction, metabolic synthesis in the presence of tunicamycin, etc.

The phrases "protecting group" and "blocking group" as used herein, refers to modifications to the peptide, which protect it from undesirable chemical reactions, particularly chemical reactions in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methoxysuccinyl; aromatic urethane protecting groups such as, for example, benzyloxycarbonyl (Cbz); aliphatic urethane protecting groups such as, for example, t-butoxycarbonyl (Boc) or 9-fluorenylmethoxy-carbonyl (FMOC); pyroglutamate and amidation. Many other modifications providing increased potency, prolonged activity, ease of purification, and/or increased half-life will be known to the person skilled in the art.

The peptides may comprise one or more modifications, which may be natural post-translation modifications or artificial modifications. The modification may provide a chemical moiety (typically by substitution of a hydrogen, for example, of a C—H bond), such as an amino, acetyl, acyl, amide, carboxy, hydroxy or halogen (for example, fluorine) group, or a carbohydrate group. Typically, the modification may be present on the N- and/or C-terminus. Furthermore, one or more of the peptides may be PEGylated, where the PEG (polyethyleneoxy group) provides for enhanced lifetime in the blood stream. One or more of the peptides may also be combined as a fusion or chimeric protein with other proteins, or with specific binding agents that allow targeting to specific moieties on a target cell.

A gluten peptide may also be chemically modified at the level of amino acid side chains, of amino acid chirality, and/or of the peptide backbone.

Particular changes can be made to a gluten peptide to improve resistance to degradation or optimize solubility properties or otherwise improve bioavailability compared to the parent gluten peptide, thereby providing gluten peptides having similar or improved therapeutic, diagnostic and/or pharmacokinetic properties. A preferred such modification, in some embodiments, includes the use of an N-terminal acetyl group or pyroglutamate and/or a C-terminal amide. Such modifications have been shown in the art to significantly increase the half-life and bioavailability of peptides compared to the peptides having a free N- and C-terminus (see, e.g., PCT Publication No.: WO/2010/060155). In some embodiments, the first, second and/or third peptides comprise an N-terminal acetyl group or pyroglutamate group and/or a C-terminal amide group. In some embodiments, the first peptide comprises the amino acid sequence ELQPFPQPELPYPQPQ (SEQ ID NO: 9), wherein the N-terminal E is a pyroglutamate; the second peptide comprises the amino acid sequence EQPFPQPEQPFPWQP (SEQ ID NO: 10), wherein the N-terminal E is a pyroglutamate; and/or the third peptide comprises the amino acid sequence EPEQPIPEQPQPYPQQ (SEQ ID NO: 11), wherein the N-terminal E is a pyroglutamate. In some embodiments, the first peptide comprises the amino acid sequence ELQPFPQPELPYPQPQ (SEQ ID NO: 9), wherein the N-terminal E is a pyroglutamate, and wherein the peptide contains a C-terminal amide group; the second peptide comprises the amino acid sequence EQPFPQPEQPFPWQP (SEQ ID NO: 10), wherein the N-terminal E is a pyroglutamate, and wherein the peptide contains a C-terminal amide group; and/or the third peptide comprises the amino acid sequence EPEQPIPEQPQPYPQQ (SEQ ID NO: 11), wherein the N-terminal E is a pyroglutamate, and wherein the peptide contains a C-terminal amide group. In some embodiments, the first peptide consists of the amino acid sequence ELQPFPQPELPYPQPQ (SEQ ID NO: 9), wherein the N-terminal E is a pyroglutamate, and wherein the peptide contains a C-terminal amide group; the second peptide consists of the amino acid sequence EQPFPQPEQPFPWQP (SEQ ID NO: 10), wherein the N-terminal E is a pyroglutamate, and wherein the peptide contains a C-terminal amide group; and/or the third peptide consists of the amino acid sequence EPEQPIPEQPQPYPQQ (SEQ ID NO: 11), wherein the N-terminal E is a pyroglutamate, and wherein the peptide contains a C-terminal amide group.

In a particular embodiment, a composition comprising a first peptide comprising the amino acid sequence ELQPFPQPELPYPQPQ (SEQ ID NO:9), wherein the N-terminal glutamate is a pyroglutamate and the C-terminal glutamine is amidated (i.e., the free C-terminal COO is amidated); a second peptide comprising the amino acid sequence EQPFPQPEQPFPWQP (SEQ ID NO:10), wherein the N-terminal glutamate is a pyroglutamate and the C-terminal proline is amidated (i.e., the free C-terminal COO is amidated); and a third peptide comprising the amino acid sequence EPEQPIPEQPQPYPQQ (SEQ ID NO:11), wherein the N-terminal glutamate is a pyroglutamate and the C-terminal glutamine is amidated (i.e., the free C-terminal COO is amidated) is contemplated. In some embodiments, the first, second and/or third peptides consist essentially of or consist of the amino acid sequence of SEQ ID NO: 9, 10, or 11, respectively. Compositions are further described herein.

In another embodiment, a composition comprising first peptide comprising the amino acid sequence PFPQPELPY (SEQ ID NO:1) and the amino acid sequence PQPELPYPQ (SEQ ID NO:2), optionally wherein the N-terminus comprises a pyroglutamate (e.g., any N-terminal glutamate is a pyroglutamate) and the C-terminus is amidated (e.g., any C-terminal glutamine is amidated); a second peptide comprising the amino acid sequence PFPQPEQPF (SEQ ID NO:3) and the amino acid sequence PQPEQPFPW (SEQ ID NO:4), optionally wherein the N-terminus comprises a pyroglutamate (e.g., any N-terminal glutamate is a pyroglutamate) and the C-terminus is amidated (e.g., any C-terminal proline is amidated); and a third peptide comprising the amino acid sequence EQPIPEQPQ (SEQ ID NO:6) and the amino acid sequence PIPEQPQPY (SEQ ID NO:5), optionally wherein the N-terminus comprises a pyroglutamate (e.g., any N-terminal glutamate is a pyroglutamate) and the C-terminus is amidated (e.g., any C-terminal glutamine is amidated) is contemplated.

Certain peptides described herein may exist in particular geometric or stereoisomeric forms. The present disclosure contemplates all such forms, including cis-(Z) and trans-(E) isomers, R- and S-enantiomers, diastereomers, (D)-isomers, (L)-isomers, the racemic mixtures thereof, and other mixtures thereof, as, falling within the scope of the disclosure. Additional asymmetric carbon atoms may be present in a substituent, such as an alkyl group. All such isomers, as well as mixtures thereof, are intended to be included in this disclosure.

In another example, to prevent cleavage by peptidases, any one or more of the peptides may include a non-cleavable peptide bond in place of a particularly sensitive peptide bond to provide a more stable peptide. Such non-cleavable peptide bonds may include beta amino acids.

In certain embodiments, any one or more of the peptides may include a functional group, for example, in place of the scissile peptide bond, which facilitates inhibition of a serine-, cysteine- or aspartate-type protease, as appropriate. For example, the disclosure includes a peptidyl diketone or a peptidyl keto ester, a peptide haloalkylketone, a peptide sulfonyl fluoride, a peptidyl boronate, a peptide epoxide, a peptidyl diazomethane, a peptidyl phosphonate, isocoumarins, benzoxazin-4-ones, carbamates, isocyantes, isatoic anhydrides or the like. Such functional groups have been provided in other peptide molecules, and general routes for their synthesis are known.

The peptides may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Peptide Production

The peptides described herein (e.g., gluten peptides) can be prepared in any suitable manner. For example, the peptides can be recombinantly and/or synthetically produced.

The peptides may be synthesised by standard chemistry techniques, including synthesis by an automated procedure using a commercially available peptide synthesiser. In general, peptides may be prepared by solid-phase peptide synthesis methodologies which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, and as outlined above, various groups may be introduced into the peptide of the composition during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, use RNA as a template; whereas "coupled" and "linked" systems start with DNA templates, which are transcribed into RNA then translated.

Alternatively, the peptides may be produced by transfecting host cells with expression vectors that comprise a polynucleotide(s) that encodes one or more peptides.

For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, Saccharomyces or Pichia), bacteria (for example, E. coli, P. pastoris, or B. subtilis), insect cells (for example, baculovirus in Sf9 cells) or other cells under the control of appropriate promoters using conventional techniques. Following transformation of the suitable host strain and growth of the host strain to an appropriate cell density, the cells can be harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the E. coli lac or trp, the phage lambda PL promoter and other promoters known to control expression of genes in prokaryotic or eukaryotic cells or in viruses. The expression vector may also contain a ribosome binding site for translation initiation and a transcription terminator. The expression vectors may also include an origin of replication and a selectable marker, such as the ampicillin resistance gene of E. coli to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well-known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred in some embodiments that recombinant techniques be used. To produce a glycosylated peptide, it is preferred in some embodiments that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesised from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent. In some embodiments, the pharmaceutically acceptable salt is a trifluoroacetate (TFA) salt or an acetate salt.

Dosage and Administration

Compositions

The disclosure also provides compositions comprising gluten peptides, e.g., for treatment, for diagnostic methods, for therapeutic efficacy methods, among others. In some embodiments, the composition comprising gluten peptides is a gluten peptide treatment. In some embodiments, the composition comprising gluten peptides is a first composition. In some embodiments, the composition comprising gluten peptides is a second composition.

In some embodiments, the composition comprises a first peptide comprising the amino acid sequence ELQP-FPQPELPYPQPQ (SEQ ID NO:9), wherein the N-terminal glutamate is a pyroglutamate and the carboxyl group of the C-terminal glutamine is amidated; a second peptide comprising the amino acid sequence EQPFPQPEQPFPWQP (SEQ ID NO:10), wherein the N-terminal glutamate is a pyroglutamate and the carboxyl group of the C-terminal proline is amidated; and a third peptide comprising the amino acid sequence EPEQPIPEQPQPYPQQ (SEQ ID NO:11), wherein the N-terminal glutamate is a pyroglutamate and the carboxyl group of the C-terminal glutamine is amidated. In some embodiments, the composition is a vaccine composition.

The disclosure additionally provides a composition comprising a first peptide comprising the amino acid sequence PFPQPELPY (SEQ ID NO: 1) and the amino acid sequence PQPELPYPQ (SEQ ID NO: 2), optionally wherein the N-terminus comprises a pyroglutamate (e.g., any N-terminal glutamate is a pyroglutamate) and the C-terminus is amidated (e.g., any C-terminal glutamine is amidated); a second peptide comprising the amino acid sequence PFPQPEQPF (SEQ ID NO: 3) and the amino acid sequence PQPEQPFPW (SEQ ID NO:4), optionally wherein the N-terminus comprises a pyroglutamate (e.g., any N-terminal glutamate is a pyroglutamate) and the C-terminus is amidated (e.g., any C-terminal proline is amidated); and a third peptide comprising the amino acid sequence EQPIPEQPQ (SEQ ID NO:6) and the amino acid sequence PIPEQPQPY (SEQ ID NO:5), optionally wherein the N-terminus comprises a pyroglutamate (e.g, any N-terminal glutamate is a pyroglutamate) and the C-terminus is amidated (e.g., any C-terminal glutamine is amidated). In some embodiments, the composition is a vaccine composition.

As used herein, the term "vaccine" refers to a composition comprising peptide(s) that can be administered to a subject having Celiac disease to modulate the subject's response to gluten. The vaccine may reduce the immunological reactivity of a subject towards gluten. Preferably, the vaccine induces tolerance to gluten.

Without being bound by any theory, administration of the vaccine composition to a subject may induce tolerance by clonal deletion of gluten-specific effector T cell populations, for example, gluten-specific CD4$^+$ T cells, or by inactivation (anergy) of said T cells such that they become less responsive, preferably, unresponsive to subsequent exposure to gluten (or peptides thereof). Deletion or inactivation of said T cells can be measured, for example, by contacting ex vivo a sample comprising said T cells with gluten or a peptide thereof and measuring the response of said T cells to the gluten or peptide thereof. An exemplary T cell response measurement is measurement of the level of interferon-gamma (IFN-γ, see, e.g., NCBI Gene ID 3458 and Protein ID NP_000610.2) in the sample after contact with the gluten or peptide thereof. A decreased level of IFN-γ may indicate deletion or inactivation of said T cells. The level of IFN-γ can be measured using any method known to those of skill in the art, e.g., using immuno-based detection methods such as Western blot or enzyme-linked immunosorbent assay (ELISA).

Alternatively, or in addition, administration of the vaccine composition may modify the cytokine secretion profile of the subject (for example, result in decreased IL-4, IL-2, TNF-α and/or IFN-γ, and/or increased IL-10). The vaccine composition may induce suppressor T cell subpopulations, for example Treg cells, to produce IL-10 and/or TGF-β and thereby suppress gluten-specific effector T cells. The cytokine secretion profile of the subject can be measured using any method known to those of skill in the art, e.g., using immuno-based detection methods such as Western blot or enzyme-linked immunosorbent assay (ELISA).

The vaccine composition of the disclosure can be used for prophylactic treatment of a subject capable of developing Celiac disease and/or used in ongoing treatment of a subject who has Celiac disease. In some embodiments, the composition is for use in treating Celiac disease in a subject.

Dosage

The actual amount administered (e.g., dose or dosage) and the rate and time-course of administration of the gluten peptide composition may depend upon the HLA genotype of the subject. In some embodiments of any one of the methods described herein, the method comprises adjusting or selecting a dose of a gluten peptide composition, e.g., gluten peptide treatment for a subject based on the HLA genotype of the subject. In some embodiments of any one of the methods described herein, the method comprises decreasing a dose of the gluten peptide composition, e.g., gluten peptide treatment if the subject has a homozygous HLA-DQ2.5 genotype or maintaining or increasing the dose of the gluten peptide treatment if the subject has a non-homozygous HLA-DQ2.5 genotype.

In some embodiments of any one of the methods described herein, the method comprises measuring a level of at least one circulating cytokine or chemokine in a subject that has or is suspected of having Celiac disease, wherein the subject has been administered a first composition comprising at least one gluten peptide in an amount selected based on a human leukocyte antigen (HLA) genotype of the subject, and assessing the likelihood the subject has Celiac disease.

In some embodiments of any one of the methods described herein, the method comprises assessing tolerance to a gluten peptide in a subject having Celiac disease, the method comprising: measuring a level of at least one circulating cytokine or chemokine in a subject having Celiac disease, wherein the subject has been administered a first composition comprising at least one gluten peptide in an amount selected based on a human leukocyte antigen (HLA) genotype of the subject, and assessing the tolerance of the subject to the at least one gluten peptide based on the measuring.

HLA genotypes are further described herein. The dose may be decreased, e.g., by decreasing the amount of gluten peptide treatment administered to the subject or by decreasing the rate of administration of the gluten peptide treatment to the subject (e.g., by separating each administration by a longer period of time).

In some embodiments, the dose is adjusted or selected for a subject such that the amount is sufficient to provide the desired therapeutic or physiological effect when administered under appropriate or sufficient conditions without causing severe adverse effects. In some embodiments, when the gluten peptide treatment is a composition comprising a first peptide comprising the amino acid sequence ELQPFPQPELPYPQPQ (SEQ ID NO:9), wherein the N-terminal glutamate is a pyroglutamate and the carboxyl group of the C-terminal glutamine is amidated; a second peptide comprising the amino acid sequence EQPFPQPEQPFPWQP (SEQ ID NO:10), wherein the N-terminal glutamate is a pyroglutamate and the carboxyl group of the C-terminal proline is amidated; and a third peptide comprising the amino acid sequence EPEQPIPEQPQPYPQQ (SEQ ID NO:11), wherein the N-terminal glutamate is a pyroglutamate and the carboxyl group of the C-terminal glutamine is amidated, the dose to be adjusted is 150 micrograms of the peptides provided herein (i.e., 50 micrograms of the first peptide and an equimolar amount of each of the second and third peptides). In some embodiments, the dose to be adjusted is 26.5 nmol of each of the first, second, and third peptides. Methods for producing equimolar peptide compositions are known in the art and provided herein (see, e.g., Example 1 and Muller et al. Successful immunotherapy with T-cell epitope peptides of bee venom phospholipase A2 induces specific T-cell anergy in patient allergic to bee venom. J. Allergy Clin. Immunol. Vol. 101, Number 6, Part 1: 747-754 (1998)). In some embodiments, the dose to be adjusted is 300 micrograms of the peptides provided herein (i.e., 100 micrograms of the first peptide and an equimolar amount of each of the second and third peptides). In some embodiments, the dose to be adjusted is administered in sterile sodium chloride 0.9% USP as a bolus intradermal injection.

In some embodiments of any one of the methods provided, the dose is or is decreased to less than 300 micrograms of the peptides if the subject has a homozygous HLA-DQ2.5 genotype. In some embodiments of any one of the methods provided, the dose is or is decreased to less than 150 micrograms if the subject has a homozygous HLA-DQ2.5 genotype. In some embodiments of any one of the methods provided, the dose is or is increased to up to 300 micrograms if the subject has a heterozygous HLA-DQ2.5 genotype.

In some embodiments of any one of the methods provided, the dose is selected to be up to 300 micrograms if the subject has a heterozygous HLA-DQ2.5 genotype. In some embodiments of any one of the methods provided herein, the amount selected based on HLA-DQ2.5 genotype is any one of the foregoing. In some embodiments, the selected dose for a subject having a homozygous DQ2.5 genotype is less than the dose that would be selected for a subject having a heterozygous DQ2.5 genotype. In some embodiments, the selected dose for a subject having a heterozygous DQ2.5 genotype is more than the dose that would be selected for a subject having a homozygous DQ2.5 genotype.

In some embodiments, the dose that is adjusted or selected for a subject is believed to modify a T cell response, e.g., by inducing immune tolerance, to wheat, barley and rye in the subject, and preferably wheat, barley, rye and oats. Thus, a subject treated according to the disclosure preferably is able to eat at least wheat, rye, barley and optionally oats without a significant T cell response which would normally lead to clinical manifestations of active Celiac disease.

In some embodiments, it is advantageous to formulate the active in a dosage unit form for ease of administration and uniformity of dosage. "Dosage unit form" as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms are dictated by and directly dependent on the unique characteristics of the active agent and the particular therapeutic effect to be achieved, and the limitations inherent in the art of compounding such an active agent for the treatment of subjects. Examples of dosage units include sealed ampoules and vials and may be stored in a freeze-dried condition requiring only the addition of the sterile liquid carrier immediately prior to use.

The composition may also be included in a container, pack, or dispenser together with instructions for administration.

The actual amount administered (or dose or dosage) and the rate and time-course of administration are as provided herein.

The administration may occur at least once, e.g., once or twice a week. In some embodiments, a composition described herein is administered once or twice a week. In some embodiments, a composition described herein is administered for 3, 4 or 8 weeks. In some embodiments, a composition described herein is administered once a week for 8 weeks. In some embodiments, a composition described herein is administered once a week for 3 weeks. In some embodiments, a composition described herein is administered twice a week for 4 weeks. In some embodiments, a composition described herein is administered twice a week for 8 weeks. In some embodiments, the administration occurs 3, 8 or 16 times.

Kits

Another aspect of the disclosure relates to kits. In some embodiments, the kit comprises a composition comprising the peptides as described herein. The peptides can be contained within the same container or separate containers. In some embodiments, the kit can further comprise a placebo. In some embodiments, the peptide or ptides may be contained within the container(s) (e.g., dried onto the wall of the container(s)). In some embodiments, the peptides are contained within a solution separate from the container, such that the peptides may be added to the container at a subsequent time. In some embodiments, the peptides are in lyophilized form in a separate container, such that the peptides may be reconstituted and added to the container at a subsequent time.

In some embodiments, the kit further comprises instructions for reconstitution, mixing, administration, etc. In some embodiments, the instructions include the methods described herein. Instructions can be in any suitable form, e.g., as a printed insert or a label.

Pharmaceutically Acceptable Carriers

The composition may include a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure. In some embodiments, the pharmaceutically acceptable carrier is a sodium chloride solution (e.g., sodium chloride 0.9% USP).

The carrier can be any of those conventionally used and is limited only by chemico-physical considerations, such as solubility and lack of reactivity with the active agent, and by the route of administration. Suitable carriers for this disclosure include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Techniques for preparing pharmaceutical compositions are generally known in the art as exemplified by Remington's Pharmaceutical Sciences, 16th Ed. Mack Publishing Company, 1980.

Administration preferably is intradermal administration. Thus, the composition of the disclosure may be in a form suitable for intradermal injection. In some embodiments, the composition of the disclosure is in the form of a bolus for intradermal injection.

Injectables

The pharmaceutical composition(s) may be in the form of a sterile injectable aqueous or oleagenous suspension. In some embodiments, the composition is formulated as a sterile, injectable solution. This suspension or solution may be formulated according to known methods using those suitable dispersing or wetting agents and suspending agents which have been mentioned above. The sterile injectable preparation may be a suspension in a non-toxic parenterally-acceptable diluent or solvent, for example as a solution in 1,3-butanediol. Among the acceptable carriers that may be employed are water, Ringer's solution and isotonic sodium chloride solution. In some embodiments, the composition is formulated as a sterile, injectable solution, wherein the solution is a sodium chloride solution (e.g., sodium chloride 0.9% USP). In some embodiments, the composition is formulated as a bolus for intradermal injection.

Examples of appropriate delivery mechanisms for intradermal administration include, but are not limited to, implants, depots, needles, capsules, and osmotic pumps.

Methods of Treatment

Aspects of the disclosure relate to use of the compositions described herein for treating a subject having, suspected of having or at risk of having Celiac disease.

As used herein, the terms "treat", "treating", and "treatment" include abrogating, inhibiting, slowing, or reversing the progression of a disease or condition, or ameliorating or preventing a clinical symptom of the disease (for example, Celiac disease). Treatment may include induction of immune tolerance (for example, to gluten or peptide(s) thereof), modification of the cytokine secretion profile of the subject and/or induction of suppressor T cell subpopulations to secrete cytokines. Thus, a subject treated according to the disclosure preferably is able to eat at least wheat, rye, barley and optionally oats without a significant T cell response which would normally lead to symptoms of Celiac disease.

Subjects

A subject may include any subject that has or is suspected of having Celiac disease. Preferably, the subject is a human. In some embodiments, the subject has one or more HLA-DQA and HLA-DQB susceptibility alleles encoding HLA-DQ2.5 (DQA1*05 and DQB1*02), HLA-DQ2.2 (DQA1*02 and DQB1*02) or HLA-DQ8 (DQA1*03 and DQB1*0302). In some embodiments, the subject is HLA-DQ2.5 positive (i.e., has both susceptibility alleles DQA1*05 and DQB1*02). In some embodiments, a subject may have a family member that has one or more HLA-DQA and HLA-DQB susceptibility alleles encoding HLA-DQ2.5 (DQA1*05 and DQB1*02), HLA-DQ2.2 (DQA1*02 and DQB1*02) or HLA-DQ8 (DQA1*03 and DQB1*0302). In some embodiments of any one of the methods provided herein, the subject is on a gluten-free diet.

Exemplary methods for identifying subjects having or suspected of having Celiac disease include, but are not limited to, intestinal biopsy, serology (measuring the levels of one or more antibodies present in the serum), genotyping (see, e.g., Walker-Smith J A, et al. Arch Dis Child 1990), and measurement of a T cell response. Such methods may be performed as part of any one of the methods described herein or after any one of the methods described herein (e.g., as a companion diagnostic), or before any one of the methods described herein (e.g., as a first-pass screen to eliminate certain subjects before use of the methods described herein, e.g., eliminating those that do not have one or more HLA-DQA and HLA-DQB susceptibility alleles).

Detection of serum antibodies (serology) is contemplated. The presence of such serum antibodies can be detected using methods known to those of skill in the art, e.g., by ELISA, histology, cytology, immunofluorescence or western blotting. Such antibodies include, but are not limited to: IgA anti-endomysial antibody (IgA EMA), IgA anti-tissue transglutaminase 2 antibody (IgA tTG), IgA anti-deamidated gliadin peptide antibody (IgA DGP), and IgG anti-deamidated gliadin peptide antibody (IgG DGP). Deamidated gliadin peptide-IgA (DGP-IgA) and deamidated gliadin peptide-IgG (DGP-IgG) can be evaluated with commercial kits (e.g. INV 708760, 704525, and 704520, INOVA Diagnostics, San Diego, Calif.).

IgA EMA: IgA endomysial antibodies bind to endomysium, the connective tissue around smooth muscle, producing a characteristic staining pattern that is visualized by indirect immunofluorescence. The target antigen has been identified as tissue transglutaminase (tTG or transglutaminase 2). IgA endomysial antibody testing is thought to be moderately sensitive and highly specific for untreated (active) Celiac disease.

IgA tTG: The antigen is tTG. Anti-tTG antibodies are thought to be highly sensitive and specific for the diagnosis of Celiac disease. Enzyme-linked immunosorbent assay (ELISA) tests for IgA anti-tTG antibodies are now widely available and are easier to perform, less observer-dependent, and less costly than the immunofluorescence assay used to detect IgA endomysial antibodies. The diagnostic accuracy of IgA anti-tTG immunoassays has been improved further by the use of human tTG in place of the nonhuman tTG preparations used in earlier immunoassay kits. Kits for IgA tTG are commercially available (INV 708760, 704525, and 704520, INOVA Diagnostics, San Diego, Calif.).

Deamidated gliadin peptide-IgA (DGP-IgA) and deamidated gliadin peptide-IgG (DGP-IgG) are also contemplated herein and can be evaluated with commercial kits (INV 708760, 704525, and 704520, INOVA Diagnostics, San Diego, Calif.).

T cell response tests are also contemplated as other testing. In some embodiments, a T cell response test comprises contacting a sample comprising a T cell with at least one gluten peptide and measuring a T cell response in the sample. In some embodiments, a T cell response is measured by measuring a level of IFN-γ, where an increased level of IFN-γ compared to a control level (e.g., a level of IFN-γ in a sample that has not been contacted with a gluten peptide) may identify a subject as having Celiac disease. T cell response tests are known in the art (see, e.g., PCT Publication Nos.: WO/2001/025793, WO/2003/104273, WO/2005/105129, and WO/2010/060155).

Diagnostic Methods

One aspect of the disclosure relates to methods of identifying (e.g., diagnosing) subjects, such as subjects having or suspected of having Celiac disease.

In some embodiments, the method comprises measuring a level of at least one circulating cytokine or chemokine in a subject that has or is suspected of having celiac disease, wherein the subject has been administered a composition comprising at least one gluten peptide as described herein. In some embodiments, the method further comprises assessing the likelihood the subject has Celiac disease. In some embodiments, assessing comprises comparing the level of the at least one circulating cytokine or chemokine to a control level of the at least one circulating cytokine or chemokine. Levels as used herein can be absolute or relative amounts. In some embodiments, assessing comprises determining the ratio of the level of the at least one circulating cytokine or chemokine to the control level. In some embodiments, the control level of the at least one circulating cytokine or chemokine is a baseline level of the circulating cytokine or chemokine. In some embodiments, the baseline level is the level of the circulating cytokine or chemokine in the subject prior to the administration of the one or more gluten peptides. In some embodiments of any one of the methods provided herein, the method can further comprise the step of determining a baseline level of the circulating cytokine or chemokine in the subject.

In some embodiments, an elevated level of the at least one circulating cytokine or chemokine compared to a control level, such as a baseline level, of the at least one circulating cytokine or chemokine indicates that the subject has or is likely to have celiac disease. In some embodiments, a ratio greater than 1 (e.g., greater than 2, 3, 4, 5, 6, 7, 8, 9, 10 or more) of the at least one circulating cytokine or chemokine to the control level, such as a baseline level, indicates that the subject has or is likely to have celiac disease. In some embodiments of any one of the methods provided herein, the method further comprises recording whether or not the subject has or is likely to have celiac disease based on the level or ratio.

In some embodiments, the level of the at least one circulating cytokine or chemokine is measured in a sample, e.g., a serum, plasma or urine sample, obtained from the subject. Samples are described elsewhere herein. In some embodiments, the sample is obtained from the subject within 1-24 hours, such as within 1-6 hours, of administration of the composition. In some embodiments, the sample is obtained from the subject within 4-6 hours of administration of the composition.

In some embodiments of any one of the methods provided herein, the method further comprises administering the composition comprising at least one gluten peptide as described herein to the subject, e.g., by injection. In some embodiments, the composition is administered via intradermal injection. In some embodiments, the composition is administered once. In some embodiments, the composition is administered once via intradermal injection.

In some embodiments of any one of the methods provided herein, the method further comprises performing other testing. Any method of other testing as described herein is contemplated. In some embodiments, the other testing comprises a serology test, genotyping, an intestinal biopsy, and/or a T cell response test. In some embodiments of any one of the methods provided herein, the method further comprises performing one or more additional tests on the subject. In some embodiments, the method further comprises contacting a sample comprising a T cell from the subject with a gluten peptide and measuring a T cell response in the sample. In some embodiments, a T cell response is measured by measuring a level of IFN-γ, where an increased level of IFN-γ compared to a control level (e.g., a level of IFN-γ in a sample that has not been contacted with a gluten peptide) may identify a subject as having Celiac disease. In some embodiments, a level of IFN-γ at or above a cut-off level (e.g., at or above 7.2 pg/ml) may identify a subject as having or likely as having Celiac disease.

In some embodiments of any one of the methods provided herein, the method further comprising treating or suggesting a treatment if the subject is identified as having or likely of having celiac disease. In some embodiments of any one of the methods provided herein, the method further comprises recommending a gluten-free diet and/or providing information in regard thereto to the subject. In some embodiments of any one of the methods provided herein, the method further comprises administering a treatment, or providing information in regard thereto, to the subject. Suitable treatments are described herein. In some embodiments, the treatment is a composition comprising a gluten peptide as described herein. In some embodiments, the treatment comprises a gluten-free diet.

In some embodiments, the method further comprises orally administering or directing the subject to consume gluten prior to the measuring step. In some embodiments, the subject is orally administered or directed to consume gluten for at least three days. In some embodiments, the measuring step is performed six days after the last of the gluten is orally administered or consumed.

Other aspects of the disclosure relate to a method comprising: administering to a subject that has or is suspected of having Celiac disease a first composition comprising at least one gluten peptide in an amount selected based on an HLA genotype of the subject, measuring a T cell response to a second composition comprising at least one gluten peptide in a sample from the subject, and assessing the likelihood that the subject has Celiac disease.

In some embodiments of any one of the methods provided, the first composition and the second composition comprise the same gluten peptide or peptides. In some embodiments of any of the methods provided, the sample is contacted with the second composition.

In some embodiments of any one of the methods provided, the method further comprises obtaining the sample from the subject.

In some embodiments of any one of the methods provided, the subject is orally administered or directed to consume gluten for at least three days.

In some embodiments of any one of the methods provided, the measuring step is performed six days after the last of the gluten is orally administered or consumed.

In some embodiments of any one of the methods provided, IFN-gamma is measured. In some embodiments of any one of the methods provided, IP-10 is measured.

In some embodiments of any one of the methods provided, the amount of the first composition, the second composition, or each of the first composition and second composition, is less than 150 micrograms if the subject has a homozygous HLA-DQ2.5 genotype. In some embodiments of any one of the methods provided, the amount of the first composition, the second composition, or each of the first composition and second composition, is less than 300 micrograms if the subject has a homozygous HLA-DQ2.5 genotype.

Therapeutic Efficacy Methods

One aspect of the disclosure relates to methods of assessing the efficacy of treatment of Celiac disease (e.g., responsiveness to a therapeutic gluten peptide composition). In some embodiments, the method comprises (a) measuring in a subject that has been administered a first composition comprising at least one gluten peptide.

(i) a level of at least one circulating cytokine or chemokine, and/or (ii) a level of at least one circulating T cell; and (b) assessing the efficacy based on the measuring. The method, in some embodiments, can further include (c) treating the subject, or suggesting a treatment to the subject, based on the assessing.

In some embodiments, assessing comprises comparing the level of the at least one circulating cytokine, chemokine, or T cell to a control level of the at least one circulating cytokine, chemokine, or T cell. Levels as used herein can be absolute or relative amounts. In some embodiments, assessing comprises determining the ratio of the level of the at least one circulating cytokine, chemokine, or T cell to the control level. In some embodiments, the control level of the at least one circulating cytokine, chemokine, or T cell is a baseline level of the circulating cytokine, chemokine, or T cell. In some embodiments, the baseline level is the level of the circulating cytokine, chemokine, or T cell in the subject prior to the administration of the one or more gluten peptides. In some embodiments of any one of the methods provided herein, the method can further comprise the step of determining a baseline level of the circulating cytokine, chemokine, or T cell in the subject.

In some embodiments, the assessing comprises comparing the level of the at least one circulating cytokine or chemokine, and/or the level of at least one circulating T cell to a circulating cytokine or chemokine control level, such as a baseline level, and/or a circulating T cell control level, respectively. In some embodiments, the method further comprises recording the level(s), the result(s) of the assessing and/or the treatment, or suggestion for treatment, based on the assessing.

In some embodiments, a ratio of about 1 of the at least one circulating cytokine, chemokine, or T cell compared to a control level, such as a baseline level or negative control, of the at least one circulating cytokine, chemokine, or T cell indicates that a treatment has been effective. In some embodiments, a ratio of greater than 1 of the at least one circulating cytokine, chemokine, or T cell compared to a control level, such as a baseline level or negative control, of the at least one circulating cytokine, chemokine, or T cell indicates that a treatment has not been effective or completely effective. In some embodiments, a ratio of greater than or about equal to 1 of the at least one circulating cytokine, chemokine, or T cell compared to a control level, such as a positive control, of the at least one circulating cytokine, chemokine, or T cell indicates that a treatment has not been effective or completely effective. In some embodiments, a ratio of less than 1 of the at least one circulating cytokine, chemokine, or T cell compared to a control level, such as a positive control, of the at least one circulating cytokine, chemokine, or T cell indicates that a treatment has been effective. In some embodiments, the method further comprises recording whether or not the treatment has been effective or completely effective based on the level or ratio.

In some embodiments, a level of the at least one circulating cytokine, chemokine, or T cell that is no more than two-fold above a control level, such as a baseline level or negative control, of the at least one circulating cytokine, chemokine, or T cell indicates that a treatment has been effective. In some embodiments, a level of the at least one circulating cytokine, chemokine, or T cell that is two-fold or more above a control level, such as a baseline level or negative control, of the at least one circulating cytokine, chemokine, or T cell indicates that a treatment has not been effective or completely effective. In some embodiments, a level of IL-2 and IL-8 that are each no more than two-fold above a control level, such as a baseline level or negative control, of IL-2 and IL-8 indicates that a treatment has been effective. In some embodiments, a level of IL-2 and IL-8 that is two-fold or more above a control level, such as a baseline level or negative control, of IL-2 and IL-8 indicates that a treatment has not been effective or completely effective.

In some embodiments, the measuring is performed on a sample obtained from the subject, e.g., a serum, plasma or urine sample. Samples are described herein. In some embodiments, the method further comprises obtaining the sample from the subject. In some embodiments, the sample is obtained from the subject within 4-6 hours of administration of the composition. In some embodiments, the sample is obtained from the subject within 1-24 hours, such as within 1-6 hours, of administration of the composition. In some embodiments, the sample is obtained from the subject within 4-6 hours of administration of the composition.

In some embodiments, the method further comprises administering the composition comprising at least one gluten peptide as described herein to the subject, e.g., by injection or oral administration. In some embodiments, the composition is administered via intradermal injection. In some embodiments, the composition is administered once. In some embodiments, the composition is administered once via intradermal injection.

In some embodiments, treating comprises continuing with the treatment, or suggesting comprises suggesting the subject continue with the treatment, based on the assessing. In some embodiments, treating comprises ceasing the treatment, or suggesting comprises suggesting the subject cease the treatment, based on the assessing. In some embodiments, treating comprises administering a different or additional treatment, or the suggesting comprises suggesting the subject be treated with an additional or different treatment, based on the assessing. Exemplary treatments are described herein. In some embodiments, the treatment is a composition comprising a gluten peptide as described herein.

In some embodiments, the method further comprises orally administering or directing the subject to consume gluten prior to the measuring step. In some embodiments, the subject is orally administered or directed to consume gluten for at least three days. In some embodiments, the measuring step is performed six days after the last of the gluten is orally administered or consumed.

In some embodiments, the method further comprises performing other testing. Any method of other testing as described herein is contemplated. In some embodiments, the other testing comprises a serology test, genotyping, an intestinal biopsy, and/or a T-cell response test. In some embodiments, the method further comprises contacting a sample comprising a T cell from the subject (e.g., a whole blood sample) with a gluten peptide and measuring a T cell response in the sample. In some embodiments, a T cell response is measured by measuring a level of IFN-γ. In some embodiments, a decreased or similar level of IFN-γ compared to a control level (e.g., a level of IFN-γ in a sample that has not been contacted with a gluten peptide) indicates that a treatment has been effective. In some embodiments, a level of IFN-γ below a cut-off level (e.g., below 7.2 pg/ml) indicates that a treatment has been effective. In some embodiments, a T cell response is measured by measuring a level of IFN-γ, where an elevated level of IFN-γ compared to a control level (e.g., a level of IFN-γ in a sample that has not been contacted with a gluten peptide) indicates that a treatment has not been effective. In some embodiments, a level of IFN-γ at or above a cut-off level (e.g., at or above 7.2 pg/ml) indicates that a treatment has not been effective.

Another aspect of the disclosure relates to methods of assessing tolerance to a gluten peptide in a subject having Celiac disease. In some embodiments, tolerance is a state of lessened responsiveness or non-responsiveness of the immune system to a gluten peptide.

In some embodiments, the method can be any of the methods provided herein. In one embodiment, the method comprises (a) measuring in a subject that has been administered a first composition comprising at least one gluten peptide a level of at least one circulating cytokine or chemokine; and (b) assessing the tolerance of the subject to the at least one gluten peptide based on the measuring. In some embodiments, the subject is a subject that has previously received or is receiving treatment for Celiac disease. In some embodiments, the treatment is a composition comprising a gluten peptide as described herein.

In some embodiments, assessing comprises comparing the level of the at least one circulating cytokine or chemokine to a control level of the at least one circulating cytokine or chemokine. Levels as used herein can be absolute or relative amounts. In some embodiments, assessing comprises determining the ratio of the level of the at least one circulating cytokine or chemokine to the control level. In some embodiments, the control level of the at least one circulating cytokine or chemokine is a baseline level of the circulating cytokine or chemokine. In some embodiments, the baseline level is the level of the circulating cytokine or chemokine in the subject prior to the administration of the one or more gluten peptides. In some embodiments of any one of the methods provided herein, the method can further comprise the step of determining a baseline level of the circulating cytokine or chemokine in the subject.

In some embodiments, the assessing comprises comparing the level of the at least one circulating cytokine or chemokine to a circulating cytokine or chemokine control level, such as a baseline level. In some embodiments, the method further comprises recording the level(s) or the result(s) of the assessing.

In some embodiments, a ratio of about 2 or less (e.g., less than 2, less than 1, or less than 0.5) of the at least one circulating cytokine or chemokine compared to a control level, such as a baseline level or negative control, of the at least one circulating cytokine or chemokine indicates that the subject has been tolerized to the gluten peptide. In some embodiments, a ratio of greater than about 2 (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30) of the at least one circulating cytokine or chemokine to a control level, such as a baseline level or negative control, of the at least one circulating cytokine or chemokine indicates that the subject has not been tolerized to the gluten peptide. In some embodiments, the method further comprises recording whether or not the subject has been tolerized to a gluten peptide based on the level or ratio.

In some embodiments, the measuring is performed on a sample obtained from the subject, e.g., a serum, plasma, or urine sample. Samples are described herein. In some embodiments, the method further comprises obtaining the sample from the subject. In some embodiments, the sample is obtained from the subject within 1-24 hours, such as within 1-6 hours, of administration of the composition. In some embodiments, the sample is obtained from the subject within 4-6 hours of administration of the composition.

In some embodiments, the method further comprises administering the composition comprising at least one gluten peptide as described herein to the subject, e.g., by injection or oral administration. In some embodiments, the composition is administered via intradermal injection. In some embodiments, the composition is administered once. In some embodiments, the composition is administered once via intradermal injection.

In some embodiments, the method further comprises treating the subject or recommending a treatment to the subject based on the assessing. In some embodiments, treating comprises continuing with the treatment, or suggesting comprises suggesting the subject continue with the treatment, based on the assessing. In some embodiments, treating comprises ceasing the treatment, or suggesting comprises suggesting the subject cease the treatment, based on the assessing. In some embodiments, treating comprises administering a different or additional treatment, or the suggesting comprises suggesting the subject be treated with an additional or different treatment, based on the assessing. Exemplary treatments are described herein. In some embodiments, the treatment is a composition comprising a gluten peptide as described herein. In some embodiments, the treatment comprises a gluten-free diet.

In some embodiments, the method further comprises orally administering or directing the subject to consume gluten prior to the measuring step. In some embodiments, the subject is orally administered or directed to consume gluten for at least three days. In some embodiments, the measuring step is performed six days after the gluten is orally administered or consumed.

In some embodiments, the method further comprises performing other testing. Any method of other testing as described herein is contemplated. In some embodiments, the other testing comprises a serology test, genotyping, an intestinal biopsy, and/or a T cell response test. In some embodiments, the method further comprises contacting a sample comprising a T cell from the subject (e.g., a whole blood sample) with a gluten peptide and measuring a T cell response in the sample. In some embodiments, a T cell response is measured by measuring a level of IFN-γ. In some embodiments, a decreased or similar level of IFN-γ compared to a control level (e.g., a level of IFN-γ in a sample that has not been contacted with a gluten peptide) may indicate that a subject has been tolerized to the gluten peptide. In some embodiments, a level of IFN-γ below a cut-off level (e.g., below 7.2 pg/ml) may indicate that a subject has been tolerized to the gluten peptide. In some embodiments, a T cell response is measured by measuring a level of IFN-γ, where an elevated level of IFN-γ compared to a control level (e.g., a level of IFN-γ in a sample that has not been contacted with a gluten peptide) may indicate that a subject has not been tolerized to the gluten peptide. In some embodiments, a level of IFN-γ at or above a cut-off level (e.g., above 7.2 pg/ml) may indicate that a subject has not been tolerized to the gluten peptide.

Circulating Cytokines and Chemokines

Aspects of the disclosure relate to circulating cytokines and/or chemokines and uses thereof in a method, composition or kit described herein. As used herein, a "circulating cytokine or chemokine" is a cytokine or chemokine present in vivo in a subject, e.g., within the blood, plasma, serum, urine etc. of the subject, that may be measured in a sample obtained from the subject, e.g., in a blood (such as plasma or serum) or urine sample. The levels of such circulating cytokines or chemokines may be increased or decreased in the subject as a result of administration of a composition comprising a gluten peptide to the subject, such as for a treatment of Celiac disease. Non-limiting examples of circulating cytokines and chemokines that can be used in any one of the methods, compositions and kits described herein include, but are not limited to, those shown in Table 2. The sequences of the genes, mRNAs, and proteins for each cytokines/chemokine can be determined by one of ordinary skill in the art using the National Center for Biotechnology Information (NCBI) gene database at www.ncbi.nlm.nih.gov/gene.

TABLE 2

Cytokines and chemokines.

| Cytokine or Chemokine Symbol | Cytokine or Chemokine Symbol (/Alternative Symbol) | NCBI Human Gene ID | NCBI Reference Sequences Human Protein ID(s) |
|---|---|---|---|
| Chemokine (C-C motif) ligand 2 | MCP-1/CCL2 | 6347 | NP_002973.1 |
| Chemokine (C-X-C motif) ligand 10 | IP-10/CXCL10 | 3627 | NP_001556.2 |
| Interleukin 6 | IL-6 | 3569 | NP_000591.1 |
| Interleukin 8 | IL-8 | 3576 | NP_000575.1 |
| Granulocyte colony-stimulating factor | G-CSF | 1440 | NP_000750.1, NP_001171618.1, NP_757373.1, NP_757374.2 |
| Interleukin 2 | IL-2 | 3558 | NP_000577.2 |
| Interleukin 1 receptor antagonist | IL-1RA | 3557 | NP_000568.1, NP_776213.1, NP_776214.1, NP_776215.1 |
| Chemokine (C-X-C motif) ligand 1 | GRO/CXCL1 | 2919 | NP_001502.1 |
| Chemokine (C-C motif) ligand 11 | EOTAXIN/CCL11 | 6356 | NP_002977.1 |
| Granulocyte-macrophage colony-stimulating factor | GM-CSF | 1437 | NP_000749.2 |
| Interleukin 10 | IL-10 | 3586 | NP_000563.1 |
| Tumor necrosis factor alpha | TNFa | 7124 | NP_000585.2 |
| Interferon, alpha 2 | IFNa2 | 3440 | NP_000596.2 |
| Chemokine (C-C motif) ligand 4 | MIP-1b/CCL4 | 6351 | NP_002975.1 |
| Interleukin 12 | IL-12P70 (heterodimer of IL-12A and IL-12B) | IL-12A 3592 IL-12B 3593 | IL-12A NP_000873.2 IL-12B NP_002178.2 |
| Interleukin 1, alpha | IL-1a | 3552 | NP_000566.3 |
| Interleukin 17A | IL-17A | 3605 | NP_002181.1 |
| Epidermal growth factor | EGF | 1950 | NP_001171601.1, NP_001171602.1, NP_001954.2 |
| Chemokine (C-C motif) ligand 3 | MIP-1a/CCL3 | 6348 | NP_002974.1 |
| Chemokine (C-X3-C motif) ligand 1 | FRACTALKINE/CX3CL1 | 6376 | NP_002987.1 |
| Interferon gamma | IFNg or IFN-γ | 3458 | NP_000610.2 |
| Vascular endothelial growth factor | VEGF | 7422 | NP_001020537.2, NP_001020538.2, NP_001020539.2, NP_001020540.2, NP_001020541.2, NP_001028928.1, NP_001165093.1, NP_001165094.1, NP_001165095.1, NP_001165096.1, NP_001165097.1, NP_001165098.1, NP_001165099.1, NP_001165100.1, NP_001165101.1, NP_001191313.1, NP_001191314.1, NP_001273973.1, NP_003367.4 |
| Interleukin 9 | IL-9 | 3578 | NP_000581.1 |
| Fibroblast growth factor 2 | FGF-2 | 2247 | NP_001997.5 |
| Interleukin 1, beta | IL-1b | 3553 | NP_000567.1 |
| Fms-related tyrosine kinase 3 ligand | Flt-3L | 2323 | NP_001191431.1, NP_001191432.1, NP_001265566.1, NP_001265567.1 |
| Interleukin 15 | IL-15 | 3600 | NP_000576.1, NP_751915.1 |

TABLE 2-continued

Cytokines and chemokines.

| Cytokine or Chemokine Symbol | Cytokine or Chemokine Symbol (/Alternative Symbol) | NCBI Human Gene ID | NCBI Reference Sequences Human Protein ID(s) |
|---|---|---|---|
| Lymphotoxin alpha | TNFb/LTA | 4049 | NP_000586.2, NP_001153212.1 |
| Interleukin 12B | IL-12(P40)/IL12B | 3593 | NP_002178.2 |
| Chemokine (C-C motif) ligand 7 | MCP-3/CCL7 | 6354 | NP_006264.2 |
| Interleukin 4 | IL-4 | 3565 | NP_000580.1, NP_758858.1 |
| Chemokine (C-C motif) ligand 22 | MDC/CCL22 | 6367 | NP_002981.2 |
| Interleukin 13 | IL-13 | 3596 | NP_002179.2 |
| soluble CD40 ligand | sCD40L | 959 | NP_000065.1 |
| Transforming growth factor, alpha | TGF-a | 7039 | NP_001093161.1, NP_003227.1 |
| Interleukin 3 | IL-3 | 3562 | NP_000579.2 |
| Interleukin 5 | IL-5 | 3567 | NP_000870.1 |
| Interleukin 7 | IL-7 | 3574 | NP_000871.1, NP_001186815.1, NP_001186816.1, NP_001186817.1 |

In some embodiments, the at least one circulating cytokine or chemokine is MCP-1, IL-6, IL-10, IL-8, or G-CSF. In some embodiments, the at least one circulating cytokine or chemokine is IL-2, IL-8, IL-10, or MCP-1. In some embodiments, the at least one circulating cytokine or chemokine comprises one or more of IL-2, IL-8, IL-10, and MCP-1. In some embodiments, the at least one circulating cytokine or chemokine comprises IL-2, IL-8, IL-10, and MCP-1. In some embodiments, the at least one circulating cytokine or chemokine comprises IL-8, IL-10, and MCP-1. In some embodiments, the at least one circulating cytokine or chemokine comprises IL-2, IL-10, and MCP-1. In some embodiments, the at least one circulating cytokine or chemokine comprises IL-2, IL-8, and MCP-1. In some embodiments, the at least one circulating cytokine or chemokine comprises IL-2, IL-8, and IL-10. In some embodiments, the at least one circulating cytokine or chemokine is MCP-1, IL-6, IL-8, or G-CSF. In some embodiments, the at least one circulating cytokine or chemokine is IL-2, IL-8, or MCP-1. In some embodiments, the at least one circulating cytokine or chemokine comprises one or more of IL-2, IL-8, and MCP-1. In some embodiments, the at least one circulating cytokine or chemokine comprises IL-8 and MCP-1. In some embodiments, the at least one circulating cytokine or chemokine comprises IL-2 and MCP-1. In some embodiments, the at least one circulating cytokine or chemokine comprises IL-2 and IL-8. In some embodiments, the at least one circulating cytokine or chemokine comprises IL-2. In some embodiments, the at least one circulating cytokine or chemokine comprises IL-8. In some embodiments, the at least one circulating cytokine or chemokine comprises MCP-1. In some embodiments, the at least one circulating cytokine or chemokine comprises one or more of IL-2, IP-10, and IFN-γ. In some embodiments, the at least one circulating cytokine or chemokine comprises IL-2, IP-10, and IFN-γ.

In some embodiments, an elevated level (e.g., an elevated level of protein or nucleic acid (e.g., mRNA level)) of the at least one circulating cytokine or chemokine compared to a control level of the at least one circulating cytokine or chemokine indicates that the subject has or is likely to have celiac disease. In some embodiments, methods provided herein comprise use of the ratio of the level of the at least one circulating cytokine or chemokine to a control level, such as a baseline level.

In some embodiments, the level of more than one circulating cytokine or chemokine is measured, e.g., the level of 2, 3, 4, 5, 6, 7, 8, 9, 10, 11, 12, 13, 14, 15, 16, 17, 18, 19, 20, 21, 22, 23, 24, 25, 26, 27, 28, 29, 30 or more circulating cytokines or chemokines.

Assays for detecting cytokine or chemokine protein levels include, but are not limited to, immunoassays (also referred to herein as immune-based or immuno-based assays, e.g., Western blot or enzyme-linked immunosorbent assay (ELISA)), Mass spectrometry, and multiplex bead-based assays. Binding partners for protein detection can be designed using methods known in the art and as described herein. In some embodiments, the protein binding partners, e.g., antibodies, bind to a part of or an entire amino acid sequence of at least one cytokine or chemokine, the sequence(s) being identifiable using the Genbank IDs described herein. Other examples of protein detection and quantitation methods include multiplexed immunoassays as described for example in U.S. Pat. Nos. 6,939,720 and 8,148,171, and published U.S. Patent Application No. 2008/0255766, and protein microarrays as described for example in published U.S. Patent Application No. 2009/0088329.

An exemplary ELISA involves at least one binding partner, e.g., an antibody or antigen-binding fragment thereof, with specificity for the at least one cytokine or chemokine. The sample with an unknown amount of the at least one cytokine or chemokine can be immobilized on a solid support (e.g., a polystyrene microtiter plate) either non-specifically (via adsorption to the surface) or specifically (via capture by another binding partner specific to the same at least one cytokine, as in a "sandwich" ELISA). After the cytokine or chemokine is immobilized, the binding partner for the at least one cytokine or chemokine can be added, forming a complex with the immobilized at least one cytokine or chemokine. The binding partner can be attached to a detectable label as described herein (e.g., a fluorophore or an enzyme), or can itself be detected by an agent that recognizes the at least one cytokine or chemokine binding partner that is attached to a detectable label as described herein (e.g., a fluorophore or an enzyme). If the detectable label is an enzyme, a substrate for the enzyme is added, and the enzyme elicits a chromogenic or fluorescent signal by acting on the substrate. The detectable label can then be detected using an appropriate machine, e.g., a fluorimeter or spectrophotometer, or by eye.

Assays may also include a multiplex bead-based assay, such as an assay commercially available from Luminex (see, e.g., the MAGPIX® system). Multiplex bead-based assays are known in the art.

Assays for detecting cytokine or chemokine nucleic acid, such as RNA, include, but are not limited to, Northern blot analysis, RT-PCR, sequencing technology, RNA in situ hybridization (using e.g., DNA or RNA probes to hybridize RNA molecules present in the sample), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer with addressable location, such as Affymetrix microarray (Affymetrix®, Santa Clara, Calif.)). Designing nucleic acid binding partners, such as probes, is well known in the art. In some embodiments, the nucleic acid binding partners bind to a part of or an entire nucleic acid sequence of at least one cytokine or chemokine, the sequence(s) being identifiable using the Genbank IDs described herein.

Circulating T Cells

Aspects of the disclosure relate to circulating T cells and uses thereof in a method or kit described herein. As used herein, a "circulating T cell" is a T cell present in vivo in a subject, e.g., within the blood of the subject, that may be measured in a sample obtained from the subject, e.g., in a blood (such as plasma or serum) sample. The levels of such circulating T cells may be increased or decreased in the subject as a result of administration of a composition comprising a gluten peptide to the subject. Non-limiting examples of circulating T cells that can be used in the methods and kits described herein include, but are not limited to, at least one circulating T cell that recognizes at least one gluten peptide, e.g., a gluten peptide comprised in a composition described herein. In some embodiments, the T cells recognizes at least one of: (i) a first peptide comprising the amino acid sequence PFPQPELPY (SEQ ID NO: 1) and PQPELPYPQ (SEQ ID NO: 2), (ii) a second peptide comprising the amino acid sequence PFPQPEQPF (SEQ ID NO: 3) and PQPEQPFPW (SEQ ID NO: 4), and (iii) a third peptide comprising the amino acid sequence PIPEQPQPY (SEQ ID NO: 5). A T cell that recognizes a gluten peptide is a T cell that comprises a T cell receptor that binds to the gluten peptide and/or that binds to the gluten peptide attached to one or more Major Histocompatibility Complex (MHC) molecules. In some embodiments, the circulating T cell is a CD4+ T cell. In some embodiments, the level of more than one circulating T cell is measured. The circulating T cell may be measured by direct assessment of T cells, for example by staining with MHC-peptide multimer and flow cytometery or by functional cytokine release assays, such as interferon-γ secretion in plasma from whole blood incubated with the cognate peptide of the T cell population of interest (e.g., a gluten peptide described herein) or another T cell response method described herein or otherwise known in the art.

Assays for detecting circulating T cells include, but are not limited to, a Major Histocompatibility Complex (MHC) tetramer assay and a T cell response assay. Such assays are known in the art (see, e.g., John D. Altman et al. (1996). "Phenotypic Analysis of Antigen-Specific T Lymphocytes." Science 274 (5284): 94-96; Hanne Quarsten et al. (2001) "Staining of Celiac Disease-Relevant T Cells by Peptide-DQ2 Multimers." Journal of Immunology 167(9):4861-4868; Melinda Rai et al. (2007) "Tetramer visualization of gut-homing gluten-specific T cells in the peripheral blood of celiac disease patients." PNAS 104(8): 2831-2836). T cell response assays are described herein and are known in the art (see, e.g., Ontiveros N, Tye-Din J A, Hardy M Y, Anderson R P. Ex vivo whole blood secretion of interferon-γ (IFN-γ) and IFN-γ-inducible protein-10 (IP-10) measured by ELISA are as sensitive as IFN-γ ELISpot for the detection of gluten-reactive T cells in HLA-DQ2.5+ associated celiac disease. Clin Exp Immunol. 2014; 175:305-315).

An exemplary MHC tetramer assay involves use of DQ2 (DQA1*0501/DQB1*0201) MHC molecules containing a biotin. The DQ2 molecules are mixed with peptides, e.g., gluten peptides, to form DQ2-peptide complexes. Tetramers may be made by conjugating the DQ2-peptide complexes with streptavidin labeled with a fluorophore. For tetramer staining, circulating T cells are contacted with the tetramers and the tetramers bound to the circulating T cells are then detected, e.g., by flow cytometry. Secondary T cell markers may also be used in connection with the tetramer assay, e.g., anti-CD4 antibodies, anti-CD3 antibodies, and anti-CD45RA antibodies.

Samples

Samples, as used herein, refer to biological samples taken or derived from a subject, e.g., a subject having or suspected of having Celiac disease. Examples of samples include tissue samples or fluid samples. In some embodiments, the sample is a buccal swab or a buffy coat (e.g., isolated from anti-coagulant treated blood such as blood treated with EDTA or citrate).

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, techniques utilized in the present disclosure are standard procedures, well known to those skilled in the art. Such techniques are described and explained throughout the literature in sources such as, J. Perbal, A Practical Guide to Molecular Cloning, John Wiley and Sons (1984); J. Sambrook et al., Molecular Cloning: A Laboratory Manual, Cold Spring Harbour Laboratory Press (1989); T. A. Brown (editor), Essential Molecular Biology: A Practical Approach, Volumes 1 and 2, IRL Press (2000 and 1991); D. M. Glover and B. D. Hames (editors), DNA Cloning: A Practical Approach, Volumes 1-4, IRL Press (1995 and 1996); F. M. Ausubel et al. (editors), Current Protocols in Molecular Biology, Greene Pub. Associates and Wiley-Interscience (1988, including all updates until present); Ed Harlow and David Lane (editors) Antibodies: A Laboratory Manual, Cold Spring Harbour Laboratory, (1988); and J. E. Coligan et al. (editors), Current Protocols in Immunology, John Wiley & Sons (including all updates until present).

In any one aspect or embodiment provided herein "comprising" may be replaced with "consisting essentially of" or "consisting of".

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Results of the Phase I Randomized, Double-Blind, Placebo-Controlled, Multiple Ascending Dose Study in Patients with Celiac Disease 3 cohorts of subjects with HLA-DQ2.5+(heterozygous or homozygous) biopsy-proven Celiac disease on a gluten-free diet for at least 1 year were included in the study. The first cohort (Cohort 1) contained 12 subjects who were dosed with 150 mcg of a gluten peptide composition (an equimolar composition in sodium chloride 0.9% USP of 3 peptides: ELQPFPQPELPYPQPQ (SEQ ID NO: 9), EQPFPQPEQP-FPWQP (SEQ ID NO: 10), and EPEQPIPEQPQPYPQQ (SEQ ID NO: 11), each peptide comprising an N-terminal pyroglutamate and C-terminal amidated amino acid) or a placebo (sodium chloride 0.9% USP) intradermally, twice a week for 8 weeks total. The second cohort (Cohort 2) contained 13 subjects who were dosed with 300 mcg of the gluten peptide composition or the placebo intradermally, twice a week for 8 weeks total. The gluten peptide composition to placebo ratio for each of Cohorts 1 and 2 were 2:1. Both Cohorts 1 and 2 received an oral gluten challenge and were assessed for gamma-interferon (gIFN) release and then returned to baseline prior to starting the treatment regimen. The third cohort (Cohort 7) contained 14 subjects who were dosed with 150 mcg of the peptide composition or the placebo intradermally, twice a week for 8 weeks total. The peptide composition to placebo ratio for Cohort 7 was 1:1. The subjects in Cohort 7 did not undergo an oral gluten challenge or a gIFN release assay before starting the dosage regimen.

The progress of each subject before, during and after the trial was assessed using multiple tests including serology (tTG-IgA, DGP-IgG, DGP-IgA, and EMA-IgA), histology, and IFNg whole blood release assay, and cytokine/chemokines in plasma (measured by MAGPIX® multiplex platform). Plasma cytokines and chemokines were measured at several timepoints pre and post first and last dose.

Subject disposition is summarized in Table 3. Subject demographics are summarized in Table 4. The extent of exposure for each subject is summarized in Table 5.

TABLE 3

Subject disposition.

| Completion Status | Cohort 1 (150 mg) (N = 8) | Cohort 2 (300 mg) (N = 8) | Cohort 7 (150 mg) (N = 7) | Placebo (from Cohorts 1 and 2) (N = 7) | Placebo (from Cohort 7) (N = 7) | All Subjects Dosed (N = 39) | All Subjects Screened (N = 67) |
|---|---|---|---|---|---|---|---|
| Screened | | | | | | | 67 (100%) |
| Enrolled | 8 (100%) | 10 (100%) | 7 (100%) | 7 (100%) | 7 (100%) | 39 (100%) | 39 (58%) |
| Completed the study as required | 8 (100%) | 6 (60%) | 7 (100%) | 6 (86%) | 7 (100%) | 34 (87%) | |
| Completed study treatment per protocol (received at least 15 of 16 doses) | 8 (100%) | 2 (20%) | 7 (100%) | 5 (71%) | 7 (100%) | 29 (74%) | |
| Received all 16 doses of study treatment | 7 (88%) | 2 (20%) | 5 (71%) | 4 (57%) | 6 (86%) | 24 (62%) | |
| Discontinued the study prior to completion | | 8 (80%) | | 2 (29%) | | 10 (26%) | |

TABLE 4

Subject Demographics

| Parameter | Statistic | Cohort 1 (150 mg) (N = 8) | Cohort 2 (300 mg) (N = 10) | Cohort 7 (150 mg) (N = 7) | Placebo (pooled) (N = 14) | All subjects dosed (N = 39) |
|---|---|---|---|---|---|---|
| Age (years) | | | | | | |
| | N | 8 | 10 | 7 | 14 | 39 |
| | Mean | 52.0 | 50.0 | 42.6 | 39.1 | 45.2 |
| | SD | 11.9 | 10.1 | 5.4 | 15.5 | 13.0 |
| | Median | 52.5 | 52.0 | 45.0 | 34.0 | 47.0 |

TABLE 4-continued

Subject Demographics

| Parameter | Statistic | Cohort 1 (150 mg) (N = 8) | Cohort 2 (300 mg) (N = 10) | Cohort 7 (150 mg) (N = 7) | Placebo (pooled) (N = 14) | All subjects dosed (N = 39) |
|---|---|---|---|---|---|---|
| | Min | 31 | 28 | 33 | 18 | 18 |
| | Max | 66 | 64 | 47 | 64 | 66 |
| Race | | | | | | |
| White | n (%) | 8 | 10 | 7 | 14 | 39 (100%) |
| Sex | | | | | | |
| Female | n (%) | 7 | 7 | 5 | 10 | 29 (74%) |
| Male | n (%) | 1 | 3 | 2 | 4 | 10 (26%) |
| Height (cm) | | | | | | |
| | N | 8 | 10 | 7 | 14 | 39 |
| | Mean | 167.7 | 170.1 | 168.4 | 170.6 | 169.5 |
| | SD | 10.0 | 9.8 | 8.3 | 10.0 | 9.4 |
| | Median | 168.7 | 167.0 | 173.0 | 170.5 | 169.0 |
| | Min | 154 | 158 | 156 | 156 | 154 |
| | Max | 186 | 186 | 179 | 186 | 186 |
| Weight (kg) | | | | | | |
| | N | 8 | 10 | 7 | 14 | 39 |
| | Mean | 70.66 | 85.34 | 74.40 | 66.55 | 73.62 |
| | SD | 11.17 | 13.02 | 11.58 | 12.91 | 14.07 |
| | Median | 69.20 | 85.05 | 73.00 | 64.10 | 70.50 |
| | Min | 60.2 | 66.0 | 58.5 | 48.5 | 48.5 |
| | Max | 95.1 | 105.5 | 92.5 | 92.3 | 105.5 |
| BMI (kg/m^2) | | | | | | |
| | N | 8 | 10 | 7 | 14 | 39 |
| | Mean | 25.24 | 29.55 | 26.13 | 22.81 | 25.63 |
| | SD | 4.28 | 4.54 | 2.63 | 3.72 | 4.60 |
| | Median | 23.91 | 28.91 | 25.23 | 22.64 | 25.23 |
| | Min | 20.7 | 25.2 | 23.3 | 17.2 | 17.2 |
| | Max | 33.2 | 40.2 | 30.9 | 32.3 | 40.2 |

TABLE 5

Summary of subject exposure

| Cohort | Treatment | Dose level | Number of Doses | Total Dose | Number of Subjects |
|---|---|---|---|---|---|
| 1 | peptide composition | 150 | 16 | 2400 | 7 |
| 1 | peptide composition | 150 | 15 | 2250 | 1 |
| 1 | Placebo | 0 | 16 | 0 | 4 |
| 2 | peptide composition | 300 | 16 | 4800 | 2 |
| 2 | peptide composition | 300 | 5 | 1500 | 1 |
| 2 | peptide composition | 300 | 4 | 1200 | 2 |
| 2 | peptide composition | 300 | 3 | 900 | 1 |
| 2 | peptide composition | 300 | 2 | 600 | 1 |
| 2 | peptide composition | 300 | 1 | 300 | 3 |
| 2 | Placebo | 0 | 15 | 0 | 1 |
| 2 | Placebo | 0 | 10 | 0 | 1 |
| 2 | Placebo | 0 | 5 | 0 | 1 |
| 7 | peptide composition | 150 | 16 | 2400 | 5 |
| 7 | peptide composition | 150 | 15 | 2250 | 2 |
| 7 | Placebo | 0 | 16 | 0 | 6 |
| 7 | Placebo | 0 | 15 | 0 | 1 |

Through random distribution of the subjects, all of the subjects who were homozygous for HLA-DQ2.5 received the gluten peptide composition treatment (FIG. 1). Non-homozygous HLA-DQ2.5 subjects received either the gluten peptide composition treatment or placebo (FIG. 1). A qualitative functional HLA-DQ2.5 "dose" was estimated based on the genotype of each subject. If the subject had the DQA1*05 allele for both copies of the HLA-DQA gene and had the DQB1*02 allele for both copies of the HLA-DQB gene (i.e., was homozygous for HLA-DQ2.5), the functional HLA-DQ2.5 dose was high. If the subject had the DQA1*05 allele for one copy of the HLA-DQA gene and had the DQB1*02 allele for one copy of the HLA-DQB gene (i.e., was heterozygous for HLA-DQ2.5), the functional HLA-DQ2.5 dose was low. If the subject had the HLA-DQ2.5/2.2 genotype (i.e., the subject had two DQB1*02 alleles for the HLA-DQB gene and one copy of the DQA1*05 allele for the HLA-DQA gene), the functional HLA-DQ2.5 dose was intermediate because the subject was homozygous for DQB1*02 and heterozygous for DQA1*05. If the subject had the HLA-DQ2.5/7 genotype (i.e., the subject had one DQB1*02 allele for the HLA-DQB gene and two copies of the DQA1*05 allele for the HLA-DQA gene), the functional HLA-DQ2.5 dose was intermediate because the subject was heterozygous for DQB1*02 and homozygous for DQA1*05.

Figure 4:
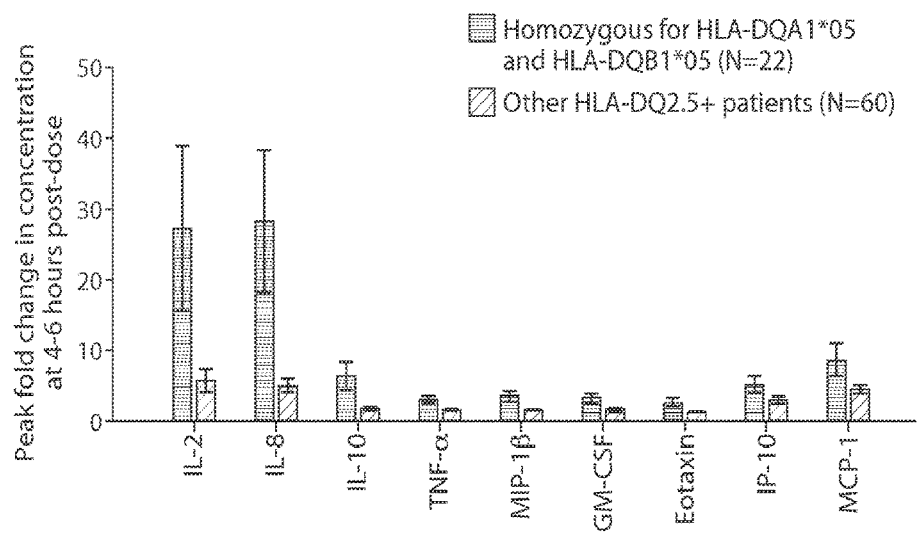
FIG. 4 is a graph showing peak fold change in concentration of IL-2, IL-8, IL-10, TNF-α, MIP-1β, GM-CSF, Eotaxin, IP-10, and MCP-1 at 4-6 hours after dose of the gluten peptide composition in subjects that were homozygous for HLA-DQ2.5 (n=22) or heterozygous HLA-DQ2.5/2.2 or 2.5/7, heterozygous HLA-DQ2.5 or HLA-DQ2.5/unknown (n=60).

It was found that subjects that had a high functional HLA-DQ2.5 dose (i.e., were homozygous for HLA-DQ2.5) had generally increased levels of circulating cytokines in response to administration of the gluten peptide composition when received at a dose of 150 micrograms compared to subjects with other genotypes that received the same dose of the gluten peptide composition (FIG. 2, FIG. 3 and FIG. 4). It was also found that subjects that had a high functional HLA-DQ2.5 dose (i.e., were homozygous for HLA-DQ2.5)

had more adverse symptoms in response to administration of the gluten peptide composition when received at a dose of 300 micrograms compared to subjects with other genotypes that received the same dose of the gluten peptide composition (FIG. 2).

It was also found that subjects that had a high functional HLA-DQ2.5 dose (i.e., were homozygous for HLA-DQ2.5) had more treatment emergent adverse events in response to administration of the gluten peptide composition when received at a dose of 300 micrograms or 150 micrograms compared to subjects with other genotypes that received the same dose of the gluten peptide composition (Table 6).

TABLE 6

Treatment emergent adverse events

|  | # Subjects in Cohort | # Subjects reporting moderate/ severe AEs | Total # moderate/ severe AEs reported | # HLA-DQ2.5 homozygous subjects in cohort | # HLA-DQ2.5 homozygous subjects reporting moderate/ severe AEs | Total # moderate/ severe AEs reported by HLA-DQ2.5 homozygous subjects |
|---|---|---|---|---|---|---|
| Cohort 1 | 8 | 6 | 11 | 4 | 4 | 8 |
| Cohort 2 | 10 | 8 | 12 | 1 | 1 | 3 |
| Cohort 7 | 7 | 3 | 4 | 2 | 2 | 3 |

As a result, it is expected that a subject who is homozygous for HLA-DQ2.5 may benefit from a lower dosage of a gluten peptide treatment compared to subjects who have a non-homozygous genotype (e.g., are HLA-DQ2.5 heterozygotes).

Example 2: Preparation of a 150 Microgram Dosage Composition of the First, Second, and Third Peptide A dose of 150 µg the peptide composition was defined by there being 50 µg (26.5 nmol) of pure peptide 1 (ELQPFPQPELPYPQPQ (SEQ ID NO: 9)) comprising an N-terminal pyroglutamate and C-terminal amidated amino acid), and an equimolar amount of peptide 2 and peptide 3 (EQPFPQPEQPFPWQP (SEQ ID NO: 10)) and EPEQPIPEQPQPYPQQ (SEQ ID NO: 11)), respectively, each peptide comprising an N-terminal pyroglutamate and C-terminal amidated amino acid). The molar equivalent of 50 µg peptide 1 was given by 50 µg/1889.3 g/mol=26.5 nmol. When preparing a solution containing 150 µg of the peptide composition, for the constituent peptides, the weight of each peptide was adjusted according to peptide purity and peptide content of the lyophilized stock material. For example, if the peptide 1 stock material had peptide purity of 98% and its peptide content was 90%, the weight of stock material yielding 50 µg peptide 1 was 50 µg/(peptide purity× peptide content)=50 ug/(0.98×0.90)=56.7 ug.

The molar amount of peptide 1 in 150 µg of the peptide composition was 26.5 nmol, and the weight of lyophilized peptide 2 stock material was therefore given by 26.5 nmol× 1833.2 g/mol/(peptide purity×peptide content). For example, if peptide 2 peptide purity was 99%, and peptide content of 95%, the mass of stock required was 51.7 ug.

The molar amount of peptide 3 in 150 ug of the peptide composition was 26.5 nmol, and the weight of lyophilized peptide 3 stock material was therefore given by 26.5 nmol× 1886.2 g/mol/(peptide purity×peptide content). For example, if peptide 3 peptide purity was 98%, and peptide content of 92%, the mass of stock required was 55.4 ug.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
assessing a human leukocyte antigen (HLA) genotype of a subject to determine whether the subject has a homozygous genotype or a heterozygous genotype;
selecting or adjusting a dose of a gluten peptide treatment for the subject based on the HLA genotype of the subject, and
administering the selected or adjusted dose of the gluten peptide treatment to the subject, wherein the subject has or is suspected of having Celiac disease, and
wherein the dose is adjusted or selected for the subject such that the amount is sufficient to provide a therapeutic or physiological effect without causing severe adverse effects.

2. The method of claim 1,
wherein the assessing comprises determining the sequence of each copy of an HLA-DQA gene and each copy of an HLA-DQB gene in the subject.

3. The method of claim 2, wherein the determining comprises performing a nucleic-acid based assay on each copy of the HLA-DQA gene, or a portion thereof, and each copy of the HLA-DQB gene, or a portion thereof.

4. The method of claim 3, wherein the nucleic-acid based assay is a probe-based assay or a sequencing assay.

5. The method of claim 1, wherein the assessing further comprises identifying the subject as having a homozygous HLA-DQ2.5 genotype or a non-homozygous HLA-DQ2.5 genotype.

6. The method of claim 5, wherein the non-homozygous HLA-DQ2.5 genotype is a heterozygous HLA-DQ2.5 genotype.

7. The method of claim 6, wherein the heterozygous HLA-DQ2.5 genotype is HLA-DQ$^{2.5/2.2}$, HLA-DQ$^{2.5/7}$, or HLA-DQ$^{2.5/8}$.

8. The method of claim 1, wherein the method further comprises:
decreasing a dose of the gluten peptide treatment if the subject has a homozygous HLA-DQ2.5 genotype; or
maintaining or increasing the dose of the gluten peptide treatment if the subject has a non-homozygous HLA-DQ2.5 genotype.

9. The method of claim 1, wherein the gluten peptide treatment comprises a composition comprising:
a first peptide comprising the amino acid sequence PFPQPELPY (SEQ ID NO:1) and the amino acid sequence PQPELPYPQ (SEQ ID NO:2);
a second peptide comprising the amino acid sequence PFPQPEQPF (SEQ ID NO:3) and the amino acid sequence PQPEQPFPW (SEQ ID NO:4); and
a third peptide comprising the amino acid sequence EQPIPEQPQ (SEQ ID NO:6) and the amino acid sequence PIPEQPQPY (SEQ ID NO:5).

10. The method of claim 9, wherein the dose is or is decreased to less than 300 micrograms if the subject has a homozygous HLA-DQ2.5 genotype.

11. The method of claim 10, wherein the dose is or is decreased to less than 150 micrograms if the subject has a homozygous HLA-DQ2.5 genotype.

12. The method of claim 9, wherein:
the first peptide comprises the amino acid sequence LQPFPQPELPYPQPQ (SEQ ID NO: 62);
the second peptide comprises the amino acid sequence QPFPQPEQPFPWQP (SEQ ID NO: 7); and
the third peptide comprises the amino acid sequence PEQPIPEQPQPYPQQ (SEQ ID NO: 8).

13. The method of claim 12, wherein:
the first peptide comprises the amino acid sequence ELQPFPQPELPYPQPQ (SEQ ID NO: 9), wherein the N-terminal glutamate is a pyroglutamate and the C-terminal glutamine is amidated;
the second peptide comprises the amino acid sequence EQPFPQPEQPFPWQP (SEQ ID NO:10), wherein the N-terminal glutamate is a pyroglutamate and the C-terminal proline is amidated; and
the third peptide comprises the amino acid sequence EPEQPIPEQPQPYPQQ (SEQ ID NO: 11), wherein the N-terminal glutamate is a pyroglutamate and the C-terminal glutamine is amidated.

\* \* \* \* \*